US007230003B2

(12) United States Patent
Gallop et al.

(10) Patent No.: US 7,230,003 B2
(45) Date of Patent: Jun. 12, 2007

(54) AROMATIC PRODRUGS OF PROPOFOL, COMPOSITIONS AND USES THEREOF

(75) Inventors: Mark A. Gallop, Los Altos, CA (US); Feng Xu, Palo Alto, CA (US)

(73) Assignee: XenoPort, Inc., Santa Clara, CA (US)

( * ) Notice: Subject to any disclaimer, the term of this patent is extended or adjusted under 35 U.S.C. 154(b) by 0 days.

(21) Appl. No.: 10/958,089

(22) Filed: Sep. 9, 2004

(65) Prior Publication Data
US 2005/0107385 A1 May 19, 2005

Related U.S. Application Data

(60) Provisional application No. 60/501,609, filed on Sep. 9, 2003.

(51) Int. Cl.
*A61K 31/44* (2006.01)
*A61K 31/235* (2006.01)
(52) U.S. Cl. ............... 514/277; 546/335; 560/106; 514/345; 514/352; 514/543; 514/544; 514/532
(58) Field of Classification Search ............... 546/335; 560/106
See application file for complete search history.

(56) References Cited

U.S. PATENT DOCUMENTS

| 3,845,770 | A | 11/1974 | Theeuwes et al. |
| 3,916,899 | A | 11/1975 | Theeuwes et al. |
| 4,765,539 | A | 8/1988 | Noakes et al. |
| 4,962,885 | A | 10/1990 | Coffee |
| 5,112,598 | A | 5/1992 | Biesalski |
| 5,556,611 | A | 9/1996 | Biesalski |
| 5,698,155 | A | 12/1997 | Grosswald et al. |
| 5,950,619 | A | 9/1999 | van der Linden et al. |
| 5,954,047 | A | 9/1999 | Armer et al. |
| 5,970,974 | A | 10/1999 | van Der Linden et al. |
| 6,254,853 | B1 | 7/2001 | Hendler et al. |
| 6,362,234 | B1 | 3/2002 | Hendler |
| 2001/0025035 | A1 | 9/2001 | Stella et al. |

FOREIGN PATENT DOCUMENTS

| WO | WO 94/12285 A2 | 6/1994 |
| WO | WO 94/12285 A3 | 6/1994 |
| WO | WO 94/14543 A2 | 7/1994 |
| WO | WO 94/14543 A3 | 7/1994 |
| WO | WO 95/26234 A1 | 10/1995 |
| WO | WO 95/26235 A1 | 10/1995 |
| WO | WO 95/32807 A1 | 12/1995 |
| WO | WO 99/58555 A2 | 11/1999 |
| WO | WO 99/58555 A3 | 11/1999 |
| WO | WO 00/48572 A1 | 8/2000 |
| WO | WO 00/54588 A1 | 9/2000 |
| WO | WO 02/13810 A1 | 2/2002 |

OTHER PUBLICATIONS

Hattori, T et al 'Accelerating effect of meta substituents in the ester-mediated nucleophilic aromatic substitution reaction' CA 130:109862 (1998).*
Hattori, T et al '1-arylfluorenols: convenient preparation via the ester-mediated nucleophilic aromatic substitution portocol, facil racemization, and intrinsic chiral induction ability' CA 129:330529 (1998).*
Trapani, G et al 'Propofol analogs. Synthesis, relationships between structure and affinity of GABAA receptor in rat brain, and differential electrophysiological profile at recombinant human GABAA receptors' CA 128:252919 (1998).*
Hattori, T et al 'Convenient synthesis of triarylamines via ester-mediated nucleophilic aromatic substitution' CA 125:33232 (1996).*
Hattori, T et al 'Facil construction of the 1-phenylnaphthyl skeleton via an ester-mediated nucleophilic aromatic substitution reaction. Applications to the synthesis of phenylnaphthalide lignans' CA 122:239427 (1995).*
Pop, E et al 'A theoretical study of the hydrolysis of some sterically hindered phenolic esters' CA 118:168494 (1993).*
Trapani, Propofol in anesthesia. Mechanism of action, structure-activity relationships, and drug delivery, (2000), PMID:10637364.*
Alderman, "A Review of Cellulose Ethers in Hydrophylic Matrices for Oral Controlled-Release Dosage Forms," *Int. J. Pharm. Tech. & Prod. Mfr.* 1984, 5(3) 1-9.
Anderson et al., "α-Amino Acid Phenolic Ester Derivatives: Novel Water-Soluble General Anesthetic Agents Which Allosterically Modulate $GABA_A$ Receptors," *J. Med. Chem.* 2001, 44, 3582-3591.
Bamba et al., "Release Mechanisms in Gelforming Sustained Release Preparations," *Int. J. Pharm.* 1979, 2, 307.
Banaszczyk et al., "Propofol Phosphate, a Water-Soluble Propofol Prodrug: In Vivo Evaluation," *Anesth. Analg.* 2002, 95, 1285-1292.
Borgeat et al., "Preliminary Communication: Adjuvant Propofol Enables Better Control of Nausea and Emesid Secondary to Chemotherapy for Breast Cancer," *Can. J. Anaesth.* 1994, 41, 1117-1119.
Borgeat et al., "Propofol Improves Patient Comfort During Cysplatin Chemotherapy," *Oncology* 1993, 50, 456-459.
Briggs et al., "An Adverse Rection to the Administration of Disoprofol (Diprvan)," *Anaesthesia* 1982, 37, 1099-1101.
Brooker et al., "Propofol Maintenance to Reduce Postoperatiove Emesis in Thyroidectomy Patients: A Group Sequential Comparison with Isoflurane/Nitrous Oxide," *Anaesth. Intensive Care* 1998, 26, 625-629.
Brown et al., "Role of Propofol in Refractory Status Epilepticus," *Pharmacother.* 1998, 32, 1053-1059.
Chatterjee et al., "Molecular Mechanism Of The Intestinal Biotin Transport Process," *Am. J. Physiol.* 1999, 277, C605-C613.
Collins et al., "Scanning Mutagenesis Of The Putative Transmembrane Segments Of Kir2.1, An Inward Rectifier Potassium Channel," *Proc. Natl. Acad. Sci.* 1997, 13:5456-5460.

(Continued)

Primary Examiner—Amelia Owens
(74) Attorney, Agent, or Firm—Dorsey & Whitney LLP

(57) ABSTRACT

Prodrugs of propofol, methods of making prodrugs of propofol, pharmaceutical compositions of prodrugs of propofol and methods of using prodrugs of propofol and pharmaceutical compositions thereof to treat or prevent diseases or disorders such as migraine headache pain and post-chemotherapy or post-operative surgery nausea and vomiting are disclosed herein.

12 Claims, No Drawings

OTHER PUBLICATIONS

De la Cruz et al., "The Effect of Propofol on Oxidative Stress in Platelets from Surgical Patients,"*Anesth. Analg.* 1999, 89, 1050-1055.

During et al., "Controlled Release of Dopamine from a Polymeric Brain Implant: In Vivo Characterization," 1989, *Ann. Neurol.* 25:351-356.

Gan et al., "Determination of Plasma Concentrations of Propofol Associated with 50% Reduction in Postoperative Nausea," *Anesthesiology*, 1997, 87, 779-784.

Halestrap et al., "The Proton-Liked Monocarboxylate Transporter (MCT) family: Structure, Function and Regulation," *Biomedical J.*, 1999, 343, 281-299.

Hasan et al., "Comparison of the Effects of the Propofol and Thiopental on the Pattern of Maximal Electroshock Seizures in a Rat," *Pharmacol. Toxicol.* 1994, 74, 50-53.

Hashimotto et al., "Abnormal Activity in the Globus Pallidus in the Off-Period Dystonia," *Annals. of Neurology*, 2001, 49, 242-275.

Holtkamp et al., "Propofol In Subanesthetic Doses Terminates Status Epilepticus In A Rodent Model," *Ann. Neurol.* 2001, 49, 260-263.

Howard et al., "Intercerebral Drug Delivery in Rats with Lesion-Induced Memory Deficits," 1989, *J. Neurosurg.* 71:105-112.

Krusz et al., "Intravenous Propofol: Unique Effectiveness in Treating Intractable Migraine," *Headache* 2000, 40, 224-230.

Kuisma et al., "Propofol in Prehospital Treatment of Convulsive Status Epilepticus," *Epilepsia* 1995, 36, 1241-1243.

Langer et al., "Chemical and Physical Structure of Polymers as Carriers for Controlled Release of Bioactive Agents: A Review," 1983, *J Macromol. Sci. Rev. Macromol Chem.* 23:61.

Langley et al., "Propofol: A Review of Its Pharamcodynamic and Pharmacokinetic Properties and Use as an Intravenous Anaesthetic," *Drugs* 1988, 35, 334-372.

Levy et al., "Inhibition of Calcification of Bioprosthetic Heart Valves by Local Controlled-Release of Diphosphonate," 1985, *Science* 228: 190.

Murphy et al., "The Antioxidant Potential of Propofal (2,6-Diisopropylphenol)," *Br. J. Anaesth.* 1992, 68, 613-618.

Peduto et al., "Biochemical and Electrophysiologic Evidence That Propofol Enchances GABAergic Transmission in the Rat Brain," *Anesthesiology* 1991, 75, 1000-1009.

Phelps et al., "Propolol in Chemotherapy-Associated Nausea and Vomiting," *Ann. Pharmacother.* 1996, 30, 290-292.

Picard et al., "Prevention of Pain on Injection with Propofol: A Quantitative Systematic Review," 2000, 90, 963-969.

Pop et al., "Synthesis and Preliminary Pharmacological Evaluation of Some Chemical Delivery Systems of 2,6-Diisopropylphenol (Propofol),"*Med. Chem. Res.* 1992, 2, 16-21.

Prasad et al., "Molecular and Functional Characterization of the Intestinal Na1-Dependent Multivitamin Transporter," *Arch. Biochem. Biophys.* 1999, 366, 95-106.

Prasad et al., "Cloning and Functional Expression of a cDNA Encoding a Mammalian Sodium-dependent Vitamin Transporter Mediating the Uptake of Pantothenate, Biotin, and Lipoate,"*2J. Biol. Chem.* 1998, 273, 7501-7506.

Raleigh et al., "Pharmacokinetics of Isotretinoin (ISO) in Rats Following Oral Dosing or Aerosol Inhalation," *British J. Cancer*, 1999, 80, Suppl. 2, 96-97.

Raleigh et al., "Searching for the Link Between Hypoxia and Poor Prognoses in Human Tumors," *Proc. Amer. Assoc. Cancer Research Annual Meeting*, 1999, 40, 39.

Raoof et al., "In Vivo Assessment of Intestinal Hepatic, and Pulmonary First Pass Metabolism of Propofol in the Rat," *Pharm. Res.* 1996, 13, 891-895.

Sagara et al., "Propofol Hemisuccinate Protects Neuronal Cells from Oxidative Injury," *J. Neurochem.* 1999, 73, 2524-2530.

Saudek et al., "A Preliminary Trial of the Programmable Implantable Medication System For Insulin Delivery," 1989, *N. Engl. J Med.* 321:574.

Sefton, "Implantable Pumps," *CRC Crit Ref Biomed. Eng.* 1987, 14:201.

Simonian et al., "Oxidative Stress in Neurodegenerative Diseases," Pharmacol. Toxicol. 1996, 36, 83-106.

Sutherland et al., "Propofol and Seizures," *Anaesth. Intensive Care* 1994, 22, 733-737.

Tomioka et al., "Propofol Is Effective in Chemotherapy-Induced Nausea and Vomiting: A Case Report with Quantitative Analysis," *Anesth. Analg.* 1999, 89, 798-799.

Tramer et al., "Proofol Anaesthesia and Postoperative Nausea and Vomiting Quantitative and Systemic Review of Randomized Controlled Studies," *Br. J. Anaesth.* 1997, 78, 247-255.

Trapani et al., "Water-Soluble Salts of Aminoacid Esters of the Anaesthetic Agent Propofol," *Int. J. Pharm.* 1998, 175, 195-204.

Trapani et al., "Propofol Analogues. Synthesis, Relationships Between Structure and Affinity for $GABA_A$ Receptors," *J. Med. Chem.* 1998, 41, 1846-1854.

Verma et al., "Osmotically Controlled Oral Drug Delivery,"*Drug Dev. Ind. Pharm.* 2000, 26:695-708.

Walder et al., "Seizure-like phenomena and propofol," *Neurology* 2002, 58, 1327-1332.

Wang et al. "Propofol reduces infarct size and striatal dopamine accumulation following transient middle cerebral artery occulsion: a microdialysis study," *Eur. J. Pharmacol.* 2002, 452, 303-308.

Wang et al., "Human Placement $NA^+$-dependant Multivitamin Transporter," *J. Biol. Chem.* 1999, 274, 14875-14883.

Young et al., "Propofol Neuroprotection in a Rat Model of Ischaemia Reperfusion Injury," *Eur. J. Anaesthesiol.* 1997, 14, 320-326.

Raleigh, "Pharmacokinetics of Isotreinoin (ISO) in Rats Following Oral Dosing or Aerosol Inhalation," *British Journal of Cancer*, 1999, 96.

* cited by examiner

AROMATIC PRODRUGS OF PROPOFOL, COMPOSITIONS AND USES THEREOF

1. FIELD

Disclosed herein are prodrugs of propofol, methods of making prodrugs of propofol, pharmaceutical compositions of prodrugs of propofol and methods of using prodrugs of propofol and pharmaceutical compositions thereof to treat or prevent diseases or disorders such as migraine headache pain and post-chemotherapy or post-operative surgery nausea and vomiting.

2. BACKGROUND

Propofol (2,6-diisopropylphenol), (1), is a low molecular weight phenol that is widely used as an intravenous sedative-hypnotic agent in the induction and maintenance of anesthesia and/or sedation in mammals. The advantages of propofol as an anesthetic include rapid onset of anesthesia, rapid clearance, and minimal side effects (Langley et al., *Drugs* 1988, 35, 334–372). Propofol may mediate hypnotic effects through interaction with the $GABA_A$ receptor complex, a heterooligomeric ligand-gated chloride ion channel (Peduto et al., *Anesthesiology* 1991, 75, 1000–1009.).

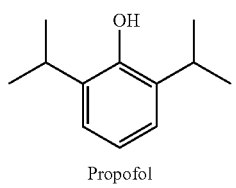

Propofol (1)

Propofol is rapidly metabolized in mammals with the drug being eliminated predominantly as glucuronidated and sulfated conjugates of propofol and 4-hydroxypropofol (Langley et al., *Drugs* 1988, 35, 334–372). Propofol clearance exceeds liver blood flow, which indicates that extrahepatic tissues contribute to the overall metabolism of the drug. Human intestinal mucosa glucuronidates propofol in vitro and oral dosing studies in rats indicate that approximately 90% of the administered drug undergoes first pass metabolism, with extraction by the intestinal mucosa accounting for the bulk of this presystemic elimination (Raoof et al., *Pharm. Res.* 1996, 13, 891–895). Accordingly, oral administration of propofol is of little therapeutic utility because of extensive first-pass metabolism.

Propofol has a broad range of biological and medical applications, which are evident at sub-anesthetic doses and include treatment and/or prevention of intractable migraine headache pain (Krusz et al., *Headache* 2000, 40, 224–230; Krusz, International Publication No. WO 00/54588). Propofol, when used to maintain anesthesia, causes a lower incidence of post-operative nausea and vomiting ("PONV") in comparison to common inhalational anesthetic agents; numerous controlled clinical studies support the anti-emetic activity of propofol (Tramer et al., *Br. J. Anaesth.* 1997, 78, 247–255; Brooker et al., *Anaesth. Intensive Care* 1998, 26, 625–629; Gan et al., *Anesthesiology* 1997, 87, 779–784). Propofol also has anti-emetic activity when used in conjunction with chemotherapeutic compounds (Phelps et al., *Ann. Pharmacother.* 1996, 30, 290–292; Borgeat et al., *Oncology* 1993, 50, 456–459; Borgeat et al., *Can. J. Anaesth.* 1994, 41, 1117–1119; Tomioka et al., *Anesth. Analg.* 1999, 89, 798–799). Nausea, retching and/or vomiting induced by a variety of chemotherapeutic agents (e.g., cisplatin, cyclophosphamide, 5-fluorouracil, methotrexate, anthracycline drugs, etc.) has been controlled by low-dose propofol infusion in patients refractory to prophylaxis with conventional anti-emetic drugs (e.g., serotonin antagonists and corticosteroids).

Propofol may also be used to treat patients with refractory status epilepticus (Brown et al., *Pharmacother.* 1998, 32, 1053–1059; Kuisma et al., *Epilepsia* 1995, 36, 1241–1243; Walder et al., *Neurology* 2002, 58, 1327–1332; Sutherland et al., *Anaesth. Intensive Care* 1994, 22, 733–737). Further, the anticonvulsant effects of propofol have also been demonstrated in rat efficacy models at sub-anesthetic doses (Holtkamp et al., *Ann. Neurol.* 2001, 49, 260–263; Hasan et al., *Pharmacol. Toxicol.* 1994, 74, 50–53).

Propofol may also be used as an antioxidant (Murphy et al., *Br. J. Anaesth.* 1992, 68, 613–618; Sagara et al., *J. Neurochem.* 1999, 73, 2524–2530; Young et al., *Eur. J. Anaesthesiol.* 1997, 14, 320–326; Wang et al. *Eur. J. Pharmacol.* 2002, 452, 303–308). Propofol, at doses typically used for surgical anesthesia, has observable antioxidant effects in humans (De la Cruz et al., *Anesth. Analg.* 1999, 89, 1050–1055). Pathogenesis or subsequent damage pathways in various neurodegenerative diseases involve reactive oxygen species and accordingly may be treated or prevented with antioxidants (Simonian et al., *Pharmacol. Toxicol.* 1996, 36, 83–106). Examples of specific neurodegenerative diseases which may be treated or prevented with antioxidants include, but are not limited to, Friedrich's disease, Parkinson's disease, Alzheimer's disease, Huntington's disease, amyotrophic lateral sclerosis ("ALS"), multiple sclerosis ("MS"), Pick disease, inflammatory diseases and diseases caused by inflammatory mediators such as tumor necrosis factor (TNF) and IL-1.

A significant problem with the therapeutic use of propofol is its lack of appreciable solubility in water. Accordingly, propofol must be specially formulated in aqueous media using solubilizers or emulsifiers (Briggs et al., *Anaesthesia* 1982, 37, 1099–1101). For example, in a current commercial product (Diprivan®, Astra-Zeneca) an oil-in-water emulsion (the emulsifier is the lecithin mixture Intralipid®), is used to formulate propofol (Picard et al., *Anesth. Analg.* 2000, 90, 963–969).

One potential solution to the insolubility of propofol in aqueous solution, which avoids the use of additives, solubilizers or emulsifiers, is a water-soluble, stable propofol prodrug that is converted to propofol in vivo. (Hendler et al., International Publication No. WO 99/58555; Morimoto et al., International Publication No. WO 00/48572; Hendler et al., U.S. Pat. No. 6,254,853; Stella et al., U.S. Patent Application No. US2001/0025035; Hendler, U.S. Pat. No. 6,362,234; International Publication No. WO 02/13810; Sagara et al., *J. Neurochem.* 1999, 73, 2524–2530; Banaszczyk et al., *Anesth. Analg.* 2002, 95, 1285–1292; Trapani et al., *Int. J. Pharm.* 1998, 175, 195–204; Trapani et al., *J. Med. Chem.* 1998, 41, 1846–1854; Anderson et al., *J. Med. Chem.* 2001, 44, 3582–3591; Pop et al., *Med. Chem. Res.* 1992, 2, 16–21). A significant problem with existing propofol prodrugs is their stability under physiological conditions, which prevents release of therapeutically significant concentrations of propofol, particularly when the prodrug is orally administered. Thus, there is a need for propofol prodrugs, which are sufficiently labile under physiological conditions to provide therapeutically significant concentrations of propofol, particularly, when the prodrug is orally administered.

3. SUMMARY

These and other needs are met by providing prodrugs of propofol, methods of making prodrugs of propofol, pharmaceutical compositions of prodrugs of propofol and methods of using prodrugs of propofol and pharmaceutical compositions thereof to treat or prevent diseases or disorders such as migraine headache pain, neurodegenerative disorders and post-chemotherapy or post-operative surgery nausea and vomiting. In some embodiments, prodrugs of propofol and pharmaceutical compositions thereof are orally administered. In other embodiments, prodrugs of propofol are translocated across the gastrointestinal mucosa via interaction with transporter proteins expressed within enterocytes lining the gastrointestinal tract.

In a first aspect, a compound of structural Formula (I) is provided:

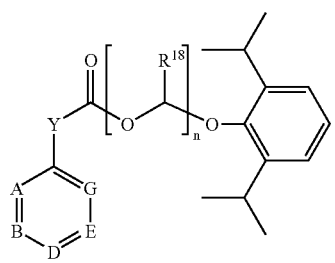

(I)

or pharmaceutically acceptable salts, hydrates, solvates or N-oxides thereof, wherein:

n is 0 or 1;

Y is selected from the group consisting of a bond, $CR^1R^2$, $NR^3$, O and S;

A is $CR^4$ or N;

B is $CR^5$ or N;

D is $CR^6$ or N;

E is $CR^7$ or N;

G is $CR^8$ or N;

$R^{18}$ is selected from the group consisting of hydrogen, alkyl, substituted alkyl, alkoxycarbonyl, aryl, substituted aryl, arylalkyl, carbamoyl, substituted carbamoyl, cycloalkyl, substituted cycloalkyl, cycloheteroalkyl, heteroaryl, substituted heteroaryl and heteroarylalkyl;

$R^1$ and $R^2$ are independently selected from the group consisting of hydrogen, alkyl, substituted alkyl, aryl, substituted aryl, arylalkyl, cycloalkyl, substituted cycloalkyl, cycloheteroalkyl, heteroaryl, substituted heteroaryl and heteroarylalkyl;

$R^3$ is selected from the group consisting of hydrogen, alkyl, substituted alkyl, aryl, arylalkyl, cycloalkyl and heteroaryl;

$R^4$ is selected from the group consisting of hydrogen, alkyl, substituted alkyl, alkoxy, substituted alkoxy, alkoxycarbonyl, aryl, substituted aryl, arylalkyl, carboxyl, cycloalkyl, substituted cycloalkyl, cycloheteroalkyl, halo, heteroaryl, substituted heteroaryl, heteroarylalkyl, hydroxyl and $—W[C(O)]_kZ(CR^9R^{10})_rCO_2R^{11}$;

$R^5$ is selected from the group consisting of hydrogen, alkyl, substituted alkyl, alkoxy, substituted alkoxy, alkoxycarbonyl, aryl, substituted aryl, arylalkyl, carboxyl, cycloalkyl, substituted cycloalkyl, cycloheteroalkyl, halo, heteroaryl, substituted heteroaryl, heteroarylalkyl, hydroxyl and $—W[C(O)]_kZ(CR^9R^{10})_rCO_2R^{11}$;

$R^6$ is selected from the group consisting of hydrogen, alkyl, substituted alkyl, alkoxy, substituted alkoxy, alkoxycarbonyl, aryl, substituted aryl, arylalkyl, carboxyl, cycloalkyl, substituted cycloalkyl, cycloheteroalkyl, halo, heteroaryl, substituted heteroaryl, heteroarylalkyl, hydroxyl and $—W[C(O)]_kZ(CR^9R^{10})_rCO_2R^{11}$;

$R^7$ is selected from the group consisting of hydrogen, alkyl, substituted alkyl, alkoxy, substituted alkoxy, alkoxycarbonyl, aryl, substituted aryl, arylalkyl, carboxyl, cycloalkyl, substituted cycloalkyl, cycloheteroalkyl, halo, heteroaryl, substituted heteroaryl, heteroarylalkyl, hydroxyl and $—W[C(O)]_kZ(CR^9R^{10})_rCO_2R^{11}$;

$R^8$ is selected from the group consisting of hydrogen, alkyl, substituted alkyl, alkoxy, substituted alkoxy, alkoxycarbonyl, aryl, substituted aryl, arylalkyl, carboxyl, cycloalkyl, substituted cycloalkyl, cycloheteroalkyl, halo, heteroaryl, substituted heteroaryl, heteroarylalkyl, hydroxyl and $—W[C(O)]_kZ(CR^9R^{10})_rCO_2R^{11}$;

W is selected from the group consisting of a bond, $CR^{12}R^{13}$, $NR^{14}$, O and S;

Z is selected from the group consisting of $CR^{15}R^{16}$, $NR^{17}$, O and S;

k is 0 or 1;

r is 1, 2 or 3;

each of $R^9$, $R^{10}$, $R^{11}$, $R^{12}$, $R^{13}$, $R^{15}$ and $R^{16}$ is independently selected from the group consisting of hydrogen, alkyl, substituted alkyl, aryl, substituted aryl, arylalkyl, cycloalkyl, substituted cycloalkyl, cycloheteroalkyl, heteroaryl, substituted heteroaryl and heteroarylalkyl;

$R^{14}$ and $R^{17}$ are independently selected from the group consisting of hydrogen, alkyl, substituted alkyl, aryl, arylalkyl, cycloalkyl and heteroaryl;

with the provisos that:

at least one of A, B, D, E and G is not N;

one and only one of $R^4$, $R^5$, $R^6$, $R^7$ or $R^8$ is $—W[C(O)]_kZ(CR^9R^{10})_rCO_2R^{11}$;

and if k is 0 then W is a bond.

In a second aspect pharmaceutical compositions are provided, which generally comprise one or more compounds disclosed herein, and a pharmaceutically acceptable vehicle such as a diluent, carrier, excipient or adjuvant. The choice of diluent, carrier, excipient and adjuvant will depend upon, among other factors, the desired mode of administration. In some embodiments, the mode of administration is oral.

In a third aspect, methods for treating or preventing various diseases or disorders including, but not limited to migraine headache pain, post-chemotherapy or post-operative surgery nausea and vomiting and neurodegenerative disorders (e.g., epilepsy, Friedrich's disease, Parkinson's disease, Alzheimer's disease, Huntington's disease, amyotrophic lateral sclerosis (ALS), multiple sclerosis (MS) and Pick disease) are provided. The methods generally involve administering to a patient in need of such treatment or prevention a therapeutically effective amount of a compound disclosed herein and/or pharmaceutical compositions thereof.

In a fourth aspect, methods for inducing and/or maintaining anesthesia or sedation in a mammal are provided. The methods generally involve administering to a patient in need of such anesthesia sedation induction and/or maintenance a therapeutically effective amount of a compound disclosed herein and/or pharmaceutical compositions thereof.

4. DETAILED DESCRIPTION

4.1 Definitions

"Alkyl" by itself or as part of another substituent refers to a saturated or unsaturated, branched, straight-chain or cyclic monovalent hydrocarbon radical derived by the removal of one hydrogen atom from a single carbon atom of a parent alkane, alkene or alkyne. Typical alkyl groups include, but are not limited to, methyl; ethyls such as ethanyl, ethenyl, ethynyl; propyls such as propan-1-yl, propan-2-yl, cyclopropan-1-yl, prop-1-en-1-yl, prop-1-en-2-yl, prop-2-en-1-yl (allyl), cycloprop-1-en-1-yl; cycloprop-2-en-1-yl, prop-1-yn-1-yl, prop-2-yn-1-yl, etc.; butyls such as butan-1-yl, butan-2-yl, 2-methyl-propan-1-yl, 2-methyl-propan-2-yl, cyclobutan-1-yl, but-1-en-1-yl, but-1-en-2-yl, 2-methyl-prop-1-en-1-yl, but-2-en-1-yl, but-2-en-2-yl, buta-1,3-dien-1-yl, buta-1,3-dien-2-yl, cyclobut-1-en-1-yl, cyclobut-1-en-3-yl, cyclobuta-1,3-dien-1-yl, but-1-yn-1-yl, but-1-yn-3-yl, but-3-yn-1-yl, etc.; and the like.

The term "alkyl" is specifically intended to include groups having any degree or level of saturation, i.e., groups having exclusively single carbon-carbon bonds, groups having one or more double carbon-carbon bonds, groups having one or more triple carbon-carbon bonds and groups having mixtures of single, double and triple carbon-carbon bonds. Where a specific level of saturation is intended, the expressions "alkanyl," "alkenyl," and "alkynyl" are used. In some embodiments, an alkyl group comprises from 1 to 20 carbon atoms. In other embodiments, an alkyl group comprises from 1 to 10 carbon atoms. In still other embodiments, an alkyl group comprises from 1 to 10 carbon atoms.

"Alkanyl" by itself or as part of another substituent refers to a saturated branched, straight-chain or cyclic alkyl radical derived by the removal of one hydrogen atom from a single carbon atom of a parent alkane. Typical alkanyl groups include, but are not limited to, methanyl; ethanyl; propanyls such as propan-1-yl, propan-2-yl (isopropyl), cyclopropan-1-yl, etc.; butanyls such as butan-1-yl, butan-2-yl (sec-butyl), 2-methyl-propan-1-yl (isobutyl), 2-methyl-propan-2-yl (t-butyl), cyclobutan-1-yl, etc.; and the like.

"Alkenyl" by itself or as part of another substituent refers to an unsaturated branched, straight-chain or cyclic alkyl radical having at least one carbon-carbon double bond derived by the removal of one hydrogen atom from a single carbon atom of a parent alkene. The group may be in either the cis or trans conformation about the double bond(s). Typical alkenyl groups include, but are not limited to, ethenyl; propenyls such as prop-1-en-1-yl, prop-1-en-2-yl, prop-2-en-1-yl (allyl), prop-2-en-2-yl, cycloprop-1-en-1-yl; cycloprop-2-en-1-yl; butenyls such as but-1-en-1-yl, but-1-en-2-yl, 2-methyl-prop-1-en-1-yl, but-2-en-1-yl, but-2-en-1-yl, but-2-en-2-yl, buta-1,3-dien-1-yl, buta-1,3-dien-2-yl, cyclobut-1-en-1-yl, cyclobut-1-en-3-yl, cyclobuta-1,3-dien-1-yl, etc.; and the like.

"Alkynyl" by itself or as part of another substituent refers to an unsaturated branched, straight-chain or cyclic alkyl radical having at least one carbon-carbon triple bond derived by the removal of one hydrogen atom from a single carbon atom of a parent alkyne. Typical alkynyl groups include, but are not limited to, ethynyl; propynyls such as prop-1-yn-1-yl, prop-2-yn-1-yl, etc.; butynyls such as but-1-yn-1-yl, but-1-yn-3-yl, but-3-yn-1-yl, etc.; and the like.

"Acyl" by itself or as part of another substituent refers to a radical —C(O)R$^{30}$, where R$^{30}$ is hydrogen, alkyl, cycloalkyl, cycloheteroalkyl, aryl, arylalkyl, heteroalkyl, heteroaryl, heteroarylalkyl as defined herein. Representative examples include, but are not limited to, formyl, acetyl, cyclohexylcarbonyl, cyclohexylmethylcarbonyl, benzoyl, benzylcarbonyl and the like.

"Alkoxy" by itself or as part of another substituent refers to a radical —OR$^{31}$ where R$^{31}$ represents an alkyl or cycloalkyl group as defined herein. Representative examples include, but are not limited to, methoxy, ethoxy, propoxy, butoxy, cyclohexyloxy and the like.

"Alkoxycarbonyl" by itself or as part of another substituent, refers to a radical —C(O)OR$^{31}$ where R$^{31}$ is as defined above.

"Aryl" by itself or as part of another substituent refers to a monovalent aromatic hydrocarbon radical derived by the removal of one hydrogen atom from a single carbon atom of a parent aromatic ring system. Typical aryl groups include, but are not limited to, groups derived from aceanthrylene, acenaphthylene, acephenanthrylene, anthracene, azulene, benzene, chrysene, coronene, fluoranthene, fluorene, hexacene, hexaphene, hexalene, as-indacene, s-indacene, indane, indene, naphthalene, octacene, octaphene, octalene, ovalene, penta-2,4-diene, pentacene, pentalene, pentaphene, perylene, phenalene, phenanthrene, picene, pleiadene, pyrene, pyranthrene, rubicene, triphenylene, trinaphthalene and the like. In some embodiment, an aryl group comprises from 6 to 20 carbon atoms. In other embodiments, and aryl group comprises from 6 to 12 carbon atoms.

"Arylalkyl" by itself or as part of another substituent refers to an acyclic alkyl radical in which one of the hydrogen atoms bonded to a carbon atom, typically a terminal or sp$^3$ carbon atom, is replaced with an aryl group. Typical arylalkyl groups include, but are not limited to, benzyl, 2-phenylethan-1-yl, 2-phenylethen-1-yl, naphthylmethyl, 2-naphthylethan-1-yl, 2-naphthylethen-1-yl, naphthobenzyl, 2-naphthophenylethan-1-yl and the like. Where specific alkyl moieties are intended, the nomenclature arylalkanyl, arylalkenyl and/or arylalkynyl is used. In some embodiments, an arylalkyl group is ($C_6$–$C_{30}$) arylalkyl, e.g., the alkanyl, alkenyl or alkynyl moiety of the arylalkyl group is ($C_1$–$C_{10}$) and the aryl moiety is ($C_6$–$C_{20}$). In other embodiments, an arylalkyl group is ($C_6$–$C_{20}$) arylalkyl, e.g., the alkanyl, alkenyl or alkynyl moiety of the arylalkyl group is ($C_1$–$C_8$) and the aryl moiety is ($C_6$–$C_{12}$).

"Carbamoyl" by itself or as part of another substituent refers to the radical —C(O)N(R$^{32}$)R$^{33}$ where R$^{32}$ and R$^{33}$ are independently hydrogen, alkyl, substituted alkyl, aryl, substituted aryl, arylalkyl, substituted arylalkyl, heteroarylalkyl, substituted heteroarylalkyl, heteroaryl or substituted heteroaryl, as defined herein.

"Compounds" refers to compounds encompassed by the generic formulae disclosed herein and includes any specific compounds within those formulae whose structure is disclosed herein. Compounds may be identified either by their chemical structure and/or chemical name. When the chemical structure and chemical name conflict, the chemical structure is determinative of the identity of the compound. Compounds disclosed herein may contain one or more chiral centers and/or double bonds and therefore, may exist as stereoisomers, such as double-bond isomers (i.e., geometric isomers), enantiomers or diastereomers. Accordingly, when stereochemistry at chiral centers is not specified, the chemical structures depicted herein encompass all possible configurations at those chiral centers including the stereoisomerically pure form (e.g., geometrically pure, enantiomerically pure or diastereomerically pure) and enantiomeric and stereoisomeric mixtures. Enantiomeric and stereoisomeric mixtures can be resolved into their component enantiomers or stereoisomers using separation techniques or chiral synthesis techniques well known to the skilled artisan. Compounds disclosed herein may also exist in several tautomeric forms including the enol form, the keto form and mixtures thereof. Accordingly, the chemical structures depicted herein encompass all possible tautomeric forms of the illustrated compounds. Compounds disclosed herein also include isotopically labeled compounds where one or more atoms have an atomic mass different from the atomic mass conventionally found in nature. Examples of isotopes that may be incorporated into the compounds disclosed herein include, but are not limited to, $^2$H, $^3$H, $^{11}$C, $^{13}$C, $^{14}$C, $^{15}$N, $^{17}$O and $^{18}$O. Compounds disclosed herein may exist in unsolvated forms as well as solvated forms, including hydrated forms and as N-oxides. In general, the hydrated, solvated and N-oxide forms are within the scope of the present disclosure. Certain compounds disclosed herein may exist in multiple crystalline or amorphous forms. In general, all physical forms are equivalent for the uses contemplated herein and are intended to be within the scope of the present disclosure. Further, it should be understood, when partial structures of compounds are illustrated, that brackets indicate the point of attachment of the partial structure to the rest of the molecule.

"Cycloalkyl" by itself or as part of another substituent refers to a saturated or unsaturated cyclic alkyl radical. Where a specific level of saturation is intended, the nomenclature "cycloalkanyl" or "cycloalkenyl" is used. Typical cycloalkyl groups include, but are not limited to, groups derived from cyclopropane, cyclobutane, cyclopentane, cyclohexane, and the like. Preferably, the cycloalkyl group is ($C_3$–$C_{10}$) cycloalkyl, more preferably ($C_3$–$C_7$) cycloalkyl.

"Cycloheteroalkyl" by itself or as part of another substituent refers to a saturated or unsaturated cyclic alkyl radical in which one or more carbon atoms (and any associated hydrogen atoms) are independently replaced with the same or different heteroatom. Typical heteroatoms to replace the carbon atom(s) include, but are not limited to, N, P, O, S, Si, etc. Where a specific level of saturation is intended, the nomenclature "cycloheteroalkanyl" or "cycloheteroalkenyl" is used. Typical cycloheteroalkyl groups include, but are not limited to, groups derived from epoxides, azirines, thiiranes, imidazolidine, morpholine, piperazine, piperidine, pyrazolidine, pyrrolidine, quinuclidine, and the like.

"Heteroalkyl, Heteroalkanyl, Heteroalkenyl and Heteroalkynyl" by themselves or as part of another substituent refer to alkyl, alkanyl, alkenyl and alkynyl groups, respectively, in which one or more of the carbon atoms (and any associated hydrogen atoms) are independently replaced with the same or different heteroatomic groups. Typical heteroatomic groups which can be included in these groups include, but are not limited to, —O—, —S—, —O—O—, —S—S—, —O—S—, —NR$^{34}$R$^{35}$—, =N—N=, —N=N—, —N=N—NR$^{36}$R$^{37}$, —PR$^{38}$—, —P(O)$_2$—, —POR$^{39}$—, —O—P(O)$_2$—, —SO—, —SO$_2$—, —SnR$^{40}$R$^{41}$— and the like, where R$^{34}$, R$^{35}$, R$^{36}$, R$^{37}$, R$^{38}$, R$^{39}$, R$^{40}$ and R$^{41}$ are independently hydrogen, alkyl, substituted alkyl, aryl, substituted aryl, arylalkyl, substituted arylalkyl, cycloalkyl, substituted cycloalkyl, cycloheteroalkyl, substituted cycloheteroalkyl, heteroalkyl, substituted heteroalkyl, heteroaryl, substituted heteroaryl, heteroarylalkyl or substituted heteroarylalkyl.

"Heteroaryl" by itself or as part of another substituent refers to a monovalent heteroaromatic radical derived by the removal of one hydrogen atom from a single atom of a parent heteroaromatic ring system. Typical heteroaryl groups include, but are not limited to, groups derived from acridine, arsindole, carbazole, β-carboline, chromane, chromene, cinnoline, furan, imidazole, indazole, indole, indoline, indolizine, isobenzofuran, isochromene, isoindole, isoindoline, isoquinoline, isothiazole, isoxazole, naphthyridine, oxadiazole, oxazole, perimidine, phenanthridine, phenanthroline, phenazine, phthalazine, pteridine, purine, pyran, pyrazine, pyrazole, pyridazine, pyridine, pyrimidine, pyrrole, pyrrolizine, quinazoline, quinoline, quinolizine, quinoxaline, tetrazole, thiadiazole, thiazole, thiophene, triazole, xanthene, and the like. In some embodiments, the heteroaryl group is from 5–20 membered heteroaryl. In other embodiments, the heteroaryl group is from 5–10 membered heteroaryl. Preferred heteroaryl groups are those derived from thiophene, pyrrole, benzothiophene, benzofuran, indole, pyridine, quinoline, imidazole, oxazole and pyrazine.

"Heteroarylalkyl" by itself or as part of another substituent refers to an acyclic alkyl radical in which one of the hydrogen atoms bonded to a carbon atom, typically a terminal or sp$^3$ carbon atom, is replaced with a heteroaryl group. Where specific alkyl moieties are intended, the nomenclature heteroarylalkanyl, heteroarylalkenyl and/or heteroarylalkynyl is used. In some embodiments, the heteroarylalkyl group is a 6–30 membered heteroarylalkyl, e.g., the alkanyl, alkenyl or alkynyl moiety of the heteroarylalkyl is 1–10 membered and the heteroaryl moiety is a 5–20-membered heteroaryl. In other embodiments, the heteroarylalkyl group is 6–20 membered heteroarylalkyl, e.g., the alkanyl, alkenyl or alkynyl moiety of the heteroarylalkyl is 1–8 membered and the heteroaryl moiety is a 5–12-membered heteroaryl.

"Parent Aromatic Ring System" refers to an unsaturated cyclic or polycyclic ring system having a conjugated π electron system. Specifically included within the definition of "parent aromatic ring system" are fused ring systems in which one or more of the rings are aromatic and one or more of the rings are saturated or unsaturated, such as, for example, fluorene, indane, indene, phenalene, etc. Typical parent aromatic ring systems include, but are not limited to, aceanthrylene, acenaphthylene, acephenanthrylene, anthracene, azulene, benzene, chrysene, coronene, fluoranthene, fluorene, hexacene, hexaphene, hexalene, as-indacene, s-indacene, indane, indene, naphthalene, octacene, octaphene, octalene, ovalene, penta-2,4-diene, pentacene, pentalene, pentaphene, perylene, phenalene, phenanthrene, picene, pleiadene, pyrene, pyranthrene, rubicene, triphenylene, trinaphthalene and the like.

"Parent Heteroaromatic Ring System" refers to a parent aromatic ring system in which one or more carbon atoms (and any associated hydrogen atoms) are independently replaced with the same or different heteroatom. Typical heteroatoms to replace the carbon atoms include, but are not limited to, N, P, O, S, Si, etc. Specifically included within the definition of "parent heteroaromatic ring systems" are fused ring systems in which one or more of the rings are aromatic and one or more of the rings are saturated or unsaturated, such as, for example, arsindole, benzodioxan, benzofuran, chromane, chromene, indole, indoline, xanthene, etc. Typical parent heteroaromatic ring systems include, but are not limited to, arsindole, carbazole, β-carboline, chromane, chromene, cinnoline, furan, imidazole, indazole, indole, indoline, indolizine, isobenzofuran, isochromene, isoindole, isoindoline, isoquinoline, isothiazole, isoxazole, naphthyridine, oxadiazole, oxazole, perimidine, phenanthridine, phenanthroline, phenazine, phthalazine, pteridine, purine, pyran, pyrazine, pyrazole, pyridazine, pyridine, pyrimidine, pyrrole, pyrrolizine, quinazoline, quinoline, quinolizine, quinoxaline, tetrazole, thiadiazole, thiazole, thiophene, triazole, xanthene, and the like.

"Pharmaceutical composition" refers to at least one compound disclosed herein and a pharmaceutically acceptable vehicle, with which the compound is administered to a patient.

"Pharmaceutically acceptable salt" refers to a salt of a compound disclosed herein, which possesses the desired pharmacological activity of the parent compound. Such salts include: (1) acid addition salts, formed with inorganic acids such as hydrochloric acid, hydrobromic acid, sulfuric acid, nitric acid, phosphoric acid, and the like; or formed with organic acids such as acetic acid, propionic acid, hexanoic acid, cyclopentanepropionic acid, glycolic acid, pyruvic acid, lactic acid, malonic acid, succinic acid, malic acid, maleic acid, fumaric acid, tartaric acid, citric acid, benzoic acid, 3-(4-hydroxybenzoyl) benzoic acid, cinnamic acid, mandelic acid, methanesulfonic acid, ethanesulfonic acid, 1,2-ethane-disulfonic acid, 2-hydroxyethanesulfonic acid, benzenesulfonic acid, 4-chlorobenzenesulfonic acid, 2-naphthalenesulfonic acid, 4-toluenesulfonic acid, camphorsulfonic acid, 4-methylbicyclo[2.2.2]-oct-2-ene-1-carboxylic acid, glucoheptonic acid, 3-phenylpropionic acid, trimethylacetic acid, tertiary butylacetic acid, lauryl sulfuric acid, gluconic acid, glutamic acid, hydroxynaphthoic acid, salicylic acid, stearic acid, muconic acid, and the like; or (2) salts formed when an acidic proton present in the parent compound is replaced by a metal ion, e.g., an alkali metal ion, an alkaline earth ion, or an aluminum ion; or coordinates with an organic base such as ethanolamine, diethanolamine, triethanolamine, N-methylglucamine and the like.

"Pharmaceutically acceptable vehicle" refers to a diluent, adjuvant, excipient or carrier with which a compound is administered.

"Patient" includes humans. The terms "human" and "patient" are used interchangeably herein.

"Preventing" or "prevention" refers to a reduction in risk of acquiring a disease or disorder (i.e., causing at least one of the clinical symptoms of the disease not to develop in a patient that may be exposed to or predisposed to the disease but does not yet experience or display symptoms of the disease).

"Prodrug" refers to a derivative of a drug molecule that requires a transformation within the body to release the active drug. Prodrugs are frequently, although not necessarily, pharmacologically inactive until converted to the parent drug. A hydroxyl containing drug may be converted to, for example, to an ester, carbonate, acyloxyalkyl or a sulfonate prodrug, which may be hydrolyzed in vivo to provide the hydroxyl compound. Prodrugs for drugs with functional groups different than those listed above are well known to the skilled artisan.

"Promoiety" refers to a form of protecting group that when used to mask a functional group within a drug molecule converts the drug into a prodrug. Typically, the promoiety will be attached to the drug via bond(s) that are cleaved by enzymatic or non-enzymatic means in vivo.

"Protecting group" refers to a grouping of atoms that when attached to a reactive functional group in a molecule masks, reduces or prevents reactivity of the functional group. Examples of protecting groups can be found in Green et al., "Protective Groups in Organic Chemistry", (Wiley, $2^{nd}$ ed. 1991) and Harrison et al., "Compendium of Synthetic Organic Methods", Vols. 1–8 (John Wiley and Sons, 1971–1996). Representative amino protecting groups include, but are not limited to, formyl, acetyl, trifluoroacetyl, benzyl, benzyloxycarbonyl ("CBz"), tert-butoxycarbonyl ("Boc"), trimethylsilyl ("TMS"), 2-trimethylsilyl-ethanesulfonyl ("SES"), trityl and substituted trityl groups, allyloxycarbonyl, 9-fluorenylmethyloxycarbonyl ("FMOC"), nitro-veratryloxycarbonyl ("NVOC") and the like. Representative hydroxyl protecting groups include, but are not limited to, those where the hydroxyl group is either acylated or alkylated such as benzyl, and trityl ethers as well as alkyl ethers, tetrahydropyranyl ethers, trialkylsilyl ethers and allyl ethers.

"SMVT" refers to the sodium-dependent multivitamin transporter (SLC5A6). Genes encoding this transporter have been cloned from rat, human and rabbit tissue (see Prasad et al., *J. Biol. Chem.* 1998, 273, 7501–7506; Wang et al., *J. Biol. Chem.* 1999, 274, 14875–14883; Chatterjee et al., *Am. J. Physiol.* 1999, 277, C605–C613; Prasad et al., *Arch. Biochem. Biophys.* 1999, 366, 95–106).

"Substituted" refers to a group in which one or more hydrogen atoms are independently replaced with the same or different substituent(s). Typical substituents include, but are not limited to, -M, $-R^{60}$, $-O^-$, $=O$, $-OR^{60}$, $-SR^{60}$, $-S^-$, $=S$, $-NR^{60}R^{61}$, $=NR^{60}$, $-CF_3$, $-CN$, $-OCN$, $-SCN$, $-NO$, $-NO_2$, $=N_2$, $-N_3$, $-S(O)_2O^-$, $-S(O)_2OH$, $-S(O)_2R^{60}$, $-OS(O_2)O^-$, $-OS(O)_2R^{60}$, $-P(O)(O^-)_2$, $-P(O)(OR^{60})(O^-)$, $-OP(O)(OR^{60})(OR^{61})$, $-C(O)R^{60}$, $-C(S)R^{60}$, $-C(O)OR^{60}$, $-C(O)NR^{60}R^{61}$, $-C(O)O^-$, $-C(S)OR^{60}$, $-NR^{62}C(O)NR^{60}R^{61}$, $-NR^{62}C(S)NR^{60}R^{61}$, $-NR^{62}C(NR^{63})NR^{60}R^{61}$ and $-C(NR^{62})NR^{60}R^{61}$ where M is independently a halogen; $R^{60}$, $R^{61}$, $R^{62}$ and $R^{63}$ are independently hydrogen, alkyl, substituted alkyl, alkoxy, substituted alkoxy, cycloalkyl, substituted cycloalkyl, cycloheteroalkyl, substituted cycloheteroalkyl, aryl, substituted aryl, heteroaryl or substituted heteroaryl, or optionally $R^{60}$ and $R^{61}$ together with the nitrogen atom to which they are bonded form a cycloheteroalkyl or substituted cycloheteroalkyl ring; and $R^{64}$ and $R^{65}$ are independently hydrogen, alkyl, substituted alkyl, aryl, cycloalkyl, substituted cycloalkyl, cycloheteroalkyl, substituted cycloheteroalkyl, aryl, substituted aryl, heteroaryl or substituted heteroaryl, or optionally $R^{64}$ and $R^{65}$ together with the nitrogen atom to which they are bonded form a cycloheteroalkyl or substituted cycloheteroalkyl ring. Preferably, substituents include -M, $-R^{60}$, $=O$, $-OR^{60}$, $-SR^{60}$, $-S^-$, $=S$, $-NR^{60}R^{61}$, $=NR^{60}$, $-CF_3$, $-CN$, $-OCN$, $-SCN$, $-NO$, $-NO_2$, $=N_2$, $-N_3$, $-S(O)_2R^{60}$, $-OS(O_2)O^-$, $-OS(O)_2R^{60}$, $-P(O)(O^-)_2$, $-P(O)(OR^{60})(O^-)$, $-OP(O)(OR^{60})(OR^{61})$, $-C(O)R^{60}$, $-C(S)R^{60}$, $-C(O)OR^{60}$, $-C(O)NR^{60}R^{61}$, $-C(O)O^-$, $-NR^{62}C(O)NR^{60}R^{61}$, more preferably, -M, $-R^{60}$, $=O$, $-OR^{60}$, $-SR^{60}$, $-NR^{60}R^{61}$, $-CF_3$, $-CN$, $-NO_2$, $-S(O)_2R^{60}$, $-P(O)(OR^{60})(OR^-)$, $-OP(O)(OR^{60})(OR^{61})$, $-C(O)R^{60}$, $-C(O)OR^{60}$, $-C(O)NR^{60}R^{61}$, $-C(O)O^-$, most preferably, -M, $-R^{60}$, $=O$, $-OR^{60}$, $-SR^{60}$, $-NR^{60}R^{61}$, $-CF_3$, $-CN$, $-NO_2$, $-S(O)_2R^{60}$, $-OP(O)(OR^{60})(OR^{61})$, $-C(O)R^{60}$, $-C(O)OR^{60}$, $-C(O)O^-$, where $R^{60}$, $R^{61}$ and $R^{62}$ are as defined above.

"Transported by the SMVT transporter" refers to the translocation of a molecule across a membrane of a cell expressing the SMVT transporter. The translocation occurs through interaction with the transporter and is energized by cotransport of Na$^+$ ions across the membrane.

"Treating" or "treatment" of any disease or disorder refers, In some embodiments, to ameliorating the disease or disorder (i.e., arresting or reducing the development of the disease or at least one of the clinical symptoms thereof). In other embodiments "treating" or "treatment" refers to ameliorating at least one physical parameter, which may not be discernible by the patient. In yet another embodiment, "treating" or "treatment" refers to inhibiting the disease or disorder, either physically, (e.g., stabilization of a discernible symptom), physiologically, (e.g., stabilization of a physical parameter), or both. In yet another embodiment, "treating" or "treatment" refers to delaying the onset of the disease or disorder.

"Therapeutically effective amount" means the amount of a compound that, when administered to a patient for treating a disease, is sufficient to effect such treatment for the disease. The "therapeutically effective amount" will vary depending on the compound, the disease and its severity and the age, weight, etc., of the patient to be treated.

Reference will now be made in detail to various embodiments of the invention. While the invention will be described in conjunction with these embodiments, it will be understood that it is not intended to limit the invention to those embodiments. To the contrary, it is intended to cover alternatives, modifications, and equivalents as may be included within the spirit and scope of the invention as defined by the appended claims.

5.2 Compounds

The compounds disclosed herein are prodrugs of propofol. In some embodiments, the compounds are orally administered. In some embodiments, the compounds are able to pass across the gastrointestinal tract. In other embodiments, prodrugs of propofol are translocated across the gastrointestinal mucosa via interaction with transporter proteins expressed within enterocytes lining the gastrointestinal tract.

In some embodiments, compounds of structural Formula (I) are provided:

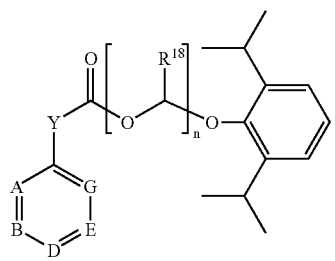

(I)

or pharmaceutically acceptable salts, hydrates, solvates or N-oxides thereof, wherein:

n is 0 or 1;

Y is selected from the group consisting of a bond, $CR^1R^2$, $NR^3$, O and S;

A is $CR^4$ or N;

B is $CR^5$ or N;

D is $CR^6$ or N;

E is $CR^7$ or N;

G is $CR^8$ or N;

$R^{18}$ is selected from the group consisting of hydrogen, alkyl, substituted alkyl, alkoxycarbonyl, aryl, substituted aryl, arylalkyl, carbamoyl, substituted carbamoyl, cycloalkyl, substituted cycloalkyl, cycloheteroalkyl, heteroaryl, substituted heteroaryl and heteroarylalkyl;

$R^1$ and $R^2$ are independently selected from the group consisting of hydrogen, alkyl, substituted alkyl, aryl, substituted aryl, arylalkyl, cycloalkyl, substituted cycloalkyl, cycloheteroalkyl, heteroaryl, substituted heteroaryl and heteroarylalkyl;

$R^3$ is selected from the group consisting of hydrogen, alkyl, substituted alkyl, aryl, arylalkyl, cycloalkyl and heteroaryl;

$R^4$ is selected from the group consisting of hydrogen, alkyl, substituted alkyl, alkoxy, substituted alkoxy, alkoxycarbonyl, aryl, substituted aryl, arylalkyl, carboxyl, cycloalkyl, substituted cycloalkyl, cycloheteroalkyl, halo, heteroaryl, substituted heteroaryl, heteroarylalkyl, hydroxyl and —$W[C(O)]_kZ(CR^9R^{10})_rCO_2R^{11}$;

$R^5$ is selected from the group consisting of hydrogen, alkyl, substituted alkyl, alkoxy, substituted alkoxy, alkoxycarbonyl, aryl, substituted aryl, arylalkyl, carboxyl, cycloalkyl, substituted cycloalkyl, cycloheteroalkyl, halo, heteroaryl, substituted heteroaryl, heteroarylalkyl, hydroxyl and —$W[C(O)]_kZ(CR^9R^{10})_rCO_2R^{11}$;

$R^6$ is selected from the group consisting of hydrogen, alkyl, substituted alkyl, alkoxy, substituted alkoxy, alkoxycarbonyl, aryl, substituted aryl, arylalkyl, carboxyl, cycloalkyl, substituted cycloalkyl, cycloheteroalkyl, halo, heteroaryl, substituted heteroaryl, heteroarylalkyl, hydroxyl and —$W[C(O)]_kZ(CR^9R^{10})_rCO_2R^{11}$;

$R^7$ is selected from the group consisting of hydrogen, alkyl, substituted alkyl, alkoxy, substituted alkoxy, alkoxycarbonyl, aryl, substituted aryl, arylalkyl, carboxyl, cycloalkyl, substituted cycloalkyl, cycloheteroalkyl, halo, heteroaryl, substituted heteroaryl, heteroarylalkyl, hydroxyl and —$W[C(O)]_kZ(CR^9R^{10})_rCO_2R^{11}$;

$R^8$ is selected from the group consisting of hydrogen, alkyl, substituted alkyl, alkoxy, substituted alkoxy, alkoxycarbonyl, aryl, substituted aryl, arylalkyl, carboxyl, cycloalkyl, substituted cycloalkyl, cycloheteroalkyl, halo, heteroaryl, substituted heteroaryl, heteroarylalkyl, hydroxyl and —$W[C(O)]_kZ(CR^9R^{10})_rCO_2R^{11}$;

W is selected from the group consisting of a bond, $CR^{12}R^{13}$, $NR^{14}$, O and S;

Z is selected from the group consisting of $CR^{15}R^{16}$, $NR^{17}$, O and S;

k is 0 or 1;

r is 1, 2 or 3;

each of $R^9$, $R^{10}$, $R^{11}$, $R^{12}$, $R^{13}$, $R^{15}$ and $R^{16}$ is independently selected from the group consisting of hydrogen, alkyl, substituted alkyl, aryl, substituted aryl, arylalkyl, cycloalkyl, substituted cycloalkyl, cycloheteroalkyl, heteroaryl, substituted heteroaryl and heteroarylalkyl;

$R^{14}$ and $R^{17}$ are independently selected from the group consisting of hydrogen, alkyl, substituted alkyl, aryl, arylalkyl, cycloalkyl and heteroaryl;

with the provisos that:

at least one of A, B, D, E and G is not N;

one and only one of $R^4$, $R^5$, $R^6$, $R^7$ or $R^8$ is —$W[C(O)]_kZ(CR^9R^{10})_rCO_2R^{11}$;

and if k is 0 then W is a bond.

In some embodiments of a compound of Formula (I), n is 0. In other embodiments of a compound of Formula (I), n is 1.

In still other embodiments of a compound of Formula (I), n is 1 and $R^{18}$ is selected from the group consisting of hydrogen, alkyl, substituted alkyl, aryl, substituted aryl, arylalkyl, cycloalkyl and heteroaryl.

In the above embodiment, $R^{18}$ is selected from the group consisting of hydrogen, alkyl and substituted alkyl. Preferably, $R^{18}$ is selected from the group consisting of hydrogen and $C_{1-4}$ alkyl. More preferably, $R^{18}$ is hydrogen or methyl.

In the above embodiment, $R^{18}$ is selected from the group consisting of hydrogen, aryl and substituted aryl. Preferably, $R^{18}$ is selected from the group consisting of hydrogen, phenyl and substituted phenyl.

In the above embodiment, $R^{18}$ is selected from the group consisting of hydrogen, arylalkyl and substituted arylalkyl.

Preferably, $R^{18}$ is selected from the group consisting of hydrogen, benzyl and substituted benzyl.

In still other embodiments of a compound of Formula (I), Y is a bond.

In still other embodiments of a compound of Formula (I), Y is $CR^1R^2$ and $R^1$ and $R^2$ are independently selected from the group consisting of hydrogen, alkyl, substituted alkyl, aryl, arylalkyl, cycloalkyl and heteroaryl. Preferably, $R^1$ and $R^2$ are independently hydrogen or alkanyl. More preferably, $R^1$ and $R^2$ are independently hydrogen or methyl.

In still other embodiments of a compound of Formula (I), Y is $NR^3$ and $R^3$ is hydrogen or alkanyl. More preferably, $R^3$ is hydrogen or methyl.

In still other embodiments of a compound of Formula (I), Y is O.

In still other embodiments of a compound of Formula (I), Y is S.

In still other embodiments of a compound of Formula (I), A is $CR^4$. Preferably, $R^4$ is selected from the group consisting of hydrogen, $C_{1-4}$ alkyl, $C_{1-4}$ alkoxy, $C_{1-4}$ alkoxycarbonyl, carboxyl, halo, hydroxyl and —$W[C(O)]_kZ(CR^9R^{10})_rCO_2R^{11}$. More preferably, $R^4$ is hydrogen, $C_{1-4}$ alkyl or —$W[C(O)]_kZ(CR^9R^{10})_rCO_2R^{11}$. Preferably, $R^4$ is —$W[C(O)]_kZ(CR^9R^{10})_rCO_2R^{11}$ and each of $R^9$, $R^{10}$, $R^{11}$, $R^{12}$, $R^{13}$, $R^{14}$, $R^{15}$, $R^{16}$ and $R^{17}$ is independently selected from the group consisting of hydrogen, alkyl, substituted alkyl, aryl, arylalkyl, cycloalkyl and heteroaryl. Preferably, $R^9$, $R^{10}$, $R^{12}$, $R^{13}$, $R^{14}$, $R^{15}$, $R^{16}$ and $R^{17}$ are independently hydrogen or alkyl, and $R^{11}$ is selected from the group consisting of hydrogen, $C_{1-4}$ alkyl, phenyl, substituted phenyl, benzyl and substituted benzyl. More preferably, $R^9$, $R^{10}$, $R^{12}$, $R^{13}$, $R^{14}$, $R^{15}$, $R^{16}$ and $R^{17}$ are independently hydrogen or $C_{1-4}$ alkyl, and $R^{11}$ is hydrogen.

In still other embodiments of a compound of Formula (I), A is N.

In still embodiment of a compound of Formula (I), B is $CR^5$. Preferably, $R^5$ is selected from the group consisting of hydrogen, $C_{1-4}$ alkyl, $C_{1-4}$ alkoxy, $C_{1-4}$ alkoxycarbonyl, carboxyl, halo, hydroxyl and —$W[C(O)]_kZ(CR^9R^{10})_rCO_2R^{11}$. More preferably, $R^5$ is hydrogen, $C_{1-4}$ alkyl or —$W[C(O)]_kZ(CR^9R^{10})_rCO_2R^{11}$. Preferably, $R^5$ is —$W[C(O)]_kZ(CR^9R^{10})_rCO_2R^{11}$ and each of $R^9$, $R^{10}$, $R^{11}$, $R^{12}$, $R^{13}$, $R^{14}$, $R^{15}$, $R^{16}$ and $R^{17}$ is independently selected from the group consisting of hydrogen, alkyl, substituted alkyl, aryl, arylalkyl, cycloalkyl and heteroaryl. Preferably, $R^9$, $R^{10}$, $R^{12}$, $R^{13}$, $R^{14}$, $R^{15}$, $R^{16}$ and $R^{17}$ are independently hydrogen or alkyl, and $R^{11}$ is selected from the group consisting of hydrogen, $C_{1-4}$ alkyl, phenyl, substituted phenyl, benzyl and substituted benzyl. More preferably, $R^9$, $R^{10}$, $R^{12}$, $R^{13}$, $R^{14}$, $R^{15}$, $R^{16}$ and $R^{17}$ are independently hydrogen or $C_{1-4}$ alkyl, and $R^{11}$ is hydrogen.

In still other embodiments of a compound of Formula (I), B is N.

In still other embodiments of a compound of Formula (I), D is $CR^6$. Preferably, $R^6$ is selected from the group consisting of hydrogen, $C_{1-4}$ alkyl, $C_{1-4}$ alkoxy, $C_{1-4}$ alkoxycarbonyl, carboxyl, halo, hydroxyl and —$W[C(O)]_kZ(CR^9R^{10})_rCO_2R^{11}$. More preferably, $R^6$ is hydrogen, $C_{1-4}$ alkyl or —$W[C(O)]_kZ(CR^9R^{10})_rCO_2R^{11}$. Preferably, $R^6$ is —$W[C(O)]_kZ(CR^9R^{10})_rCO_2R^{11}$ and each of $R^9$, $R^{10}$, $R^{11}$, $R^{12}$, $R^{13}$, $R^{14}$, $R^{15}$, $R^{16}$ and $R^{17}$ is independently selected from the group consisting of hydrogen, alkyl, substituted alkyl, aryl, arylalkyl, cycloalkyl and heteroaryl. Preferably, $R^9$, $R^{10}$, $R^{12}$, $R^{13}$, $R^{14}$, $R^{15}$, $R^{16}$ and $R^{17}$ are independently hydrogen or alkyl, and $R^{11}$ is selected from the group consisting of hydrogen, $C_{1-4}$ alkyl, phenyl, substituted phenyl, benzyl and substituted benzyl. More preferably, $R^9$, $R^{10}$, $R^{12}$, $R^{13}$, $R^{14}$, $R^{15}$, $R^{16}$ and $R^{17}$ are independently hydrogen or $C_{1-4}$ alkyl, and $R^{11}$ is hydrogen.

In still other embodiments of a compound of Formula (I), D is N.

In still other embodiments of a compound of Formula (I), E is $CR^7$. Preferably, $R^7$ is selected from the group consisting of hydrogen, $C_{1-4}$ alkyl, $C_{1-4}$ alkoxy, $C_{1-4}$ alkoxycarbonyl, carboxyl, halo, hydroxyl and —$W[C(O)]_kZ(CR^9R^{10})_rCO_2R^{11}$. More preferably, $R^7$ is hydrogen, $C_{1-4}$ alkyl or —$W[C(O)]_kZ(CR^9R^{10})_rCO_2R^{11}$. Preferably, $R^7$ is —$W[C(O)]_kZ(CR^9R^{10})_rCO_2R^{11}$ and each of $R^9$, $R^{10}$, $R^{11}$, $R^{12}$, $R^{13}$, $R^{14}$, $R^{15}$, $R^{16}$ and $R^{17}$ is independently selected from the group consisting of hydrogen, alkyl, substituted alkyl, aryl, arylalkyl, cycloalkyl and heteroaryl. Preferably, $R^9$, $R^{10}$, $R^{12}$, $R^{13}$, $R^{14}$, $R^{15}$, $R^{16}$ and $R^{17}$ are independently hydrogen or alkyl, and $R^{11}$ is selected from the group consisting of hydrogen, $C_{1-4}$ alkyl, phenyl, substituted phenyl, benzyl and substituted benzyl. More preferably, $R^9$, $R^{10}$, $R^{12}$, $R^{13}$, $R^{14}$, $R^{15}$, $R^{16}$ and $R^{17}$ are independently hydrogen or $C_{1-4}$ alkyl, and $R^{11}$ is hydrogen.

In still other embodiments of a compound of Formula (I), E is N.

In still other embodiments of a compound of Formula (I), G is $CR^8$. Preferably, $R^8$ is selected from the group consisting of hydrogen, $C_{1-4}$ alkyl, $C_{1-4}$ alkoxy, $C_{1-4}$ alkoxycarbonyl, carboxyl, halo, hydroxyl and —$W[C(O)]_kZ(CR^9R^{10})_rCO_2R^{11}$. More preferably, $R^8$ is hydrogen, $C_{1-4}$ alkyl or —$W[C(O)]_kZ(CR^9R^{10})_rCO_2R^{11}$. Preferably, $R^8$ is —$W[C(O)]_kZ(CR^9R^{10})_rCO_2R^{11}$ and each of $R^9$, $R^{10}$, $R^{11}$, $R^{12}$, $R^{13}$, $R^{14}$, $R^{15}$, $R^{16}$ and $R^{17}$ is independently selected from the group consisting of hydrogen, alkyl, substituted alkyl, aryl, arylalkyl, cycloalkyl and heteroaryl. Preferably, $R^9$, $R^{10}$, $R^{12}$, $R^{13}$, $R^{14}$, $R^{15}$, $R^{16}$ and $R^{17}$ are independently hydrogen or alkyl, and $R^{11}$ is selected from the group consisting of hydrogen, $C_{1-4}$ alkyl, phenyl, substituted phenyl, benzyl and substituted benzyl. More preferably, $R^9$, $R^{10}$, $R^{12}$, $R^{13}$, $R^{14}$, $R^{15}$, $R^{16}$ and $R^{17}$ are independently hydrogen or $C_{1-4}$ alkyl, and $R^{11}$ is hydrogen.

In still other embodiments of a compound of Formula (I), G is N.

In still other embodiments of a compound of Formula (I), n is 0, Y is a bond, A is $CR^4$, B is $CR^5$, D is $CR^6$, E is $CR^7$, G is $CR^8$, $R^4$ is —$W[C(O)]_kZ(CR^9R^{10})_rCO_2R^{11}$, each of $R^5$, $R^6$, $R^7$ and $R^8$ is independently hydrogen, $C_{1-4}$ alkyl, $C_{1-4}$ alkoxy, $C_{1-4}$ alkoxycarbonyl, carboxyl, halo or hydroxyl and each of $R^9$, $R^{10}$, $R^{11}$, $R^{12}$, $R^{13}$, $R^{14}$, $R^{15}$, $R^{16}$ and $R^{17}$ is independently hydrogen or alkyl. Preferably, each of $R^5$, $R^6$, $R^7$ and $R^8$ is independently hydrogen or $C_{1-4}$ alkyl. More preferably, $R^5$, $R^6$, $R^7$ and $R^8$ are hydrogen. Preferably, each of $R^9$, $R^{10}$, $R^{11}$, $R^{12}$, $R^{13}$, $R^{14}$, $R^{15}$, $R^{16}$ and $R^{17}$ is independently hydrogen or $C_{1-4}$ alkyl.

In still other embodiments of a compound of Formula (I), n is 0, Y is a bond, A is $CR^4$, B is $CR^5$, D is $CR^6$, E is $CR^7$, G is $CR^8$, $R^4$ is —$W[C(O)]_kZ(CR^9R^{10})_rCO_2R^{11}$, each of $R^5$, $R^6$, $R^7$ and $R^8$ is independently hydrogen, $C_{1-4}$ alkyl, $C_{1-4}$ alkoxy, $C_{1-4}$ alkoxycarbonyl, carboxyl, halo or hydroxyl, W is a bond, k is 1, Z is $NR^{17}$, r is 1, and each of $R^9$, $R^{10}$, $R^{11}$ and $R^{17}$ is independently hydrogen or $C_{1-4}$ alkyl. Preferably, each of $R^5$, $R^6$, $R^7$ and $R^8$ is independently hydrogen or $C_{1-4}$ alkyl. More preferably, $R^5$, $R^6$, $R^7$ and $R^8$ are hydrogen. Preferably, $R^{11}$ and $R^{17}$ are hydrogen.

In still other embodiments of a compound of Formula (I), n is 0, Y is a bond, A is $CR^4$, B is $CR^5$, D is $CR^6$, E is $CR^7$, G is $CR^8$, $R^4$ is —$W[C(O)]_kZ(CR^9R^{10})_rCO_2R^{11}$, each of $R^5$, $R^6$, $R^7$ and $R^8$ is independently hydrogen, $C_{1-4}$ alkyl, $C_{1-4}$ alkoxy, $C_{1-4}$ alkoxycarbonyl, carboxyl, halo or hydroxyl, W is a bond, k is 1, Z is $NR^{17}$, r is 2, and each of $R^9$, $R^{10}$, $R^{11}$ and $R^{17}$ is independently hydrogen or $C_{1-4}$ alkyl. Preferably, each of $R^5$, $R^6$, $R^7$ and $R^8$ is independently hydrogen or $C_{1-4}$ alkyl. More preferably, $R^5$, $R^6$, $R^7$ and $R^8$ are hydrogen. Preferably, $R^{11}$ and $R^{17}$ are hydrogen.

In still other embodiments of a compound of Formula (I), n is 0, Y is a bond, A is $CR^4$, B is $CR^5$, D is $CR^6$, E is $CR^7$, G is $CR^8$, $R^4$ is —$W[C(O)]_kZ(CR^9R^{10})_rCO_2R^{11}$, each of $R^5$, $R^6$, $R^7$ and $R^8$ is independently hydrogen, $C_{1-4}$ alkyl, $C_{1-4}$ alkoxy, $C_{1-4}$ alkoxycarbonyl, carboxyl, halo or hydroxyl, W is a bond, k is 1, Z is O, r is 1, and each of $R^9$, $R^{10}$ and $R^{11}$ is independently hydrogen or $C_{1-4}$ alkyl. Preferably, each of $R^5$, $R^6$, $R^7$ and $R^8$ is independently hydrogen or $C_{1-4}$ alkyl. More preferably, $R^5$, $R^6$, $R^7$ and $R^8$ are hydrogen. Preferably, $R^{11}$ is hydrogen.

In still other embodiments of a compound of Formula (I), n is 0, Y is a bond, A is $CR^4$, B is $CR^5$, D is $CR^6$, E is $CR^7$, G is $CR^8$, $R^4$ is —$W[C(O)]_kZ(CR^9R^{10})_rCO_2R^{11}$, each of $R^5$, $R^6$, $R^7$ and $R^8$ is independently hydrogen, $C_{1-4}$ alkyl, $C_{1-4}$ alkoxy, $C_{1-4}$ alkoxycarbonyl, carboxyl, halo or hydroxyl, W is a bond, k is 1, Z is O, r is 2, and each of $R^9$, $R^{10}$ and $R^{11}$ is independently hydrogen or $C_{1-4}$ alkyl. Preferably, each of $R^5$, $R^6$, $R^7$ and $R^8$ is independently hydrogen or $C_{1-4}$ alkyl. More preferably, $R^5$, $R^6$, $R^7$ and $R^8$ are hydrogen. Preferably, $R^{11}$ is hydrogen.

In still other embodiments of a compound of Formula (I), n is 0, Y is a bond, A is $CR^4$, B is $CR^5$, D is $CR^6$, E is $CR^7$, G is $CR^8$, $R^4$ is —$W[C(O)]_kZ(CR^9R^{10})_rCO_2R^{11}$, each of $R^5$, $R^6$, $R^7$ and $R^8$ is independently hydrogen, $C_{1-4}$ alkyl, $C_{1-4}$ alkoxy, $C_{1-4}$ alkoxycarbonyl, carboxyl, halo or hydroxyl, W is O, k is 1, Z is $NR^{17}$, r is 1, and each of $R^9$, $R^{10}$, $R^{11}$ and $R^{17}$ is independently hydrogen or $C_{1-4}$ alkyl. Preferably, each of $R^5$, $R^6$, $R^7$ and $R^8$ is independently hydrogen or $C_{1-4}$ alkyl. More preferably, $R^5$, $R^6$, $R^7$ and $R^8$ are hydrogen. Preferably, $R^{11}$ and $R^{17}$ are hydrogen.

In still other embodiments of a compound of Formula (I), n is 0, Y is a bond, A is $CR^4$, B is $CR^5$, D is $CR^6$, E is $CR^7$, G is $CR^8$, $R^4$ is —$W[C(O)]_kZ(CR^9R^{10})_rCO_2R^{11}$, each of $R^5$, $R^6$, $R^7$ and $R^8$ is independently hydrogen, $C_{1-4}$ alkyl, $C_{1-4}$ alkoxy, $C_{1-4}$ alkoxycarbonyl, carboxyl, halo or hydroxyl, W is O, k is 1, Z is $NR^{17}$, r is 2 and each of $R^9$, $R^{10}$, $R^{11}$ and $R^{17}$ is independently hydrogen or $C_{1-4}$ alkyl. Preferably, each of $R^5$, $R^6$, $R^7$ and $R^8$ is independently hydrogen or $C_{1-4}$ alkyl. More preferably, $R^5$, $R^6$, $R^7$ and $R^8$ are hydrogen. Preferably, $R^{11}$ and $R^{17}$ are hydrogen.

In still other embodiments of a compound of Formula (I), n is 0, Y is a bond, A is $CR^4$, B is $CR^5$, D is $CR^6$, E is $CR^7$, G is $CR^8$, $R^4$ is —$W[C(O)]_kZ(CR^9R^{10})_rCO_2R^{11}$, each of $R^5$, $R^6$, $R^7$ and $R^8$ is independently hydrogen, $C_{1-4}$ alkyl, $C_{1-4}$ alkoxy, $C_{1-4}$ alkoxycarbonyl, carboxyl, halo or hydroxyl, W is O, k is 1, Z is O, r is 1, and each of $R^9$, $R^{10}$ and $R^{11}$ is independently hydrogen or $C_{1-4}$ alkyl. Preferably, each of $R^5$, $R^6$, $R^7$ and $R^8$ is independently hydrogen or $C_{1-4}$ alkyl. More preferably, $R^5$, $R^6$, $R^7$ and $R^8$ are hydrogen. Preferably, $R^{11}$ is hydrogen.

In still other embodiments of a compound of Formula (I), n is 0, Y is a bond, A is $CR^4$, B is $CR^5$, D is $CR^6$, E is $CR^7$, G is $CR^8$, $R^4$ is —$W[C(O)]_kZ(CR^9R^{10})_rCO_2R^{11}$, each of $R^5$, $R^6$, $R^7$ and $R^8$ is independently hydrogen, $C_{1-4}$ alkyl, $C_{1-4}$ alkoxy, $C_{1-4}$ alkoxycarbonyl, carboxyl, halo or hydroxyl, W is O, k is 1, Z is O, r is 2, and each of $R^9$, $R^{10}$ and $R^{11}$ is independently hydrogen or $C_{1-4}$ alkyl. Preferably, each of $R^5$, $R^6$, $R^7$ and $R^8$ is independently hydrogen or $C_{1-4}$ alkyl. More preferably, $R^5$, $R^6$, $R^7$ and $R^8$ are hydrogen. Preferably, $R^{11}$ is hydrogen.

In still other embodiments of a compound of Formula (I), n is 0, Y is a bond, A is $CR^4$, B is $CR^5$, D is $CR^6$, E is $CR^7$, G is $CR^8$, $R^4$ is —$W[C(O)]_kZ(CR^9R^{10})_rCO_2R^{11}$, each of $R^5$, $R^6$, $R^7$ and $R^8$ is independently hydrogen, $C_{1-4}$ alkyl, $C_{1-4}$ alkoxy, $C_{1-4}$ alkoxycarbonyl, carboxyl, halo or hydroxyl, W is O, k is 1, Z is $CR^{15}R^{16}$, r is 1, and each of $R^9$, $R^{10}$, $R^{11}$, $R^{15}$ and $R^{16}$ is independently hydrogen or $C_{1-4}$ alkyl. Preferably, each of $R^5$, $R^6$, $R^7$ and $R^8$ is independently hydrogen or $C_{1-4}$ alkyl. More preferably, $R^5$, $R^6$, $R^7$ and $R^8$ are hydrogen. Preferably, $R^{11}$, $R^{15}$ and $R^{16}$ are hydrogen.

In still other embodiments of a compound of Formula (I), n is 0, Y is a bond, A is $CR^4$, B is $CR^5$, D is $CR^6$, E is $CR^7$, G is $CR^8$, $R^4$ is —$W[C(O)]_kZ(CR^9R^{10})_rCO_2R^{11}$, each of $R^5$, $R^6$, $R^7$ and $R^8$ is independently hydrogen, $C_{1-4}$ alkyl, $C_{1-4}$ alkoxy, $C_{1-4}$ alkoxycarbonyl, carboxyl, halo or hydroxyl, W is O, k is 1, Z is $CR^{15}R^{16}$, r is 2, and each of $R^9$, $R^{10}$, $R^{11}$, $R^{15}$ and $R^{16}$ is independently hydrogen or $C_{1-4}$ alkyl. Preferably, each of $R^5$, $R^6$, $R^7$ and $R^8$ is independently hydrogen or $C_{1-4}$ alkyl. More preferably, $R^5$, $R^6$, $R^7$ and $R^8$ are hydrogen. Preferably, $R^{11}$, $R^{15}$ and $R^{16}$ are hydrogen.

In still other embodiments of a compound of Formula (I), n is 0, Y is a bond, A is $CR^4$, B is $CR^5$, D is $CR^6$, E is $CR^7$, G is $CR^8$, $R^4$ is —$W[C(O)]_kZ(CR^9R^{10})_rCO_2R^{11}$, each of $R^5$, $R^6$, $R^7$ and $R^8$ is independently hydrogen, $C_{1-4}$ alkyl, $C_{1-4}$ alkoxy, $C_{1-4}$ alkoxycarbonyl, carboxyl, halo or hydroxyl, W is $NR^{14}$, k is 1, Z is $NR^{17}$, r is 1 and each of $R^9$, $R^{10}$, $R^{11}$, $R^{14}$ and $R^{17}$ is independently hydrogen or $C_{1-4}$ alkyl. Preferably, each of $R^5$, $R^6$, $R^7$ and $R^8$ is independently hydrogen or $C_{1-4}$ alkyl. More preferably, $R^5$, $R^6$, $R^7$ and $R^8$ are hydrogen. Preferably, $R^{11}$, $R^{14}$ and $R^{17}$ are hydrogen.

In still other embodiments of a compound of Formula (I), n is 0, Y is a bond, A is $CR^4$, B is $CR^5$, D is $CR^6$, E is $CR^7$, G is $CR^8$, $R^4$ is —$W[C(O)]_kZ(CR^9R^{10})_rCO_2R^{11}$, each of $R^5$, $R^6$, $R^7$ and $R^8$ is independently hydrogen, $C_{1-4}$ alkyl, $C_{1-4}$ alkoxy, $C_{1-4}$ alkoxycarbonyl, carboxyl, halo or hydroxyl, W is $NR^{14}$, k is 1, Z is $NR^{17}$, r is 2 and each of $R^9$, $R^{10}$, $R^{11}$, $R^{14}$ and $R^{17}$ is independently hydrogen or $C_{1-4}$ alkyl. Preferably, each of $R^5$, $R^6$, $R^7$ and $R^8$ is independently hydrogen or $C_{1-4}$ alkyl. More preferably, $R^5$, $R^6$, $R^7$ and $R^8$ are hydrogen. Preferably, $R^{11}$, $R^{14}$ and $R^{17}$ are hydrogen.

In still other embodiments of a compound of Formula (I), n is 0, Y is a bond, A is $CR^4$, B is $CR^5$, D is $CR^6$, E is $CR^7$, G is $CR^8$, $R^4$ is —$W[C(O)]_kZ(CR^9R^{10})_rCO_2R^{11}$, each of $R^5$, $R^6$, $R^7$ and $R^8$ is independently hydrogen, $C_{1-4}$ alkyl, $C_{1-4}$ alkoxy, $C_{1-4}$ alkoxycarbonyl, carboxyl, halo or hydroxyl, W is $NR^{14}$, k is 1, Z is O, r is 1, and each of $R^9$, $R^{10}$, $R^{11}$ and $R^{14}$ is independently hydrogen or $C_{1-4}$ alkyl. Preferably, each of $R^5$, $R^6$, $R^7$ and $R^8$ is independently hydrogen or $C_{1-4}$ alkyl. More preferably, $R^5$, $R^6$, $R^7$ and $R^8$ are hydrogen. Preferably, each of $R^{11}$ and $R^{14}$ are hydrogen.

In still other embodiments of a compound of Formula (I), n is 0, Y is a bond, A is $CR^4$, B is $CR^5$, D is $CR^6$, E is $CR^7$, G is $CR^8$, $R^4$ is —$W[C(O)]_kZ(CR^9R^{10})_rCO_2R^{11}$, each of $R^5$, $R^6$, $R^7$ and $R^8$ is independently hydrogen, $C_{1-4}$ alkyl, $C_{1-4}$ alkoxy, $C_{1-4}$ alkoxycarbonyl, carboxyl, halo or hydroxyl, W is $NR^{14}$, k is 1, Z is O, r is 2, and each of $R^9$, $R^{10}$, $R^{11}$ and $R^{14}$ is independently hydrogen or $C_{1-4}$ alkyl. Preferably, each of $R^5$, $R^6$, $R^7$ and $R^8$ is independently hydrogen or $C_{1-4}$ alkyl. More preferably, $R^5$, $R^6$, $R^7$ and $R^8$ are hydrogen. Preferably, each of $R^{11}$ and $R^{14}$ are hydrogen.

In still other embodiments of a compound of Formula (I), n is 0, Y is a bond, A is $CR^4$, B is $CR^5$, D is $CR^6$, E is $CR^7$, G is $CR^8$, $R^4$ is —$W[C(O)]_kZ(CR^9R^{10})_rCO_2R^{11}$, each of $R^5$, $R^6$, $R^7$ and $R^8$ is independently hydrogen, $C_{1-4}$ alkyl, $C_{1-4}$ alkoxy, $C_{1-4}$ alkoxycarbonyl, carboxyl, halo or hydroxyl, W is $NR^{14}$, k is 1, Z is $CR^{15}R^{16}$, r is 1, and each of $R^9$, $R^{10}$, $R^{11}$, $R^{14}$, $R^{15}$ and $R^{16}$ is independently hydrogen or $C_{1-4}$ alkyl. Preferably, each of $R^5$, $R^6$, $R^7$ and $R^8$ is independently hydrogen or $C_{1-4}$ alkyl. More preferably, $R^5$, $R^6$, $R^7$ and $R^8$ are hydrogen. Preferably, $R^{11}$, $R^{14}$, $R^{15}$ and $R^{16}$ are hydrogen.

In still other embodiments of a compound of Formula (I), n is 0, Y is a bond, A is $CR^4$, B is $CR^5$, D is $CR^6$, E is $CR^7$, G is $CR^8$, $R^4$ is $-W[C(O)]_kZ(CR^9R^{10})_rCO_2R^{11}$, each of $R^5$, $R^6$, $R^7$ and $R^8$ is independently hydrogen, $C_{1-4}$ alkyl, $C_{1-4}$ alkoxy, $C_{1-4}$ alkoxycarbonyl, carboxyl, halo or hydroxyl, W is $NR^{14}$, k is 1, Z is $CR^{15}R^{16}$, r is 2, and each of $R^9$, $R^{10}$, $R^{11}$, $R^{14}$, $R^{15}$ and $R^{16}$ is independently hydrogen or $C_{1-4}$ alkyl. Preferably, each of $R^5$, $R^6$, $R^7$ and $R^8$ is independently hydrogen or $C_{1-4}$ alkyl. More preferably, $R^5$, $R^6$, $R^7$ and $R^8$ are hydrogen. Preferably, $R^{11}$, $R^{14}$, $R^{15}$ and $R^{16}$ are hydrogen.

In still other embodiments of a compound of Formula (I), n is 0, Y is a bond, A is $CR^4$, B is N, D is $CR^6$, E is $CR^7$, G is $CR^8$, $R^4$ is $-W[C(O)]_kZ(CR^9R^{10})_rCO_2R^{11}$, each of $R^6$, $R^7$ and $R^8$ is independently hydrogen, $C_{1-4}$ alkyl, $C_{1-4}$ alkoxy, $C_{1-4}$ alkoxycarbonyl, carboxyl, halo or hydroxyl, and each of $R^9$, $R^{10}$, $R^{11}$, $R^{12}$, $R^{13}$, $R^{14}$, $R^{15}$, $R^{16}$ and $R^{17}$ is independently hydrogen or alkyl. Preferably, each of $R^6$, $R^7$ and $R^8$ is independently hydrogen or $C_{1-4}$ alkyl. More preferably, $R^6$, $R^7$ and $R^8$ are hydrogen. Preferably, each of $R^9$, $R^{10}$, $R^{11}$, $R^{12}$, $R^{13}$, $R^{14}$, $R^{15}$, $R^{16}$ and $R^{17}$ is independently hydrogen or $C_{1-4}$ alkyl.

In still other embodiments of a compound of Formula (I), n is 0, Y is a bond, A is $CR^4$, B is $CR^5$, D is N, E is $CR^7$, G is $CR^8$, $R^4$ is $-W[C(O)]_kZ(CR^9R^{10})_rCO_2R^{11}$, each of $R^5$, $R^7$ and $R^8$ is independently hydrogen, $C_{1-4}$ alkyl, $C_{1-4}$ alkoxy, $C_{1-4}$ alkoxycarbonyl, carboxyl, halo or hydroxyl and each of $R^9$, $R^{10}$, $R^{11}$, $R^{12}$, $R^{13}$, $R^{14}$, $R^{15}$, $R^{16}$ and $R^{17}$ is independently hydrogen or alkyl. Preferably, each of $R^5$, $R^7$ and $R^8$ is independently hydrogen or $C_{1-4}$ alkyl. More preferably, $R^5$, $R^7$ and $R^8$ are hydrogen. Preferably, each of $R^9$, $R^{10}$, $R^{11}$, $R^{12}$, $R^{13}$, $R^{14}$, $R^{15}$, $R^{16}$ and $R^{17}$ is independently hydrogen or $C_{1-4}$ alkyl.

In still other embodiments of a compound of Formula (I), n is 0, Y is a bond, A is $CR^4$, B is $CR^5$, D is $CR^6$, E is N, G is $CR^8$, $R^4$ is $-W[C(O)]_kZ(CR^9R^{10})_rCO_2R^{11}$, each of $R^5$, $R^6$ and $R^8$ is independently hydrogen, $C_{1-4}$ alkyl, $C_{1-4}$ alkoxy, $C_{1-4}$ alkoxycarbonyl, carboxyl, halo or hydroxyl, and each of $R^9$, $R^{10}$, $R^{11}$, $R^{12}$, $R^{13}$, $R^{14}$, $R^{15}$, $R^{16}$ and $R^{17}$ is independently hydrogen or alkyl. Preferably, each of $R^5$, $R^6$ and $R^8$ is independently hydrogen or $C_{1-4}$ alkyl. More preferably, $R^5$, $R^6$ and $R^8$ are hydrogen. Preferably, each of $R^9$, $R^{10}$, $R^{11}$, $R^{12}$, $R^{13}$, $R^{14}$, $R^{15}$, $R^{16}$ and $R^{17}$ is independently hydrogen or $C_{1-4}$ alkyl.

In still other embodiments of a compound of Formula (I), n is 0, Y is a bond, A is $CR^4$, B is $CR^5$, D is $CR^6$, E is $CR^7$, G is N, $R^4$ is $-W[C(O)]_kZ(CR^9R^{10})_rCO_2R^{11}$, each of $R^5$, $R^6$ and $R^7$ is independently hydrogen, $C_{1-4}$ alkyl, $C_{1-4}$ alkoxy, $C_{1-4}$ alkoxycarbonyl, carboxyl, halo or hydroxyl, and each of $R^9$, $R^{10}$, $R^{11}$, $R^{12}$, $R^{13}$, $R^{14}$, $R^{15}$, $R^{16}$ and $R^{17}$ is independently hydrogen or alkyl. Preferably, each of $R^5$, $R^6$ and $R^7$ is independently hydrogen or $C_{1-4}$ alkyl. More preferably, $R^5$, $R^6$ and $R^7$ are hydrogen. Preferably, each of $R^9$, $R^{10}$, $R^{11}$, $R^{12}$, $R^{13}$, $R^{14}$, $R^{15}$, $R^{16}$ and $R^{17}$ is independently hydrogen or $C_{1-4}$ alkyl.

In still other embodiments of a compound of Formula (I), n is 0, Y is a bond, A is $CR^4$, B is N, D is $CR^6$, E is $CR^7$, G is N, $R^4$ is $-W[C(O)]_kZ(CR^9R^{10})_rCO_2R^{11}$, each of $R^6$ and $R^8$ is independently hydrogen, $C_{1-4}$ alkyl, $C_{1-4}$ alkoxy, $C_{1-4}$ alkoxycarbonyl, carboxyl, halo or hydroxyl, and each of $R^9$, $R^{10}$, $R^{11}$, $R^{12}$, $R^{13}$, $R^{14}$, $R^{15}$, $R^{16}$ and $R^{17}$ is independently hydrogen or alkyl. Preferably, each of $R^6$ and $R^8$ is independently hydrogen or $C_{1-4}$ alkyl. More preferably, $R^6$ and $R^8$ are hydrogen. Preferably, each of $R^9$, $R^{10}$, $R^{11}$, $R^{12}$, $R^{13}$, $R^{14}$, $R^{15}$, $R^{16}$ and $R^{17}$ is independently hydrogen or $C_{1-4}$ alkyl.

In still other embodiments of a compound of Formula (I), n is 0, Y is a bond, A is $CR^4$ B is $CR^5$, D is $CR^6$, E is $CR^7$, G is $CR^8$, $R^5$ is $-W[C(O)]_kZ(CR^9R^{10})_rCO_2R^{11}$, each of $R^4$, $R^6$, $R^7$ and $R^8$ is independently hydrogen, $C_{1-4}$ alkyl, $C_{1-4}$ alkoxy, $C_{1-4}$ alkoxycarbonyl, carboxyl, halo or hydroxyl and each of $R^9$, $R^{10}$, $R^{11}$, $R^{12}$, $R^{13}$, $R^{14}$, $R^{15}$, $R^{16}$ and $R^{17}$ is independently hydrogen or alkyl. Preferably, each of $R^4$, $R^6$, $R^7$ and $R^8$ is independently hydrogen or $C_{1-4}$ alkyl. More preferably, $R^4$, $R^6$, $R^7$ and $R^8$ are hydrogen. Preferably, each of $R^9$, $R^{10}$, $R^{11}$, $R^{12}$, $R^{13}$, $R^{14}$, $R^{15}$, $R^{16}$ and $R^{17}$ is independently hydrogen or $C_{1-4}$ alkyl.

In still other embodiments of a compound of Formula (I), n is 0, Y is a bond, A is $CR^4$, B is $CR^5$, D is $CR^6$, E is $CR^7$, G is $CR^8$, $R^5$ is $-W[C(O)]_kZ(CR^9R^{10})_rCO_2R^{11}$, each of $R^4$, $R^6$, $R^7$ and $R^8$ is independently hydrogen, $C_{1-4}$ alkyl, $C_{1-4}$ alkoxy, $C_{1-4}$ alkoxycarbonyl, carboxyl, halo or hydroxyl, W is a bond, k is 1, Z is $NR^{17}$, r is 1, and each of $R^9$, $R^{10}$, $R^{11}$ and $R^{17}$ is independently hydrogen or $C_{1-4}$ alkyl. Preferably, each of $R^4$, $R^6$, $R^7$ and $R^8$ is independently hydrogen or $C_{1-4}$ alkyl. More preferably, $R^4$, $R^6$, $R^7$ and $R^8$ are hydrogen. Preferably, $R^{11}$ and $R^{17}$ are hydrogen.

In still other embodiments of a compound of Formula (I), n is 0, Y is a bond, A is $CR^4$, B is $CR^5$, D is $CR^6$, E is $CR^7$, G is $CR^8$, $R^5$ is $-W[C(O)]_kZ(CR^9R^{10})_rCO_2R^{11}$, each of $R^4$, $R^6$, $R^7$ and $R^8$ is independently hydrogen, $C_{1-4}$ alkyl, $C_{1-4}$ alkoxy, $C_{1-4}$ alkoxycarbonyl, carboxyl, halo or hydroxyl, W is a bond, k is 1, Z is $NR^{17}$, r is 2, and each of $R^9$, $R^{10}$, $R^{11}$ and $R^{17}$ is independently hydrogen or $C_{1-4}$ alkyl. Preferably, each of $R^4$, $R^6$, $R^7$ and $R^8$ is independently hydrogen or $C_{1-4}$ alkyl. More preferably, $R^4$, $R^6$, $R^7$ and $R^8$ are hydrogen. Preferably, $R^{11}$ and $R^{17}$ are hydrogen.

In still other embodiments of a compound of Formula (I), n is 0, Y is a bond, A is $CR^4$, B is $CR^5$, D is $CR^6$, E is $CR^7$, G is $CR^8$, $R^5$ is $-W[C(O)]_kZ(CR^9R^{10})_rCO_2R^{11}$, each of $R^4$, $R^6$, $R^7$ and $R^8$ is independently hydrogen, $C_{1-4}$ alkyl, $C_{1-4}$ alkoxy, $C_{1-4}$ alkoxycarbonyl, carboxyl, halo or hydroxyl, W is a bond, k is 1, Z is O, r is 1, and each of $R^9$, $R^{10}$ and $R^{11}$ is independently hydrogen or $C_{1-4}$ alkyl. Preferably, each of $R^4$, $R^6$, $R^7$ and $R^8$ is independently hydrogen or $C_{1-4}$ alkyl. More preferably, each of $R^5$, $R^6$, $R^7$ and $R^8$ is hydrogen. Preferably, $R^{11}$ is hydrogen.

In still other embodiments of a compound of Formula (I), n is 0, Y is a bond, A is $CR^4$, B is $CR^5$, D is $CR^6$, E is $CR^7$, G is $CR^8$, $R^5$ is $-W[C(O)]_kZ(CR^9R^{10})_rCO_2R^{11}$, each of $R^4$, $R^6$, $R^7$ and $R^8$ is independently hydrogen, $C_{1-4}$ alkyl, $C_{1-4}$ alkoxy, $C_{1-4}$ alkoxycarbonyl, carboxyl, halo or hydroxyl, W is a bond, k is 1, Z is O, r is 2, and each of $R^9$, $R^{10}$ and $R^{11}$ is independently hydrogen or $C_{1-4}$ alkyl. Preferably, each of $R^4$, $R^6$, $R^7$ and $R^8$ is independently hydrogen or $C_{1-4}$ alkyl. More preferably, $R^4$, $R^6$, $R^7$ and $R^8$ are hydrogen. Preferably, $R^{11}$ is hydrogen.

In still other embodiments of a compound of Formula (I), n is 0, Y is a bond, A is $CR^4$, B is $CR^5$, D is $CR^6$, E is $CR^7$, G is $CR^8$, $R^5$ is $-W[C(O)]_kZ(CR^9R^{10})_rCO_2R^{11}$, each of $R^4$, $R^6$, $R^7$ and $R^8$ is independently hydrogen, $C_{1-4}$ alkyl, $C_{1-4}$ alkoxy, $C_{1-4}$ alkoxycarbonyl, carboxyl, halo or hydroxyl, W is O, k is 1, Z is $NR^{17}$, r is 1, and each of $R^9$, $R^{10}$, $R^{11}$ and $R^{17}$ is independently hydrogen or $C_{1-4}$ alkyl. Preferably, each of $R^4$, $R^6$, $R^7$ and $R^8$ is independently hydrogen or $C_{1-4}$ alkyl. More preferably, $R^5$, $R^6$, $R^7$ and $R^8$ are hydrogen. Preferably, $R^{11}$ and $R^{17}$ are hydrogen.

In still other embodiments of a compound of Formula (I), n is 0, Y is a bond, A is $CR^4$, B is $CR^5$, D is $CR^6$, E is $CR^7$, G is $CR^8$, $R^5$ is $-W[C(O)]_kZ(CR^9R^{10})_rCO_2R^{11}$, each of $R^4$, $R^6$, $R^7$ and $R^8$ is independently hydrogen, $C_{1-4}$ alkyl, $C_{1-4}$ alkoxy, $C_{1-4}$ alkoxycarbonyl, carboxyl, halo or hydroxyl, W is O, k is 1, Z is $NR^{17}$, r is 2, and each of $R^9$, $R^{10}$, $R^{11}$ and $R^{17}$ is independently hydrogen or $C_{1-4}$ alkyl. Preferably, each of $R^4$, $R^6$, $R^7$ and $R^8$ is independently hydrogen or $C_{1-4}$ alkyl. More preferably, $R^4$, $R^6$, $R^7$ and $R^8$ are hydrogen. Preferably, $R^{11}$ and $R^{17}$ are hydrogen.

In still other embodiments of a compound of Formula (I), n is 0, Y is a bond, A is $CR^4$, B is $CR^5$, D is $CR^6$, E is $CR^7$, G is $CR^8$, $R^5$ is —$W[C(O)]_k Z(CR^9 R^{10})_r CO_2 R^{11}$, each of $R^4$, $R^6$, $R^7$ and $R^8$ is independently hydrogen, $C_{1-4}$ alkyl, $C_{1-4}$ alkoxy, $C_{1-4}$ alkoxycarbonyl, carboxyl, halo or hydroxyl, W is O, k is 1, Z is O, r is 1, and each of $R^9$, $R^{10}$ and $R^{11}$ is independently hydrogen or $C_{1-4}$ alkyl. Preferably, each of $R^4$, $R^6$, $R^7$ and $R^8$ is independently hydrogen or $C_{1-4}$ alkyl. More preferably, each of $R^4$, $R^6$, $R^7$ and $R^8$ is hydrogen. Preferably, $R^{11}$ is hydrogen.

In still other embodiments of a compound of Formula (I), n is 0, Y is a bond, A is $CR^4$, B is $CR^5$, D is $CR^6$, E is $CR^7$, G is $CR^8$, $R^5$ is —$W[C(O)]_k Z(CR^9 R^{10})_r CO_2 R^{11}$, each of $R^4$, $R^6$, $R^7$ and $R^8$ is independently hydrogen, $C_{1-4}$ alkyl, $C_{1-4}$ alkoxy, $C_{1-4}$ alkoxycarbonyl, carboxyl, halo or hydroxyl, W is O, k is 1, Z is O, r is 2, and each of $R^9$, $R^{10}$ and $R^{11}$ is independently hydrogen or $C_{1-4}$ alkyl. Preferably, each of $R^4$, $R^6$, $R^7$ and $R^8$ is independently hydrogen or $C_{1-4}$ alkyl. More preferably, each of $R^4$, $R^6$, $R^7$ and $R^8$ is hydrogen. Preferably, $R^{11}$ is hydrogen.

In still other embodiments of a compound of Formula (I), n is 0, Y is a bond, A is $CR^4$, B is $CR^5$, D is $CR^6$, E is $CR^7$, G is $CR^8$, $R^5$ is —$W[C(O)]_k Z(CR^9 R^{10})_r CO_2 R^{11}$, each of $R^4$, $R^6$, $R^7$ and $R^8$ is independently hydrogen, $C_{1-4}$ alkyl, $C_{1-4}$ alkoxy, $C_{1-4}$ alkoxycarbonyl, carboxyl, halo or hydroxyl, W is O, k is 1, Z is $CR^{15}R^{16}$, r is 1, and each of $R^9$, $R^{10}$, $R^{11}$, $R^{15}$ and $R^{16}$ is independently hydrogen or $C_{1-4}$ alkyl. Preferably, each of $R^4$, $R^6$, $R^7$ and $R^8$ is independently hydrogen or $C_{1-4}$ alkyl. More preferably, $R^4$, $R^6$, $R^7$ and $R^8$ are hydrogen. Preferably, $R^{11}$, $R^{15}$ and $R^{16}$ are hydrogen.

In still other embodiments of a compound of Formula (I), n is 0, Y is a bond, A is $CR^4$, B is $CR^5$, D is $CR^6$, E is $CR^7$, G is $CR^8$, $R^5$ is —$W[C(O)]_k Z(CR^9 R^{10})_r CO_2 R^{11}$, each of $R^4$, $R^6$, $R^7$ and $R^8$ is independently hydrogen, $C_{1-4}$ alkyl, $C_{1-4}$ alkoxy, $C_{1-4}$ alkoxycarbonyl, carboxyl, halo or hydroxyl, W is O, k is 1, Z is $CR^{15}R^{16}$, r is 2, and each of $R^9$, $R^{10}$, $R^{11}$, $R^{15}$ and $R^{16}$ is independently hydrogen or $C_{1-4}$ alkyl. Preferably, each of $R^4$, $R^6$, $R^7$ and $R^8$ is independently hydrogen or $C_{1-4}$ alkyl. More preferably, $R^4$, $R^6$, $R^7$ and $R^8$ are hydrogen. Preferably, $R^{11}$, $R^{15}$ and $R^{16}$ are hydrogen.

In still other embodiments of a compound of Formula (I), n is 0, Y is a bond, A is $CR^4$, B is $CR^5$, D is $CR^6$, E is $CR^7$, G is $CR^8$, $R^5$ is —$W[C(O)]_k Z(CR^9 R^{10})_r CO_2 R^{11}$, each of $R^4$, $R^6$, $R^7$ and $R^8$ is independently hydrogen, $C_{1-4}$ alkyl, $C_{1-4}$ alkoxy, $C_{1-4}$ alkoxycarbonyl, carboxyl, halo or hydroxyl, W is $NR^{14}$, k is 1, Z is $NR^{17}$, r is 1 and each of $R^9$, $R^{10}$, $R^{11}$, $R^{14}$ and $R^{17}$ is independently hydrogen or $C_{1-4}$ alkyl. Preferably, each of $R^4$, $R^6$, $R^7$ and $R^8$ is independently hydrogen or $C_{1-4}$ alkyl. More preferably, $R^4$, $R^6$, $R^7$ and $R^8$ are hydrogen. Preferably, $R^{11}$, $R^{14}$ and $R^{17}$ are hydrogen.

In still other embodiments of a compound of Formula (I), n is 0, Y is a bond, A is $CR^4$, B is $CR^5$, D is $CR^6$, E is $CR^7$, G is $CR^8$, $R^5$ is —$W[C(O)]_k Z(CR^9 R^{10})_r CO_2 R^{11}$, each of $R^4$, $R^6$, $R^7$ and $R^8$ is independently hydrogen, $C_{1-4}$ alkyl, $C_{1-4}$ alkoxy, $C_{1-4}$ alkoxycarbonyl, carboxyl, halo or hydroxyl, W is $NR^{14}$, k is 1, Z is $NR^{17}$, r is 2 and each of $R^9$, $R^{10}$, $R^{11}$, $R^{14}$ and $R^{17}$ is independently hydrogen or $C_{1-4}$ alkyl. Preferably, each of $R^4$, $R^6$, $R^7$ and $R^8$ is independently hydrogen or $C_{1-4}$ alkyl. More preferably, $R^4$, $R^6$, $R^7$ and $R^8$ are hydrogen. Preferably, $R^{11}$, $R^{14}$ and $R^{17}$ are hydrogen.

In still other embodiments of a compound of Formula (I), n is 0, Y is a bond, A is $CR^4$, B is $CR^5$, D is $CR^6$, E is $CR^7$, G is $CR^8$, $R^5$ is —$W[C(O)]_k Z(CR^9 R^{10})_r CO_2 R^{11}$, each of $R^4$, $R^6$, $R^7$ and $R^8$ is independently hydrogen, $C_{1-4}$ alkyl, $C_{1-4}$ alkoxy, $C_{1-4}$ alkoxycarbonyl, carboxyl, halo or hydroxyl, W is $NR^{14}$, k is 1, Z is O, r is 1, and each of $R^9$, $R^{10}$, $R^{11}$ and $R^{14}$ is independently hydrogen or $C_{1-4}$ alkyl. Preferably, each of $R^4$, $R^6$, $R^7$ and $R^8$ is independently hydrogen or $C_{1-4}$ alkyl. More preferably, $R^4$, $R^6$, $R^7$ and $R^8$ are hydrogen. Preferably, each of $R^{11}$ and $R^{14}$ are hydrogen.

In still other embodiments of a compound of Formula (I), n is 0, Y is a bond, A is $CR^4$, B is $CR^5$, D is $CR^6$, E is $CR^7$, G is $CR^8$, $R^5$ is —$W[C(O)]_k Z(CR^9 R^{10})_r CO_2 R^{11}$, each of $R^4$, $R^6$, $R^7$ and $R^8$ is independently hydrogen, $C_{1-4}$ alkyl, $C_{1-4}$ alkoxy, $C_{1-4}$ alkoxycarbonyl, carboxyl, halo or hydroxyl, W is $NR^{14}$, k is 1, Z is O, r is 2, and each of $R^9$, $R^{10}$, $R^{11}$ and $R^{14}$ is independently hydrogen or $C_{1-4}$ alkyl. Preferably, each of $R^4$, $R^6$, $R^7$ and $R^8$ is independently hydrogen or $C_{1-4}$ alkyl. More preferably, $R^4$, $R^6$, $R^7$ and $R^8$ are hydrogen. Preferably, each of $R^{11}$ and $R^{14}$ are hydrogen.

In still other embodiments of a compound of Formula (I), n is 0, Y is a bond, A is $CR^4$, B is $CR^5$, D is $CR^6$, E is $CR^7$, G is $CR^8$, $R^5$ is —$W[C(O)]_k Z(CR^9 R^{10})_r CO_2 R^{11}$, each of $R^4$, $R^6$, $R^7$ and $R^8$ is independently hydrogen, $C_{1-4}$ alkyl, $C_{1-4}$ alkoxy, $C_{1-4}$ alkoxycarbonyl, carboxyl, halo or hydroxyl, W is $NR^{14}$, k is 1, Z is $CR^{15}R^{16}$, r is 1, and each of $R^9$, $R^{10}$, $R^{11}$, $R^{14}$, $R^{15}$ and $R^{16}$ is independently hydrogen or $C_{1-4}$ alkyl. Preferably, each of $R^4$, $R^6$, $R^7$ and $R^8$ is independently hydrogen or $C_{1-4}$ alkyl. More preferably, $R^4$, $R^6$, $R^7$ and $R^8$ are hydrogen. Preferably, $R^{11}$, $R^{14}$, $R^{15}$ and $R^{16}$ are hydrogen.

In still other embodiments of a compound of Formula (I), n is 0, Y is a bond, A is $CR^4$, B is $CR^5$, D is $CR^6$, E is $CR^7$, G is $CR^8$, $R^5$ is —$W[C(O)]_k Z(CR^9 R^{10})_r CO_2 R^{11}$, each of $R^4$, $R^6$, $R^7$ and $R^8$ is independently hydrogen, $C_{1-4}$ alkyl, $C_{1-4}$ alkoxy, $C_{1-4}$ alkoxycarbonyl, carboxyl, halo or hydroxyl, W is $NR^{14}$, k is 1, Z is $CR^{15}R^{16}$, r is 2, and each of $R^9$, $R^{10}$, $R^{11}$, $R^{14}$, $R^{15}$ and $R^{16}$ is independently hydrogen or $C_{1-14}$ alkyl. Preferably, each of $R^4$, $R^6$, $R^7$ and $R^8$ is independently hydrogen or $C_{1-4}$ alkyl. More preferably, $R^4$, $R^6$, $R^7$ and $R^8$ are hydrogen. Preferably, $R^{11}$, $R^{14}$, $R^{15}$ and $R^{16}$ are hydrogen.

In still other embodiments of a compound of Formula (I), n is 0, Y is a bond, A is N, B is $CR^5$, D is $CR^6$, E is $CR^7$, G is $CR^8$, $R^5$ is —$W[C(O)]_k Z(CR^9 R^{10})_r CO_2 R^{11}$, each of $R^6$, $R^7$ and $R^8$ is independently hydrogen, $C_{1-4}$ alkyl, $C_{1-4}$ alkoxy, $C_{1-4}$ alkoxycarbonyl, carboxyl, halo or hydroxyl, and each of $R^9$, $R^{10}$, $R^{11}$, $R^{12}$, $R^{13}$, $R^{14}$, $R^{15}$, $R^{16}$ and $R^{17}$ is independently hydrogen or alkyl. Preferably, each of $R^6$, $R^7$ and $R^8$ is independently hydrogen or $C_{1-4}$ alkyl. More preferably, $R^6$, $R^7$ and $R^8$ are hydrogen. Preferably, each of $R^9$, $R^{10}$, $R^{11}$, $R^{12}$, $R^{13}$, $R^{14}$, $R^{15}$, $R^{16}$ and $R^{17}$ is independently hydrogen or $C_{1-4}$ alkyl.

In still other embodiments of a compound of Formula (I), n is 0, Y is a bond, A is $CR^4$, B is $CR^5$, D is N, E is $CR^7$, G is $CR^8$, $R^5$ is —$W[C(O)]_k Z(CR^9 R^{10})_r CO_2 R^{11}$, each of $R^4$, $R^7$ and $R^8$ is independently hydrogen, $C_{1-4}$ alkyl, $C_{1-4}$ alkoxy, $C_{1-4}$ alkoxycarbonyl, carboxyl, halo or hydroxyl and each of $R^9$, $R^{10}$, $R^{11}$, $R^{12}$, $R^{13}$, $R^{14}$, $R^{15}$, $R^{16}$ and $R^{17}$ is independently hydrogen or alkyl. Preferably, each of $R^4$, $R^7$ and $R^8$ is independently hydrogen or $C_{1-4}$ alkyl. More preferably, $R^4$, $R^7$ and $R^8$ are hydrogen. Preferably, each of $R^9$, $R^{10}$, $R^{11}$, $R^{12}$, $R^{13}$, $R^{14}$, $R^{15}$, $R^{16}$ and $R^{17}$ is independently hydrogen or $C_{1-4}$ alkyl.

In still other embodiments of a compound of Formula (I), n is 0, Y is a bond, A is $CR^4$, B is $CR^5$, D is $CR^6$, E is N, G is $CR^8$, $R^5$ is —$W[C(O)]_k Z(CR^9 R^{10})_r CO_2 R^{11}$, each of $R^4$, $R^6$ and $R^8$ is independently hydrogen, $C_{1-4}$ alkyl, $C_{1-4}$ alkoxy, $C_{1-4}$ alkoxycarbonyl, carboxyl, halo or hydroxyl and each of $R^9$, $R^{10}$, $R^{11}$, $R^{12}$, $R^{13}$, $R^{14}$, $R^{15}$, $R^{16}$ and $R^{17}$ is independently hydrogen or alkyl. Preferably, each of $R^4$, $R^6$ and $R^8$ is independently hydrogen or $C_{1-4}$ alkyl. More preferably, $R^4$, $R^6$ and $R^8$ are hydrogen. Preferably, each of $R^9$, $R^{10}$, $R^{11}$, $R^{12}$, $R^{13}$, $R^{14}$, $R^{15}$, $R^{16}$ and $R^{17}$ is independently hydrogen or $C_{1-4}$ alkyl.

In still other embodiments of a compound of Formula (I), n is 0, Y is a bond, A is $CR^4$, B is $CR^5$, D is $CR^6$, E is $CR^7$, G is N, $R^5$ is —$W[C(O)]_kZ(CR^9R^{10})_rCO_2R^{11}$, each of $R^4$, $R^6$ and $R^7$ is independently hydrogen, $C_{1-4}$ alkyl, $C_{1-4}$ alkoxy, $C_{1-4}$ alkoxycarbonyl, carboxyl, halo or hydroxyl and each of $R^9$, $R^{10}$, $R^{11}$, $R^{12}$, $R^{13}$, $R^{14}$, $R^{15}$, $R^{16}$ and $R^{17}$ is independently hydrogen or alkyl. Preferably, each of $R^4$, $R^6$ and $R^7$ is independently hydrogen or $C_{1-4}$ alkyl. More preferably, $R^4$, $R^6$ and $R^7$ are hydrogen. Preferably, each of $R^9$, $R^{10}$, $R^{11}$, $R^{12}$, $R^{13}$, $R^{14}$, $R^{15}$, $R^{16}$ and $R^{17}$ is independently hydrogen or $C_{1-4}$ alkyl.

In still other embodiments of a compound of Formula (I), n is 0, Y is a bond, A is N, B is $CR^5$, D is $CR^6$, E is $CR^7$, G is N, $R^5$ is —$W[C(O)]_kZ(CR^9R^{10})_rCO_2R^{11}$, each of $R^6$ and $R^7$ is independently hydrogen, $C_{1-4}$ alkyl, $C_{1-4}$ alkoxy, $C_{1-4}$ alkoxycarbonyl, carboxyl, halo or hydroxyl and each of $R^9$, $R^{10}$, $R^{11}$, $R^{12}$, $R^{13}$, $R^{14}$, $R^{15}$, $R^{16}$ and $R^{17}$ is independently hydrogen or alkyl. Preferably, each of $R^6$ and $R^7$ is independently hydrogen or $C_{1-4}$ alkyl. More preferably, $R^6$ and $R^7$ are hydrogen. Preferably, each of $R^9$, $R^{10}$, $R^{11}$, $R^{12}$, $R^{13}$, $R^{14}$, $R^{15}$, $R^{16}$ and $R^{17}$ is independently hydrogen or $C_{1-4}$ alkyl.

In still other embodiments of a compound of Formula (I), n is 0, Y is a bond, A is N, B is $CR^5$, D is N, E is $CR^7$, G is $CR^8$, $R^5$ is —$W[C(O)]_kZ(CR^9R^{10})_rCO_2R^{11}$, each of $R^7$ and $R^8$ is independently hydrogen, $C_{1-4}$ alkyl, $C_{1-4}$ alkoxy, $C_{1-4}$ alkoxycarbonyl, carboxyl, halo or hydroxyl and each of $R^9$, $R^{10}$, $R^{11}$, $R^{12}$, $R^{13}$, $R^{14}$, $R^{15}$, $R^{16}$ and $R^{17}$ is independently hydrogen or alkyl. Preferably, each of $R^7$ and $R^8$ is independently hydrogen or $C_{1-4}$ alkyl. More preferably, $R^7$ and $R^8$ are hydrogen. Preferably, each of $R^9$, $R^{10}$, $R^{11}$, $R^{12}$, $R^{13}$, $R^{14}$, $R^{15}$, $R^{16}$ and $R^{17}$ is independently hydrogen or $C_{1-4}$ alkyl.

In still other embodiments of a compound of Formula (I), n is 0, Y is a bond, A is N, B is $CR^5$, D is $CR^6$, E is N, G is $CR^8$, $R^5$ is —$W[C(O)]_kZ(CR^9R^{10})_rCO_2R^{11}$, each of $R^7$ and $R^8$ is independently hydrogen, $C_{1-4}$ alkyl, $C_{1-4}$ alkoxy, $C_{1-4}$ alkoxycarbonyl, carboxyl, halo or hydroxyl and each of $R^9$, $R^{10}$, $R^{11}$, $R^{12}$, $R^{13}$, $R^{14}$, $R^{15}$, $R^{16}$ and $R^{17}$ is independently hydrogen or alkyl. Preferably, each of $R^7$ and $R^8$ is independently hydrogen or $C_{1-4}$ alkyl. More preferably, $R^7$ and $R^8$ are hydrogen. Preferably, each of $R^9$, $R^{10}$, $R^{11}$, $R^{12}$, $R^{13}$, $R^{14}$ $R^{15}$, $R^{16}$ and $R^{17}$ is independently hydrogen or $C_{1-4}$ alkyl.

In still other embodiments of a compound of Formula (I), n is 0, Y is a bond, A is $CR^4$, B is $CR^5$, D is N, E is $CR^7$, G is N, $R^5$ is —$W[C(O)]_kZ(CR^9R^{10})_rCO_2R^{11}$, each of $R^4$ and $R^8$ is independently hydrogen, $C_{1-4}$ alkyl, $C_{1-4}$ alkoxy, $C_{1-4}$ alkoxycarbonyl, carboxyl, halo or hydroxyl and each of $R^9$, $R^{10}$, $R^{11}$, $R^{12}$, $R^{13}$, $R^{14}$, $R^{15}$, $R^{16}$ and $R^{17}$ is independently hydrogen or alkyl. Preferably, each of $R^4$ and $R^8$ is independently hydrogen or $C_{1-4}$ alkyl. More preferably, $R^4$ and $R^8$ are hydrogen. Preferably, each of $R^9$, $R^{10}$, $R^{11}$, $R^{12}$, $R^{13}$, $R^{14}$, $R^{15}$, $R^{16}$ and $R^{17}$ is independently hydrogen or $C_{1-4}$ alkyl.

In still other embodiments of a compound of Formula (I), n is 0, Y is a bond, A is $CR^4$, B is $CR^5$, D is $CR^6$, E is $CR^7$, G is $CR^8$, $R^6$ is —$W[C(O)]_kZ(CR^9R^{10})_rCO_2R^{11}$, each of $R^4$, $R^5$, $R^7$ and $R^8$ is independently hydrogen, $C_{1-4}$ alkyl, $C_{1-4}$ alkoxy, $C_{1-4}$ alkoxycarbonyl, carboxyl, halo or hydroxyl and each of $R^9$, $R^{10}$, $R^{11}$, $R^{12}$, $R^{13}$, $R^{14}$ $R^{15}$, $R^{16}$ and $R^{17}$ is independently hydrogen or alkyl. Preferably, each of $R^4$, $R^5$, $R^7$ and $R^8$ is independently hydrogen or $C_{1-4}$ alkyl. More preferably, $R^4$, $R^5$, $R^7$ and $R^8$ are hydrogen. Preferably, each of $R^9$, $R^{10}$, $R^{11}$, $R^{12}$, $R^{13}$, $R^{14}$, $R^{15}$, $R^{16}$ and $R^{17}$ is independently hydrogen or $C_{1-4}$ alkyl.

In still other embodiments of a compound of Formula (I), n is 0, Y is a bond, A is $CR^4$, B is $CR^5$, D is $CR^6$, E is $CR^7$, G is $CR^8$, $R^6$ is —$W[C(O)]_kZ(CR^9R^{10})_rCO_2R^{11}$, each of $R^4$, $R^5$, $R^7$ and $R^8$ is independently hydrogen, $C_{1-4}$ alkyl, $C_{1-4}$ alkoxy, $C_{1-4}$ alkoxycarbonyl, carboxyl, halo or hydroxyl, W is a bond, k is 1, Z is $NR^{17}$, r is 1, and each of $R^9$, $R^{10}$, $R^{11}$ and $R^{17}$ is independently hydrogen or $C_{1-4}$ alkyl. Preferably, each of $R^4$, $R^5$, $R^7$ and $R^8$ is independently hydrogen or $C_{1-4}$ alkyl. More preferably, $R^4$, $R^5$, $R^7$ and $R^8$ are hydrogen. Preferably, $R^{11}$ and $R^{17}$ are hydrogen.

In still other embodiments of a compound of Formula (I), n is 0, Y is a bond, A is $CR^4$, B is $CR^5$, D is $CR^6$, E is $CR^7$, G is $CR^8$, $R^6$ is —$W[C(O)]_kZ(CR^9R^{10})_rCO_2R^{11}$, each of $R^4$, $R^5$, $R^7$ and $R^8$ is independently hydrogen, $C_{1-4}$ alkyl, $C_{1-4}$ alkoxy, $C_{1-4}$ alkoxycarbonyl, carboxyl, halo or hydroxyl, W is a bond, k is 1, Z is $NR^{17}$, r is 2, and each of $R^9$, $R^{10}$, $R^{11}$ and $R^{17}$ is independently hydrogen or $C_{1-4}$ alkyl. Preferably, each of $R^4$, $R^5$, $R^7$ and $R^8$ is independently hydrogen or $C_{1-4}$ alkyl. More preferably, $R^4$, $R^5$, $R^7$ and $R^8$ are hydrogen. Preferably, $R^{11}$ and $R^{17}$ are hydrogen.

In still other embodiments of a compound of Formula (I), n is 0, Y is a bond, A is $CR^4$, B is $CR^5$, D is $CR^6$, E is $CR^7$, G is $CR^8$, $R^6$ is —$W[C(O)]_kZ(CR^9R^{10})_rCO_2R^{11}$, each of $R^4$, $R^5$, $R^7$ and $R^8$ is independently hydrogen, $C_{1-4}$ alkyl, $C_{1-4}$ alkoxy, $C_{1-4}$ alkoxycarbonyl, carboxyl, halo or hydroxyl, W is a bond, k is 1, Z is O, r is 1, and each of $R^9$, $R^{10}$ and $R^{11}$ is independently hydrogen or $C_{1-4}$ alkyl. Preferably, each of $R^4$, $R^5$, $R^7$ and $R^8$ is independently hydrogen or $C_{1-4}$ alkyl. More preferably, $R^4$, $R^5$, $R^7$ and $R^8$ are hydrogen. Preferably, $R^{11}$ is hydrogen.

In still other embodiments of a compound of Formula (I), n is 0, Y is a bond, A is $CR^4$, B is $CR^5$, D is $CR^6$, E is $CR^7$, G is $CR^8$, $R^6$ is —$W[C(O)]_kZ(CR^9R^{10})_rCO_2R^{11}$, each of $R^4$, $R^5$, $R^7$ and $R^8$ is independently hydrogen, $C_{1-4}$ alkyl, $C_{1-4}$ alkoxy, $C_{1-4}$ alkoxycarbonyl, carboxyl, halo or hydroxyl, W is a bond, k is 1, Z is O, r is 2, and each of $R^9$, $R^{10}$ and $R^{11}$ is independently hydrogen or $C_{1-4}$ alkyl. Preferably, each of $R^4$, $R^5$, $R^7$ and $R^8$ is independently hydrogen or $C_{1-4}$ alkyl. More preferably, $R^4$, $R^5$, $R^7$ and $R^8$ are hydrogen. Preferably, $R^{11}$ is hydrogen.

In still other embodiments of a compound of Formula (I), n is 0, Y is a bond, A is $CR^4$, B is $CR^5$, D is $CR^6$, E is $CR^7$, G is $CR^8$, $R^6$ is —$W[C(O)]_kZ(CR^9R^{10})_rCO_2R^{11}$, each of $R^4$, $R^5$, $R^7$ and $R^8$ is independently hydrogen, $C_{1-4}$ alkyl, $C_{1-4}$ alkoxy, $C_{1-4}$ alkoxycarbonyl, carboxyl, halo or hydroxyl, W is O, k is 1, Z is $NR^{17}$, r is 1, and each of $R^9$, $R^{10}$, $R^{11}$ and $R^{17}$ is independently hydrogen or $C_{1-4}$ alkyl. Preferably, each of $R^4$, $R^5$, $R^7$ and $R^8$ is independently hydrogen or $C_{1-4}$ alkyl. More preferably, $R^4$, $R^5$, $R^7$ and $R^8$ are hydrogen. Preferably, $R^{11}$ and $R^{17}$ are hydrogen.

In still other embodiments of a compound of Formula (I), n is 0, Y is a bond, A is $CR^4$, B is $CR^5$, D is $CR^6$, E is $CR^7$, G is $CR^8$, $R^6$ is —$W[C(O)]_kZ(CR^9R^{10})_rCO_2R^{11}$, each of $R^4$, $R^5$, $R^7$ and $R^8$ is independently hydrogen, $C_{1-4}$ alkyl, $C_{1-4}$ alkoxy, $C_{1-4}$ alkoxycarbonyl, carboxyl, halo or hydroxyl, W is O, k is 1, Z is $NR^{17}$, r is 2, and each of $R^9$, $R^{10}$, $R^{11}$ and $R^{17}$ is independently hydrogen or $C_{1-4}$ alkyl. Preferably, each of $R^4$, $R^5$, $R^7$ and $R^8$ is independently hydrogen or $C_{1-4}$ alkyl. More preferably, $R^4$, $R^5$, $R^7$ and $R^8$ are hydrogen. Preferably, $R^{11}$ and $R^{17}$ are hydrogen.

In still other embodiments of a compound of Formula (I), n is 0, Y is a bond, A is $CR^4$, B is $CR^5$, D is $CR^6$, E is $CR^7$, G is $CR^8$, $R^6$ is —$W[C(O)]_kZ(CR^9R^{10})_rCO_2R^{11}$, each of $R^4$, $R^5$, $R^7$ and $R^8$ is independently hydrogen, $C_{1-4}$ alkyl, $C_{1-4}$ alkoxy, $C_{1-4}$ alkoxycarbonyl, carboxyl, halo or hydroxyl, W is O, k is 1, Z is O, r is 1, and each of $R^9$, $R^{10}$ and $R^{11}$ is independently hydrogen or $C_{1-4}$ alkyl. Preferably, each of $R^4$, $R^5$, $R^7$ and $R^8$ is independently hydrogen or $C_{1-4}$ alkyl. More preferably, $R^4$, $R^5$, $R^7$ and $R^8$ are hydrogen. Preferably, $R^{11}$ is hydrogen.

In still other embodiments of a compound of Formula (I), n is 0, Y is a bond, A is $CR^4$, B is $CR^5$, D is $CR^6$, E is $CR^7$, G is $CR^8$, $R^6$ is —$W[C(O)]_kZ(CR^9R^{10})_rCO_2R^{11}$, each of $R^4$, $R^5$, $R^7$ and $R^8$ is independently hydrogen, $C_{1-4}$ alkyl, $C_{1-4}$ alkoxy, $C_{1-4}$ alkoxycarbonyl, carboxyl, halo or hydroxyl, W is O, k is 1, Z is O, r is 2, and each of $R^9$, $R^{10}$ and $R^{11}$ is independently hydrogen or $C_{1-4}$ alkyl. Preferably, each of $R^4$, $R^5$, $R^7$ and $R^8$ is independently hydrogen or $C_{1-4}$ alkyl. More preferably, $R^4$, $R^5$, $R^7$ and $R^8$ are hydrogen. Preferably, $R^{11}$ is hydrogen.

In still other embodiments of a compound of Formula (I), n is 0, Y is a bond, A is $CR^4$, B is $CR^5$, D is $CR^6$, E is $CR^7$, G is $CR^8$, $R^6$ is —$W[C(O)]_kZ(CR^9R^{10})_rCO_2R^{11}$, each of $R^4$, $R^5$, $R^7$ and $R^8$ is independently hydrogen, $C_{1-4}$ alkyl, $C_{1-4}$ alkoxy, $C_{1-4}$ alkoxycarbonyl, carboxyl, halo or hydroxyl, W is O, k is 1, Z is $CR^{15}R^{16}$, r is 1, and each of $R^9$, $R^{10}$, $R^{11}$, $R^{15}$ and $R^{16}$ is independently hydrogen or $C_{1-4}$ alkyl. Preferably, each of $R^4$, $R^5$, $R^7$ and $R^8$ is independently hydrogen or $C_{1-4}$ alkyl. More preferably, $R^4$, $R^5$, $R^7$ and $R^8$ are hydrogen. Preferably, $R^{11}$, $R^{15}$ and $R^{16}$ are hydrogen.

In still other embodiments of a compound of Formula (I), n is 0, Y is a bond, A is $CR^4$, B is $CR^5$, D is $CR^6$, E is $CR^7$, G is $CR^8$, $R^6$ is —$W[C(O)]_kZ(CR^9R^{10})_rCO_2R^{11}$, each of $R^4$, $R^5$, $R^7$ and $R^8$ is independently hydrogen, $C_{1-4}$ alkyl, $C_{1-4}$ alkoxy, $C_{1-4}$ alkoxycarbonyl, carboxyl, halo or hydroxyl, W is O, k is 1, Z is $CR^{15}R^{16}$, r is 2, and each of $R^9$, $R^{10}$, $R^{11}$, $R^{15}$ and $R^{16}$ is independently hydrogen or $C_{1-4}$ alkyl. Preferably, each of $R^4$, $R^5$, $R^7$ and $R^8$ is independently hydrogen or $C_{1-4}$ alkyl. More preferably, $R^4$, $R^5$, $R^7$ and $R^8$ are hydrogen. Preferably, $R^{11}$, $R^{15}$ and $R^{16}$ are hydrogen.

In still other embodiments of a compound of Formula (I), n is 0, Y is a bond, A is $CR^4$, B is $CR^5$, D is $CR^6$, E is $CR^7$, G is $CR^8$, $R^6$ is —$W[C(O)]_kZ(CR^9R^{10})_rCO_2R^{11}$, each of $R^4$, $R^5$, $R^7$ and $R^8$ is independently hydrogen, $C_{1-4}$ alkyl, $C_{1-4}$ alkoxy, $C_{1-4}$ alkoxycarbonyl, carboxyl, halo or hydroxyl, W is $NR^{14}$, k is 1, Z is $NR^{17}$, r is 1 and each of $R^9$, $R^{10}$, $R^{11}$, $R^{14}$ and $R^{17}$ is independently hydrogen or $C_{1-4}$ alkyl. Preferably, each of $R^4$, $R^5$, $R^7$ and $R^8$ is independently hydrogen or $C_{1-4}$ alkyl. More preferably, $R^4$, $R^5$, $R^7$ and $R^8$ are hydrogen. Preferably, $R^{11}$, $R^{14}$ and $R^{17}$ are hydrogen.

In still other embodiments of a compound of Formula (I), n is 0, Y is a bond, A is $CR^4$, B is $CR^5$, D is $CR^6$, E is $CR^7$, G is $CR^8$, $R^6$ is —$W[C(O)]_kZ(CR^9R^{10})_rCO_2R^{11}$, each of $R^4$, $R^5$, $R^7$ and $R^8$ is independently hydrogen, $C_{1-4}$ alkyl, $C_{1-4}$ alkoxy, $C_{1-4}$ alkoxycarbonyl, carboxyl, halo or hydroxyl, W is $NR^{14}$, k is 1, Z is $NR^{17}$, r is 2 and each of $R^9$, $R^{10}$, $R^{11}$, $R^{14}$ and $R^{17}$ is independently hydrogen or $C_{1-4}$ alkyl. Preferably, each of $R^4$, $R^5$, $R^7$ and $R^8$ is independently hydrogen or $C_{1-4}$ alkyl. More preferably, $R^4$, $R^5$, $R^7$ and $R^8$ are hydrogen. Preferably, $R^{11}$, $R^{14}$ and $R^{17}$ are hydrogen.

In still other embodiments of a compound of Formula (I), n is 0, Y is a bond, A is $CR^4$, B is $CR^5$, D is $CR^6$, E is $CR^7$, G is $CR^8$, $R^6$ is —$W[C(O)]_kZ(CR^9R^{10})_rCO_2R^{11}$, each of $R^4$, $R^5$, $R^7$ and $R^8$ is independently hydrogen, $C_{1-4}$ alkyl, $C_{1-4}$ alkoxy, $C_{1-4}$ alkoxycarbonyl, carboxyl, halo or hydroxyl, W is $NR^{14}$, k is 1, Z is O, r is 1, and each of $R^9$, $R^{10}$, $R^{11}$ and $R^{14}$ is independently hydrogen or $C_{1-4}$ alkyl. Preferably, each of $R^4$, $R^5$, $R^7$ and $R^8$ is independently hydrogen or $C_{1-4}$ alkyl. More preferably, $R^4$, $R^5$, $R^7$ and $R^8$ are hydrogen. Preferably, each of $R^{11}$ and $R^{14}$ are hydrogen.

In still other embodiments of a compound of Formula (I), n is 0, Y is a bond, A is $CR^4$, B is $CR^5$, D is $CR^6$, E is $CR^7$, G is $CR^8$, $R^6$ is —$W[C(O)]_kZ(CR^9R^{10})_rCO_2R^{11}$, each of $R^4$, $R^5$, $R^7$ and $R^8$ is independently hydrogen, $C_{1-4}$ alkyl, $C_{1-4}$ alkoxy, $C_{1-4}$ alkoxycarbonyl, carboxyl, halo or hydroxyl, W is $NR^{14}$, k is 1, Z is O, r is 2, and each of $R^9$, $R^{10}$, $R^{11}$ and $R^{14}$ is independently hydrogen or $C_{1-4}$ alkyl. Preferably, each of $R^4$, $R^5$, $R^7$ and $R^8$ is independently hydrogen or $C_{1-4}$ alkyl. More preferably, $R^4$, $R^5$, $R^7$ and $R^8$ are hydrogen. Preferably, each of $R^{11}$ and $R^{14}$ are hydrogen.

In still other embodiments of a compound of Formula (I), n is 0, Y is a bond, A is $CR^4$, B is $CR^5$, D is $CR^6$, E is $CR^7$, G is $CR^8$, $R^6$ is —$W[C(O)]_kZ(CR^9R^{10})_rCO_2R^{11}$, each of $R^4$, $R^5$, $R^7$ and $R^8$ is independently hydrogen, $C_{1-4}$ alkyl, $C_{1-4}$ alkoxy, $C_{1-4}$ alkoxycarbonyl, carboxyl, halo or hydroxyl, W is $NR^{14}$, k is 1, Z is $CR^{15}R^{16}$, r is 1, and each of $R^9$, $R^{10}$, $R^{11}$, $R^{14}$, $R^{15}$ and $R^{16}$ is independently hydrogen or $C_{1-4}$ alkyl. Preferably, each of $R^4$, $R^5$, $R^7$ and $R^8$ is independently hydrogen or $C_{1-4}$ alkyl. More preferably, $R^4$, $R^5$, $R^7$ and $R^8$ are hydrogen. Preferably, $R^{11}$, $R^{14}$, $R^{15}$ and $R^{16}$ are hydrogen.

In still other embodiments of a compound of Formula (I), n is 0, Y is a bond, A is $CR^4$, B is $CR^5$, D is $CR^6$, E is $CR^7$, G is $CR^8$, $R^6$ is —$W[C(O)]_kZ(CR^9R^{10})_rCO_2R^{11}$, each of $R^5$, $R^5$, $R^7$ and $R^8$ is independently hydrogen, $C_{1-4}$ alkyl, $C_{1-4}$ alkoxy, $C_{1-4}$ alkoxycarbonyl, carboxyl, halo or hydroxyl, W is $NR^{14}$ k is 1, Z is $CR^{15}R^{16}$, r is 2, and each of $R^9$, $R^{10}$, $R^{11}$, $R^{14}$, $R^{15}$ and $R^{16}$ is independently hydrogen or $C_{1-4}$ alkyl. Preferably, each of $R^4$, $R^5$, $R^7$ and $R^8$ is independently hydrogen or $C_{1-4}$ alkyl. More preferably, $R^4$, $R^5$, $R^7$ and $R^8$ are hydrogen. Preferably, $R^{11}$, $R^{14}$, $R^{15}$ and $R^{16}$ are hydrogen.

In still other embodiments of a compound of Formula (I), n is 0, Y is a bond, A is N, B is $CR^5$, D is $CR^6$, E is $CR^7$, G is $CR^8$, $R^6$ is —$W[C(O)]_kZ(CR^9R^{10})_rCO_2R^{11}$, each of $R^5$, $R^7$ and $R^8$ is independently hydrogen, $C_{1-4}$ alkyl, $C_{1-4}$ alkoxy, $C_{1-4}$ alkoxycarbonyl, carboxyl, halo or hydroxyl and each of $R^9$, $R^{10}$, $R^{11}$, $R^{12}$, $R^{13}$, $R^{14}$, $R^{15}$, $R^{16}$ and $R^{17}$ is independently hydrogen or alkyl. Preferably, each of $R^5$, $R^7$ and $R^8$ is independently hydrogen or $C_{1-4}$ alkyl. More preferably, $R^5$, $R^7$ and $R^8$ are hydrogen. Preferably, each of $R^9$, $R^{10}$, $R^{11}$, $R^{12}$, $R^{13}$, $R^{14}$, $R^{15}$, $R^{16}$ and $R^{17}$ is independently hydrogen or $C_{1-4}$ alkyl.

In still other embodiments of a compound of Formula (I), n is 0, Y is a bond, A is $CR^4$, B is N, D is $CR^6$, E is $CR^7$, G is $CR^8$, $R^6$ is —$W[C(O)]_kZ(CR^9R^{10})_rCO_2R^{11}$, each of $R^4$, $R^7$ and $R^8$ is independently hydrogen, $C_{1-4}$ alkyl, $C_{1-4}$ alkoxy, $C_{1-4}$ alkoxycarbonyl, carboxyl, halo or hydroxyl and each of $R^9$, $R^{10}$, $R^{11}$, $R^{12}$, $R^{13}$, $R^{14}$, $R^{15}$, $R^{16}$ and $R^{17}$ is independently hydrogen or alkyl. Preferably, each of $R^4$, $R^7$ and $R^8$ is independently hydrogen or $C_{1-4}$ alkyl. More preferably, $R^5$, $R^7$ and $R^8$ are hydrogen. Preferably, each of $R^9$, $R^{10}$, $R^{11}$, $R^{12}$, $R^{13}$, $R^{14}$, $R^{15}$, $R^{16}$ and $R^{17}$ is independently hydrogen or $C_{1-4}$ alkyl.

In still other embodiments of a compound of Formula (I), n is 0, Y is a bond, A is N. B is $CR^5$, D is $CR^6$, E is $CR^7$, G is N, $R^6$ is —$W[C(O)]_kZ(CR^9R^{10})_rCO_2R^{11}$, each of $R^5$ and $R^7$ is independently hydrogen, $C_{1-4}$ alkyl, $C_{1-4}$ alkoxy, $C_{1-4}$ alkoxycarbonyl, carboxyl, halo or hydroxyl and each of $R^9$, $R^{10}$, $R^{11}$, $R^{12}$, $R^{13}$, $R^{14}$, $R^{15}$, $R^{16}$ and $R^{17}$ is independently hydrogen or alkyl. Preferably, each of $R^5$ and $R^7$ is independently hydrogen or $C_{1-4}$ alkyl. More preferably, $R^5$ and $R^7$ are hydrogen. Preferably, each of $R^9$, $R^{10}$, $R^{11}$, $R^{12}$, $R^{13}$, $R^{14}$, $R^{15}$, $R^{16}$ and $R^{17}$ is independently hydrogen or $C_{1-4}$ alkyl.

In still other embodiments of a compound of Formula (1), n is 0, Y is a bond. A is N, B is $CR^5$, D is $CR^6$, E is N, G is $CR^8$, $R^6$ is —W[C(O)]$_k$Z(CR$^9$R$^{10}$)$_r$CO$_2$R$^{11}$, each of $R^5$ and $R^8$ is independently hydrogen, $C_{1-4}$ alkyl, $C_{1-4}$ alkoxy, $C_{1-4}$ alkoxycarbonyl, carboxyl, halo or hydroxyl and each of $R^9$, $R^{10}$, $R^{11}$, $R^{12}$, $R^{13}$, $R^{14}$, $R^{15}$, $R^{16}$ and $R^{17}$ is independently hydrogen or alkyl. Preferably, each of $R^5$ and $R^8$ is independently hydrogen or $C_{1-4}$ alkyl. More preferably, $R^5$ and $R^8$ are hydrogen. Preferably, each of $R^9$, $R^{10}$, $R^{11}$, $R^{12}$, $R^{13}$, $R^{14}$, $R^{15}$, $R^{16}$ and $R^{17}$ is independently hydrogen or $C_{1-4}$ alkyl.

In still other embodiments of a compound of Formula (I), n is 0, Y is a bond, A is $CR^4$, B is N, D is $CR^6$, E is N, G is $CR^8$, $R^6$ is —W[C(O)]$_k$Z(CR$^9$R$^{10}$)$_r$CO$_2$R$^{11}$, each of $R^4$ and $R^8$ is independently hydrogen, $C_{1-4}$ alkyl, $C_{1-4}$ alkoxy, $C_{1-4}$ alkoxycarbonyl, carboxyl, halo or hydroxyl and each of $R^9$, $R^{10}$, $R^{11}$, $R^{12}$, $R^{13}$, $R^{14}$, $R^{15}R^{16}$ and $R^{17}$ is independently hydrogen or alkyl. Preferably, each of $R^4$ and $R^8$ is independently hydrogen or $C_{1-4}$ alkyl. More preferably, $R^4$ and $R^8$ are hydrogen. Preferably, each of $R^9$, $R^{10}$, $R^{11}$, $R^{12}$, $R^{13}$, $R^{14}$, $R^{15}$, $R^{16}$ and $R^{17}$ is independently hydrogen or $C_{1-4}$ alkyl.

In still other embodiments of a compound of Formula (I), n is 0, Y is a bond, A is N, B is $CR^5$, D is $CR^6$, E is $CR^7$, G is N, $R^6$ is —W[C(O)]$_k$Z(CR$^9$R$^{10}$)$_r$CO$_2$R$^{11}$, each of $R^5$ and $R^7$ is independently hydrogen, $C_{1-4}$ alkyl, $C_{1-4}$ alkoxy, $C_{1-4}$ alkoxycarbonyl, carboxyl, halo or hydroxyl and each of $R^9$, $R^{10}$, $R^{11}$, $R^{12}$, $R^{13}$, $R^{14}$, $R^{15}$, $R^{16}$ and $R^{17}$ is independently hydrogen or alkyl. Preferably, each of $R^5$ and $R^7$ is independently hydrogen or $C_{1-4}$ alkyl. More preferably, $R^5$ and $R^7$ are hydrogen. Preferably, each of $R^9$, $R^{10}$, $R^{11}$, $R^{12}$, $R^{13}$, $R^{14}$, $R^{15}$, $R^{16}$ and $R^{17}$ is independently hydrogen or $C_{1-4}$ alkyl.

In still other embodiments of a compound of Formula (I), n is 0, Y is O, A is $CR^4$, B is $CR^5$, D is $CR^6$, E is $CR^7$, G is $CR^8$, $R^4$ is —W[C(O)]$_k$Z(CR$^9$R$^{10}$)$_r$CO$_2$R$^{11}$, each of $R^5$, $R^6$, $R^7$ and $R^8$ is independently hydrogen, $C_{1-4}$ alkyl, $C_{1-4}$ alkoxy, $C_{1-4}$ alkoxycarbonyl, carboxyl, halo or hydroxyl and each of $R^9$, $R^{10}$, $R^{11}$, $R^{12}$, $R^{13}$, $R^{14}$, $R^{15}$, $R^{16}$ and $R^{17}$ is independently hydrogen or alkyl. Preferably, each of $R^5$, $R^6$, $R^7$ and $R^8$ is independently hydrogen or $C_{1-4}$ alkyl. More preferably, $R^5$, $R^6$, $R^7$ and $R^8$ are hydrogen. Preferably, each of $R^9$, $R^{10}$, $R^{11}$, $R^{12}$, $R^{13}$, $R^{14}$, $R^{15}$, $R^{16}$ and $R^{17}$ is independently hydrogen or $C_{1-4}$ alkyl.

In still other embodiments of a compound of Formula (I), n is 0, Y is O, A is $CR^4$, B is $CR^5$, D is $CR^6$, E is $CR^7$, G is $CR^8$, $R^4$ is —W[C(O)]$_k$Z(CR$^9$R$^{10}$)$_r$CO$_2$R$^{11}$, each of $R^5$, $R^6$, $R^7$ and $R^8$ is independently hydrogen, $C_{1-4}$ alkyl, $C_{1-4}$ alkoxy, $C_{1-4}$ alkoxycarbonyl, carboxyl, halo or hydroxyl, W is a bond, k is 1, Z is NR$^{17}$, r is 1, and each of $R^9$, $R^{10}$, $R^{11}$ and $R^{17}$ is independently hydrogen or $C_{1-4}$ alkyl. Preferably, each of $R^5$, $R^6$, $R^7$ and $R^8$ is independently hydrogen or $C_{1-4}$ alkyl. More preferably, $R^5$, $R^6$, $R^7$ and $R^8$ are hydrogen. Preferably, $R^{11}$ and $R^{17}$ are hydrogen.

In still other embodiments of a compound of Formula (I), n is 0, Y is O, A is $CR^4$, B is $CR^5$, D is $CR^6$, E is $CR^7$, G is $CR^8$, $R^4$ is —W[C(O)]$_k$Z(CR$^9$R$^{10}$)$_r$CO$_2$R$^{11}$, each of $R^5$, $R^6$, $R^7$ and $R^8$ is independently hydrogen, $C_{1-4}$ alkyl, $C_{1-4}$ alkoxy, $C_{1-4}$ alkoxycarbonyl, carboxyl, halo or hydroxyl, W is a bond, k is 1, Z is NR$^{17}$, r is 2, and each of $R^9$, $R^{10}$, $R^{11}$ and $R^{17}$ is independently hydrogen or $C_{1-4}$ alkyl. Preferably, each of $R^5$, $R^6$, $R^7$ and $R^8$ is independently hydrogen or $C_{1-4}$ alkyl. More preferably, $R^5$, $R^6$, $R^7$ and $R^8$ are hydrogen. Preferably, $R^{11}$ and $R^{17}$ are hydrogen.

In still other embodiments of a compound of Formula (I), n is 0, Y is O, A is $CR^4$, B is $CR^5$, D is $CR^6$, E is $CR^7$, G is $CR^8$, $R^4$ is —W[C(O)]$_k$Z(CR$^9$R$^{10}$)$_r$CO$_2$R$^{11}$, each of $R^5$, $R^6$, $R^7$ and $R^8$ is independently hydrogen, $C_{1-4}$ alkyl, $C_{1-4}$ alkoxy, $C_{1-4}$ alkoxycarbonyl, carboxyl, halo or hydroxyl, W is a bond, k is 1, Z is O, r is 1, and each of $R^9$, $R^{10}$ and $R^{11}$ is independently hydrogen or $C_{1-4}$ alkyl. Preferably, each of $R^5$, $R^6$, $R^7$ and $R^8$ is independently hydrogen or $C_{1-4}$ alkyl. More preferably, $R^5$, $R^6$, $R^7$ and $R^8$ are hydrogen. Preferably, $R^{11}$ is hydrogen.

In still other embodiments of a compound of Formula (I), n is 0, Y is O, A is $CR^4$, B is $CR^5$, D is $CR^6$, E is $CR^7$, G is $CR^8$, $R^4$ is —W[C(O)]$_k$Z(CR$^9$R$^{10}$)$_r$CO$_2$R$^{11}$, each of $R^5$, $R^6$, $R^7$ and $R^8$ is independently hydrogen, $C_{1-4}$ alkyl, $C_{1-4}$ alkoxy, $C_{1-4}$ alkoxycarbonyl, carboxyl, halo or hydroxyl, W is a bond, k is 1, Z is O, r is 2, and each of $R^9$, $R^{10}$ and $R^{11}$ is independently hydrogen or $C_{1-4}$ alkyl. Preferably, each of $R^5$, $R^6$, $R^7$ and $R^8$ is independently hydrogen or $C_{1-4}$ alkyl. More preferably, $R^5$, $R^6$, $R^7$ and $R^8$ are hydrogen. Preferably, $R^{11}$ is hydrogen.

In still other embodiments of a compound of Formula (I), n is 0, Y is O, A is $CR^4$, B is $CR^5$, D is $CR^6$, E is $CR^7$, G is $CR^8$, $R^4$ is —W[C(O)]$_k$Z(CR$^9$R$^{10}$)$_r$CO$_2$R$^{11}$, each of $R^5$, $R^6$, $R^7$ and $R^8$ is independently hydrogen, $C_{1-4}$ alkyl, $C_{1-4}$ alkoxy, $C_{1-4}$ alkoxycarbonyl, carboxyl, halo or hydroxyl, W is O, k is 1, Z is NR$^{17}$, r is 1, and each of $R^9$, $R^{10}$, $R^{11}$ and $R^{17}$ is independently hydrogen or $C_{1-4}$ alkyl. Preferably, each of $R^5$, $R^6$, $R^7$ and $R^8$ is independently hydrogen or $C_{1-4}$ alkyl. More preferably, $R^5$, $R^6$, $R^7$ and $R^8$ are hydrogen. Preferably, $R^{11}$ and $R^{17}$ are hydrogen.

In still other embodiments of a compound of Formula (I), n is 0, Y is O, A is $CR^4$, B is $CR^5$, D is $CR^6$, E is $CR^7$, G is $CR^8$, $R^4$ is —W[C(O)]$_k$Z(CR$^9$R$^{10}$)$_r$CO$_2$R$^{11}$, each of $R^5$, $R^6$, $R^7$ and $R^8$ is independently hydrogen, $C_{1-4}$ alkyl, $C_{1-4}$ alkoxy, $C_{1-4}$ alkoxycarbonyl, carboxyl, halo or hydroxyl, W is O, k is 1, Z is NR$^{17}$, r is 2, and each of $R^9$, $R^{10}$, $R^{11}$ and $R^{17}$ is independently hydrogen or $C_{1-4}$ alkyl. Preferably, each of $R^5$, $R^6$, $R^7$ and $R^8$ is independently hydrogen or $C_{1-4}$ alkyl. More preferably, $R^5$, $R^6$, $R^7$ and $R^8$ are hydrogen. Preferably, $R^{11}$ and $R^{17}$ are hydrogen.

In still other embodiments of a compound of Formula (I), n is 0, Y is O, A is $CR^4$, B is $CR^5$, D is $CR^6$, E is $CR^7$, G is $CR^8$, $R^4$ is —W[C(O)]$_k$Z(CR$^9$R$^{10}$)$_r$CO$_2$R$^{11}$, each of $R^5$, $R^6$, $R^7$ and $R^8$ is independently hydrogen, $C_{1-4}$ alkyl, $C_{1-4}$ alkoxy, $C_{1-4}$ alkoxycarbonyl, carboxyl, halo or hydroxyl, W is O, k is 1, Z is O, r is 1, and each of $R^9$, $R^{10}$ and $R^{11}$ is independently hydrogen or $C_{1-4}$ alkyl. Preferably, each of $R^5$, $R^6$, $R^7$ and $R^8$ is independently hydrogen or $C_{1-4}$ alkyl. More preferably, $R^5$, $R^6$, $R^7$ and $R^8$ are hydrogen. Preferably, $R^{11}$ is hydrogen.

In still other embodiments of a compound of Formula (I), n is 0, Y is O, A is $CR^4$, B is $CR^5$, D is $CR^6$, E is $CR^7$, G is $CR^8$, $R^4$ is —W[C(O)]$_k$Z(CR$^9$R$^{10}$)$_r$CO$_2$R$^{11}$, each of $R^5$, $R^6$, $R^7$ and $R^8$ is independently hydrogen, $C_{1-4}$ alkyl, $C_{1-4}$ alkoxy, $C_{1-4}$ alkoxycarbonyl, carboxyl, halo or hydroxyl, W is O, k is 1, Z is O, r is 2, and each of $R^9$, $R^{10}$ and $R^{11}$ is independently hydrogen or $C_{1-4}$ alkyl. Preferably, each of $R^5$, $R^6$, $R^7$ and $R^8$ is independently hydrogen or $C_{1-4}$ alkyl. More preferably, $R^5$, $R^6$, $R^7$ and $R^8$ are hydrogen. Preferably, $R^{11}$ is hydrogen.

In still other embodiments of a compound of Formula (I), n is 0, Y is O, A is $CR^4$, B is $CR^5$, D is $CR^6$, E is $CR^7$, G is $CR^8$, $R^4$ is —W[C(O)]$_k$Z(CR$^9$R$^{10}$)$_r$CO$_2$R$^{11}$, each of $R^5$, $R^6$, $R^7$ and $R^8$ is independently hydrogen, $C_{1-4}$ alkyl, $C_{1-4}$ alkoxy, $C_{1-4}$ alkoxycarbonyl, carboxyl, halo or hydroxyl, W is O, k is 1, Z is CR$^{15}$R$^{16}$, r is 1, and each of $R^9$, $R^{10}$, $R^{11}$, $R^{15}$ and $R^{16}$ is independently hydrogen or $C_{1-4}$ alkyl. Preferably, each of $R^5$, $R^6$, $R^7$ and $R^8$ is independently hydrogen or $C_{1-4}$ alkyl. More preferably, $R^5$, $R^6$, $R^7$ and $R^8$ are hydrogen. Preferably, $R^{11}$, $R^{15}$ and $R^{16}$ are hydrogen.

In still other embodiments of a compound of Formula (I), n is 0, Y is O, A is $CR^4$, B is $CR^5$, D is $CR^6$, E is $CR^7$, G is $CR^8$, $R^4$ is —W[C(O)]$_k$Z(CR$^9$R$^{10}$)$_r$CO$_2$R$^{11}$, each of $R^5$, $R^6$, $R^7$ and $R^8$ is independently hydrogen, $C_{1-4}$ alkyl, $C_{1-4}$ alkoxy, $C_{1-4}$ alkoxycarbonyl, carboxyl, halo or hydroxyl, W is O, k is 1, Z is CR$^{15}$R$^{16}$, r is 2, and each of $R^9$, $R^{10}$, $R^{11}$, $R^{15}$ and $R^{16}$ is independently hydrogen or $C_{1-4}$ alkyl. Preferably, each of $R^5$, $R^6$, $R^7$ and $R^8$ is independently hydrogen or $C_{1-4}$ alkyl. More preferably, $R^5$, $R^6$, $R^7$ and $R^8$ are hydrogen. Preferably, $R^{11}$, $R^{15}$ and $R^{16}$ are hydrogen.

In still other embodiments of a compound of Formula (I), n is 0, Y is O, A is $CR^4$, B is $CR^5$, D is $CR^6$, E is $CR^7$, G is $CR^8$, $R^4$ is —W[C(O)]$_k$Z(CR$^9$R$^{10}$)$_r$CO$_2$R$^{11}$, each of $R^5$, $R^6$, $R^7$ and $R^8$ is independently hydrogen, $C_{1-4}$ alkyl, $C_{1-4}$ alkoxy, $C_{1-4}$ alkoxycarbonyl, carboxyl, halo or hydroxyl, W is NR$^{14}$, k is 1, Z is NR$^{17}$, r is 1 and each of $R^9$, $R^{10}$, $R^{11}$, $R^{14}$ and $R^{17}$ is independently hydrogen or $C_{1-4}$ alkyl. Preferably, each of $R^5$, $R^6$, $R^7$ and $R^8$ is independently hydrogen or $C_{1-4}$ alkyl. More preferably, $R^5$, $R^6$, $R^7$ and $R^8$ are hydrogen. Preferably, $R^{11}$, $R^{14}$ and $R^{17}$ are hydrogen.

In still other embodiments of a compound of Formula (I), n is 0, Y is O, A is $CR^4$, B is $CR^5$, D is $CR^6$, E is $CR^7$, G is $CR^8$, $R^4$ is —W[C(O)]$_k$Z(CR$^9$R$^{10}$)$_r$CO$_2$R$^{11}$, each of $R^5$, $R^6$, $R^7$ and $R^8$ is independently hydrogen, $C_{1-4}$ alkyl, $C_{1-4}$ alkoxy, $C_{1-4}$ alkoxycarbonyl, carboxyl, halo or hydroxyl, W is NR$^{14}$, k is 1, Z is NR$^{17}$, r is 2 and each of $R^9$, $R^{10}$, $R^{11}$, $R^{14}$ and $R^{17}$ is independently hydrogen or $C_{1-4}$ alkyl. Preferably, each of $R^5$, $R^6$, $R^7$ and $R^8$ is independently hydrogen or $C_{1-4}$ alkyl. More preferably, $R^5$, $R^6$, $R^7$ and $R^8$ are hydrogen. Preferably, $R^{11}$, $R^{14}$ and $R^{17}$ are hydrogen.

In still other embodiments of a compound of Formula (I), n is 0, Y is O, A is $CR^4$, B is $CR^5$, D is $CR^6$, E is $CR^7$, G is $CR^8$, $R^4$ is —W[C(O)]$_k$Z(CR$^9$R$^{10}$)$_r$CO$_2$R$^{11}$, each of $R^5$, $R^6$, $R^7$ and $R^8$ is independently hydrogen, $C_{1-4}$ alkyl, $C_{1-4}$ alkoxy, $C_{1-4}$ alkoxycarbonyl, carboxyl, halo or hydroxyl, W is NR$^{14}$, k is 1, Z is O, r is 1, and each of $R^9$, $R^{10}$, $R^{11}$ and $R^{14}$ is independently hydrogen or $C_{1-4}$ alkyl. Preferably, each of $R^5$, $R^6$, $R^7$ and $R^8$ is independently hydrogen or $C_{1-4}$ alkyl. More preferably, $R^5$, $R^6$, $R^7$ and $R^8$ are hydrogen. Preferably, each of $R^{11}$ and $R^{14}$ are hydrogen.

In still other embodiments of a compound of Formula (I), n is 0, Y is O, A is $CR^4$, B is $CR^5$, D is $CR^6$, E is $CR^7$, G is $CR^8$, $R^4$ is —W[C(O)]$_k$Z(CR$^9$R$^{10}$)$_r$CO$_2$R$^{11}$, each of $R^5$, $R^6$, $R^7$ and $R^8$ is independently hydrogen, $C_{1-4}$ alkyl, $C_{1-4}$ alkoxy, $C_{1-4}$ alkoxycarbonyl, carboxyl, halo or hydroxyl, W is NR$^{14}$, k is 1, Z is O, r is 2, and each of $R^9$, $R^{10}$, $R^{11}$ and $R^{14}$ is independently hydrogen or $C_{1-4}$ alkyl. Preferably, each of $R^5$, $R^6$, $R^7$ and $R^8$ is independently hydrogen or $C_{1-4}$ alkyl. More preferably, $R^5$, $R^6$, $R^7$ and $R^8$ are hydrogen. Preferably, each of $R^{11}$ and $R^{14}$ are hydrogen.

In still other embodiments of a compound of Formula (I), n is 0, Y is O, A is $CR^4$, B is $CR^5$, D is $CR^6$, E is $CR^7$, G is $CR^8$, $R^4$ is —W[C(O)]$_k$Z(CR$^9$R$^{10}$)$_r$CO$_2$R$^{11}$, each of $R^5$, $R^6$, $R^7$ and $R^8$ is independently hydrogen, $C_{1-4}$ alkyl, $C_{1-4}$ alkoxy, $C_{1-4}$ alkoxycarbonyl, carboxyl, halo or hydroxyl, W is NR$^{14}$, k is 1, Z is CR$^{15}$R$^{16}$, r is 1, and each of $R^9$, $R^{10}$, $R^{11}$, $R^{14}$, $R^{15}$ and $R^{16}$ is independently hydrogen or $C_{1-4}$ alkyl. Preferably, each of $R^5$, $R^6$, $R^7$ and $R^8$ is independently hydrogen or $C_{1-4}$ alkyl. More preferably, $R^5$, $R^6$, $R^7$ and $R^8$ are hydrogen. Preferably, $R^{11}$, $R^{14}$, $R^{15}$ and $R^{16}$ are hydrogen.

In still other embodiments of a compound of Formula (I), n is 0, Y is O, A is $CR^4$, B is $CR^5$, D is $CR^6$, E is $CR^7$, G is $CR^8$, $R^4$ is —W[C(O)]$_k$Z(CR$^9$R$^{10}$)$_r$CO$_2$R$^{11}$, each of $R^5$, $R^6$, $R^7$ and $R^8$ is independently hydrogen, $C_{1-4}$ alkyl, $C_{1-4}$ alkoxycarbonyl, carboxyl, halo or hydroxyl, W is NR$^{14}$, k is 1, Z is CR$^{15}$R$^{16}$, r is 2, and each of $R^9$, $R^{10}$, $R^{11}$, $R^{14}$, $R^{15}$ and $R^{16}$ is independently hydrogen or $C_{1-4}$ alkyl. Preferably, each of $R^5$, $R^6$, $R^7$ and $R^8$ is independently hydrogen or $C_{1-4}$ alkyl. More preferably, $R^5$, $R^6$, $R^7$ and $R^8$ are hydrogen. Preferably, $R^{11}$, $R^{14}$, $R^{15}$ and $R^{16}$ are hydrogen.

In still other embodiments of a compound of Formula (I), n is 0, Y is O, A is $CR^4$, B is $CR^5$, D is $CR^6$, E is $CR^7$, G is $CR^8$, $R^5$ is —W[C(O)]$_k$Z(CR$^9$R$^{10}$)$_r$CO$_2$R$^{11}$, each of $R^4$, $R^6$, $R^7$ and $R^8$ is independently hydrogen, $C_{1-4}$ alkyl, $C_{1-4}$ alkoxy, $C_{1-4}$ alkoxycarbonyl, carboxyl, halo or hydroxyl and each of $R^9$, $R^{10}$, $R^{11}$, $R^{12}$, $R^{13}$, $R^{14}$, $R^{15}$, $R^{16}$ and $R^{17}$ is independently hydrogen or alkyl. Preferably, each of $R^4$, $R^6$, $R^7$ and $R^8$ is independently hydrogen or $C_{1-4}$ alkyl. More preferably, $R^4$, $R^6$, $R^7$ and $R^8$ are hydrogen. Preferably, each of $R^9$, $R^{10}$, $R^{11}$, $R^{12}$, $R^{13}$, $R^{14}$, $R^{15}$, $R^{16}$ and $R^{17}$ is independently hydrogen or $C_{1-4}$ alkyl.

In still other embodiments of a compound of Formula (I), n is 0, Y is O, A is $CR^4$, B is $CR^5$, D is $CR^6$, E is $CR^7$, G is $CR^8$, $R^5$ is —W[C(O)]$_k$Z(CR$^9$R$^{10}$)$_r$CO$_2$R$^{11}$, each of $R^4$, $R^6$, $R^7$ and $R^8$ is independently hydrogen, $C_{1-4}$ alkyl, $C_{1-4}$ alkoxy, $C_{1-4}$ alkoxycarbonyl, carboxyl, halo or hydroxyl, W is a bond, k is 1, Z is NR$^{17}$, r is 1, and each of $R^9$, $R^{10}$, $R^{11}$ and $R^{17}$ is independently hydrogen or $C_{1-4}$ alkyl. Preferably, each of $R^4$, $R^6$, $R^7$ and $R^8$ is independently hydrogen or $C_{1-4}$ alkyl. More preferably, $R^4$, $R^6$, $R^7$ and $R^8$ are hydrogen. Preferably, $R^{11}$ and $R^{17}$ are hydrogen.

In still other embodiments of a compound of Formula (I), n is 0, Y is O, A is $CR^4$, B is $CR^5$, D is $CR^6$, E is $CR^7$, G is $CR^8$, $R^5$ is —W[C(O)]$_k$Z(CR$^9$R$^{10}$)$_r$CO$_2$R$^{11}$, each of $R^4$, $R^6$, $R^7$ and $R^8$ is independently hydrogen, $C_{1-4}$ alkyl, $C_{1-4}$ alkoxy, $C_{1-4}$ alkoxycarbonyl, carboxyl, halo or hydroxyl, W is a bond, k is 1, Z is NR$^{17}$, r is 2, and each of $R^9$, $R^{10}$, $R^{11}$ and $R^{17}$ is independently hydrogen or $C_{1-4}$ alkyl. Preferably, each of $R^4$, $R^6$, $R^7$ and $R^8$ is independently hydrogen or $C_{1-4}$ alkyl. More preferably, $R^4$, $R^6$, $R^7$ and $R^8$ are hydrogen. Preferably, $R^{11}$ and $R^{17}$ are hydrogen.

In still other embodiments of a compound of Formula (I), n is 0, Y is O, A is $CR^4$, B is $CR^5$, D is $CR^6$, E is $CR^7$, G is $CR^8$, $R^5$ is —W[C(O)]$_k$Z(CR$^9$R$^{10}$)$_r$CO$_2$R$^{11}$, each of $R^4$, $R^6$, $R^7$ and $R^8$ is independently hydrogen, $C_{1-4}$ alkyl, $C_{1-4}$ alkoxy, $C_{1-4}$ alkoxycarbonyl, carboxyl, halo or hydroxyl, W is a bond, k is 1, Z is O, r is 1, and each of $R^9$, $R^{10}$ and $R^{11}$ is independently hydrogen or $C_{1-4}$ alkyl. Preferably, each of $R^4$, $R^6$, $R^7$ and $R^8$ is independently hydrogen or $C_{1-4}$ alkyl. More preferably, each of $R^5$, $R^6$, $R^7$ and $R^8$ is hydrogen. Preferably, $R^{11}$ is hydrogen.

In still other embodiments of a compound of Formula (I), n is 0, Y is O, A is $CR^4$, B is $CR^5$, D is $CR^6$, E is $CR^7$, G is $CR^8$, $R^5$ is —W[C(O)]$_k$Z(CR$^9$R$^{10}$)$_r$CO$_2$R$^{11}$, each of $R^4$, $R^6$, $R^7$ and $R^8$ is independently hydrogen, $C_{1-4}$ alkyl, $C_{1-4}$ alkoxy, $C_{1-4}$ alkoxycarbonyl, carboxyl, halo or hydroxyl, W is a bond, k is 1, Z is O, r is 2, and each of $R^9$, $R^{10}$ and $R^{11}$ is independently hydrogen or $C_{1-4}$ alkyl. Preferably, each of $R^4$, $R^6$, $R^7$ and $R^8$ is independently hydrogen or $C_{1-4}$ alkyl. More preferably, $R^4$, $R^6$, $R^7$ and $R^8$ are hydrogen. Preferably, $R^{11}$ is hydrogen.

In still other embodiments of a compound of Formula (I), n is 0, Y is O, A is $CR^4$, B is $CR^5$, D is $CR^6$, E is $CR^7$, G is $CR^8$, $R^5$ is —W[C(O)]$_k$Z(CR$^9$R$^{10}$)$_r$CO$_2$R$^{11}$, each of $R^4$, $R^6$, $R^7$ and $R^8$ is independently hydrogen, $C_{1-4}$ alkyl, $C_{1-4}$ alkoxycarbonyl, carboxyl, halo or hydroxyl, W is O, k is 1, Z is NR$^{17}$, r is 1, and each of $R^9$, $R^{10}$, $R^{11}$ and $R^{17}$ is independently hydrogen or $C_{1-4}$ alkyl. Preferably, each of $R^4$, $R^6$, $R^7$ and $R^8$ is independently hydrogen or $C_{1-4}$ alkyl. More preferably, $R^5$, $R^6$, $R^7$ and $R^8$ are hydrogen. Preferably, $R^{11}$ and $R^{17}$ are hydrogen.

In still other embodiments of a compound of Formula (I), n is 0, Y is O, A is $CR^4$, B is $CR^5$, D is $CR^6$, E is $CR^7$, G is $CR^8$, $R^5$ is $—W[C(O)]_kZ(CR^9R^{10})_rCO_2R^{11}$, each of $R^4$, $R^6$, $R^7$ and $R^8$ is independently hydrogen, $C_{1-4}$ alkyl, $C_{1-4}$ alkoxy, $C_{1-4}$ alkoxycarbonyl, carboxyl, halo or hydroxyl, W is O, k is 1, Z is $NR^{17}$, r is 2, and each of $R^9$, $R^{10}$, $R^{11}$ and $R^{17}$ is independently hydrogen or $C_{1-4}$ alkyl. Preferably, each of $R^4$, $R^6$, $R^7$ and $R^8$ is independently hydrogen or $C_{1-4}$ alkyl. More preferably, $R^4$, $R^6$, $R^7$ and $R^8$ are hydrogen. Preferably, $R^{11}$ and $R^{17}$ are hydrogen.

In still other embodiments of a compound of Formula (I), n is 0, Y is O, A is $CR^4$, B is $CR^5$, D is $CR^6$, E is $CR^7$, G is $CR^8$, $R^5$ is $—W[C(O)]_kZ(CR^9R^{10})_rCO_2R^{11}$, each of $R^4$, $R^6$, $R^7$ and $R^8$ is independently hydrogen, $C_{1-4}$ alkyl, $C_{1-4}$ alkoxy, $C_{1-4}$ alkoxycarbonyl, carboxyl, halo or hydroxyl, W is O, k is 1, Z is O, r is 1, and each of $R^9$, $R^{10}$ and $R^{11}$ is independently hydrogen or $C_{1-4}$ alkyl. Preferably, each of $R^4$, $R^6$, $R^7$ and $R^8$ is independently hydrogen or $C_{1-4}$ alkyl. More preferably, each of $R^4$, $R^6$, $R^7$ and $R^8$ is hydrogen. Preferably, $R^{11}$ is hydrogen.

In still other embodiments of a compound of Formula (I), n is 0, Y is O, A is $CR^4$, B is $CR^5$, D is $CR^6$, E is $CR^7$, G is $CR^8$, $R^5$ is $—W[C(O)]_kZ(CR^9R^{10})_rCO_2R^{11}$, each of $R^4$, $R^6$, $R^7$ and $R^8$ is independently hydrogen, $C_{1-4}$ alkyl, $C_{1-4}$ alkoxy, $C_{1-4}$ alkoxycarbonyl, carboxyl, halo or hydroxyl, W is O, k is 1, Z is O, r is 2, and each of $R^9$, $R^{10}$ and $R^{11}$ is independently hydrogen or $C_{1-4}$ alkyl. Preferably, each of $R^4$, $R^6$, $R^7$ and $R^8$ is independently hydrogen or $C_{1-4}$ alkyl. More preferably, each of $R^4$, $R^6$, $R^7$ and $R^8$ is hydrogen. Preferably, $R^{11}$ is hydrogen.

In still other embodiments of a compound of Formula (I), n is 0, Y is O, A is $CR^4$, B is $CR^5$, D is $CR^6$, E is $CR^7$, G is $CR^8$, $R^5$ is $—W[C(O)]_kZ(CR^9R^{10})_rCO_2R^{11}$, each of $R^4$, $R^6$, $R^7$ and $R^8$ is independently hydrogen, $C_{1-4}$ alkyl, $C_{1-4}$ alkoxy, $C_{1-4}$ alkoxycarbonyl, carboxyl, halo or hydroxyl, W is O, k is 1, Z is $CR^{15}R^{16}$, r is 1, and each of $R^9$, $R^{10}$, $R^{11}$, $R^{15}$ and $R^{16}$ is independently hydrogen or $C_{1-4}$ alkyl. Preferably, each of $R^4$, $R^6$, $R^7$ and $R^8$ is independently hydrogen or $C_{1-4}$ alkyl. More preferably, $R^4$, $R^6$, $R^7$ and $R^8$ are hydrogen. Preferably, $R^{11}$, $R^{15}$ and $R^{16}$ are hydrogen.

In still other embodiments of a compound of Formula (I), n is 0, Y is O, A is $CR^4$, B is $CR^5$, D is $CR^6$, E is $CR^7$, G is $CR^8$, $R^5$ is $—W[C(O)]_kZ(CR^9R^{10})_rCO_2R^{11}$, each of $R^4$, $R^6$, $R^7$ and $R^8$ is independently hydrogen, $C_{1-4}$ alkyl, $C_{1-4}$ alkoxy, $C_{1-4}$ alkoxycarbonyl, carboxyl, halo or hydroxyl, W is O, k is 1, Z is $CR^{15}R^{16}$, r is 2, and each of $R^9$, $R^{10}$, $R^{11}$, $R^{15}$ and $R^{16}$ is independently hydrogen or $C_{1-4}$ alkyl. Preferably, each of $R^4$, $R^6$, $R^7$ and $R^8$ is independently hydrogen or $C_{1-4}$ alkyl. More preferably, $R^4$, $R^6$, $R^7$ and $R^8$ are hydrogen. Preferably, $R^{11}$, $R^{15}$ and $R^{16}$ are hydrogen.

In still other embodiments of a compound of Formula (I), n is 0, Y is O, A is $CR^4$, B is $CR^5$, D is $CR^6$, E is $CR^7$, G is $CR^8$, $R^5$ is $—W[C(O)]_kZ(CR^9R^{10})_rCO_2R^{11}$, each of $R^4$, $R^6$, $R^7$ and $R^8$ is independently hydrogen, $C_{1-4}$ alkyl, $C_{1-4}$ alkoxy, $C_{1-4}$ alkoxycarbonyl, carboxyl, halo or hydroxyl, W is $NR^{14}$ k is 1, Z is $NR^{17}$, r is 1 and each of $R^9$, $R^{10}$, $R^{11}$, $R^{14}$ and $R^{17}$ is independently hydrogen or $C_{1-4}$ alkyl. Preferably, each of $R^4$, $R^6$, $R^7$ and $R^8$ is independently hydrogen or $C_{1-4}$ alkyl. More preferably, $R^4$, $R^6$, $R^7$ and $R^8$ are hydrogen. Preferably, $R^{11}$, $R^{14}$ and $R^{17}$ are hydrogen.

In still other embodiments of a compound of Formula (I), n is 0, Y is O, A is $CR^4$, B is $CR^5$, D is $CR^6$, E is $CR^7$, G is $CR^8$, $R^5$ is $—W[C(O)]_kZ(CR^9R^{10})_rCO_2R^{11}$, each of $R^4$, $R^6$, $R^7$ and $R^8$ is independently hydrogen, $C_{1-4}$ alkyl, $C_{1-4}$ alkoxy, $C_{1-4}$ alkoxycarbonyl, carboxyl, halo or hydroxyl, W is $NR^{14}$, k is 1, Z is $NR^{17}$, r is 2 and each of $R^9$, $R^{10}$, $R^{11}$, $R^{14}$ and $R^{17}$ is independently hydrogen or $C_{1-4}$ alkyl. Preferably, each of $R^4$, $R^6$, $R^7$ and $R^8$ is independently hydrogen or $C_{1-4}$ alkyl. More preferably, $R^4$, $R^6$, $R^7$ and $R^8$ are hydrogen. Preferably, $R^{11}$, $R^{14}$ and $R^{17}$ are hydrogen.

In still other embodiments of a compound of Formula (I), n is 0, Y is O, A is $CR^4$, B is $CR^5$, D is $CR^6$, E is $CR^7$, G is $CR^8$, $R^5$ is $—W[C(O)]_kZ(CR^9R^{10})_rCO_2R^{11}$, each of $R^4$, $R^6$, $R^7$ and $R^8$ is independently hydrogen, $C_{1-4}$ alkyl, $C_{1-4}$ alkoxy, $C_{1-4}$ alkoxycarbonyl, carboxyl, halo or hydroxyl, W is $NR^{14}$, k is 1, Z is O, r is 1, and each of $R^9$, $R^{10}$, $R^{11}$ and $R^{14}$ is independently hydrogen or $C_{1-4}$ alkyl. Preferably, each of $R^4$, $R^6$, $R^7$ and $R^8$ is independently hydrogen or $C_{1-4}$ alkyl. More preferably, $R^4$, $R^6$, $R^7$ and $R^8$ are hydrogen. Preferably, each of $R^{11}$ and $R^{14}$ are hydrogen.

In still other embodiments of a compound of Formula (I), n is 0, Y is O, A is $CR^4$, B is $CR^5$, D is $CR^6$, E is $CR^7$, G is $CR^8$, $R^5$ is $—W[C(O)]_kZ(CR^9R^{10})_rCO_2R^{11}$, each of $R^4$, $R^6$, $R^7$ and $R^8$ is independently hydrogen, $C_{1-4}$ alkyl, $C_{1-4}$ alkoxy, $C_{1-4}$ alkoxycarbonyl, carboxyl, halo or hydroxyl, W is $NR^{14}$, k is 1, Z is O, r is 2, and each of $R^9$, $R^{10}$, $R^{11}$ and $R^{14}$ is independently hydrogen or $C_{1-4}$ alkyl. Preferably, each of $R^4$, $R^6$, $R^7$ and $R^8$ is independently hydrogen or $C_{1-4}$ alkyl. More preferably, $R^4$, $R^6$, $R^7$ and $R^8$ are hydrogen. Preferably, each of $R^{11}$ and $R^{14}$ are hydrogen.

In still other embodiments of a compound of Formula (I), n is 0, Y is O, A is $CR^4$, B is $CR^5$, D is $CR^6$, E is $CR^7$, G is $CR^8$, $R^5$ is $—W[C(O)]_kZ(CR^9R^{10})_rCO_2R^{11}$, each of $R^4$, $R^6$, $R^7$ and $R^8$ is independently hydrogen, $C_{1-4}$ alkyl, $C_{1-4}$ alkoxy, $C_{1-4}$ alkoxycarbonyl, carboxyl, halo or hydroxyl, W is $NR^{14}$, k is 1, Z is $CR^{15}R^{16}$, r is 1, and each of $R^9$, $R^{10}$, $R^{11}$, $R^{14}$, $R^{15}$ and $R^{16}$ is independently hydrogen or $C_{1-4}$ alkyl. Preferably, each of $R^4$, $R^6$, $R^7$ and $R^8$ is independently hydrogen or $C_{1-4}$ alkyl. More preferably, $R^4$, $R^6$, $R^7$ and $R^8$ are hydrogen. Preferably, $R^{11}$, $R^{14}$, $R^{15}$ and $R^{16}$ are hydrogen.

In still other embodiments of a compound of Formula (I), n is 0, Y is O, A is $CR^4$, B is $CR^5$, D is $CR^6$, E is $CR^7$, G is $CR^8$, $R^5$ is $—W[C(O)]_kZ(CR^9R^{10})_rCO_2R^{11}$, each of $R^4$, $R^6$, $R^7$ and $R^8$ is independently hydrogen, $C_{1-4}$ alkyl, $C_{1-4}$ alkoxy, $C_{1-4}$ alkoxycarbonyl, carboxyl, halo or hydroxyl, W is $NR^{14}$, k is 1, Z is $CR^{15}R^{16}$, r is 2, and each of $R^9$, $R^{10}$, $R^{11}$, $R^{14}$, $R^{15}$ and $R^{16}$ is independently hydrogen or $C_{1-4}$ alkyl. Preferably, each of $R^4$, $R^6$, $R^7$ and $R^8$ is independently hydrogen or $C_{1-4}$ alkyl. More preferably, $R^4$, $R^6$, $R^7$ and $R^8$ are hydrogen. Preferably, $R^{11}$, $R^{14}$, $R^{15}$ and $R^{16}$ are hydrogen.

In still other embodiments of a compound of Formula (I), n is 0, Y is O, A is $CR^4$, B is $CR^5$, D is $CR^6$, E is $CR^7$, G is $CR^8$, $R^6$ is $—W[C(O)]_kZ(CR^9R^{10})_rCO_2R^{11}$, each of $R^4$, $R^5$, $R^7$ and $R^8$ is independently hydrogen, $C_{1-4}$ alkyl, $C_{1-4}$ alkoxy, $C_{1-4}$ alkoxycarbonyl, carboxyl, halo or hydroxyl and each of $R^9$, $R^{10}$, $R^{11}$, $R^{12}$, $R^{13}$, $R^{14}$ $R^{15}$, $R^{16}$ and $R^{17}$ is independently hydrogen or alkyl. Preferably, each of $R^4$, $R^5$, $R^7$ and $R^8$ is independently hydrogen or $C_{1-4}$ alkyl. More preferably, $R^4$, $R^5$, $R^7$ and $R^8$ are hydrogen. Preferably, each of $R^9$, $R^{10}$, $R^{11}$, $R^{12}$, $R^{13}$, $R^{14}$, $R^{15}$, $R^{16}$ and $R^{17}$ is independently hydrogen or $C_{1-4}$ alkyl.

In still other embodiments of a compound of Formula (I), n is 0, Y is O, A is $CR^4$, B is $CR^5$, D is $CR^6$, E is $CR^7$, G is $CR^8$, $R^6$ is $—W[C(O)]_kZ(CR^9R^{10})_rCO_2R^{11}$, each of $R^4$, $R^5$, $R^7$ and $R^8$ is independently hydrogen, $C_{1-4}$ alkyl, $C_{1-4}$ alkoxy, $C_{1-4}$ alkoxycarbonyl, carboxyl, halo or hydroxyl, W is a bond, k is 1, Z is $NR^{17}$, r is 1, and each of $R^9$, $R^{10}$, $R^{11}$ and $R^{17}$ is independently hydrogen or $C_{1-4}$ alkyl. Preferably, each of $R^4$, $R^5$, $R^7$ and $R^8$ is independently hydrogen or $C_{1-4}$ alkyl. More preferably, $R^4$, $R^5$, $R^7$ and $R^8$ are hydrogen. Preferably, $R^{11}$ and $R^{17}$ are hydrogen.

In still other embodiments of a compound of Formula (I), n is 0, Y is O, A is $CR^4$, B is $CR^5$, D is $CR^6$, E is $CR^7$, G is $CR^8$, $R^6$ is —W[C(O)]$_k$Z(CR$^9$R$^{10}$)$_r$CO$_2$R$^{11}$, each of $R^4$, $R^5$, $R^7$ and $R^8$ is independently hydrogen, $C_{1-4}$ alkyl, $C_{1-4}$ alkoxy, $C_{1-4}$ alkoxycarbonyl, carboxyl, halo or hydroxyl, W is a bond, k is 1, Z is $NR^{17}$, r is 2, and each of $R^9$, $R^{10}$, $R^{11}$ and $R^{17}$ is independently hydrogen or $C_{1-4}$ alkyl. Preferably, each of $R^4$, $R^5$, $R^7$ and $R^8$ is independently hydrogen or $C_{1-4}$ alkyl. More preferably, $R^4$, $R^5$, $R^7$ and $R^8$ are hydrogen. Preferably, $R^{11}$ and $R^{17}$ are hydrogen.

In still other embodiments of a compound of Formula (I), n is 0, Y is O, A is $CR^4$, B is $CR^5$, D is $CR^6$, E is $CR^7$, G is $CR^8$, $R^6$ is —W[C(O)]$_k$Z(CR$^9$R$^{10}$)$_r$CO$_2$R$^{11}$, each of $R^4$, $R^5$, $R^7$ and $R^8$ is independently hydrogen, $C_{1-4}$ alkyl, $C_{1-4}$ alkoxy, $C_{1-4}$ alkoxycarbonyl, carboxyl, halo or hydroxyl, W is a bond, k is 1, Z is O, r is 1, and each of $R^9$, $R^{10}$ and $R^{11}$ is independently hydrogen or $C_{1-4}$ alkyl. Preferably, each of $R^4$, $R^5$, $R^7$ and $R^8$ is independently hydrogen or $C_{1-4}$ alkyl. More preferably, $R^4$, $R^5$, $R^7$ and $R^8$ are hydrogen. Preferably, $R^{11}$ is hydrogen.

In still other embodiments of a compound of Formula (I), n is 0, Y is O, A is $CR^4$, B is $CR^5$, D is $CR^6$, E is $CR^7$, G is $CR^8$, $R^6$ is —W[C(O)]$_k$Z(CR$^9$R$^{10}$)$_r$CO$_2$R$^{11}$, each of $R^4$, $R^5$, $R^7$ and $R^8$ is independently hydrogen, $C_{1-4}$ alkyl, $C_{1-4}$ alkoxy, $C_{1-4}$ alkoxycarbonyl, carboxyl, halo or hydroxyl, W is a bond, k is 1, Z is O, r is 2, and each of $R^9$, $R^{10}$ and $R^{11}$ is independently hydrogen or $C_{1-4}$ alkyl. Preferably, each of $R^4$, $R^5$, $R^7$ and $R^8$ is independently hydrogen or $C_{1-4}$ alkyl. More preferably, $R^4$, $R^5$, $R^7$ and $R^8$ are hydrogen. Preferably, $R^{11}$ is hydrogen.

In still other embodiments of a compound of Formula (I), n is 0, Y is O, A is $CR^4$, B is $CR^5$, D is $CR^6$, E is $CR^7$, G is $CR^8$, $R^6$ is —W[C(O)]$_k$Z(CR$^9$R$^{10}$)$_r$CO$_2$R$^{11}$, each of $R^4$, $R^5$, $R^7$ and $R^8$ is independently hydrogen, $C_{1-4}$ alkyl, $C_{1-4}$ alkoxy, $C_{1-4}$ alkoxycarbonyl, carboxyl, halo or hydroxyl, W is O, k is 1, Z is $NR^{17}$, r is 1, and each of $R^9$, $R^{10}$, $R^{11}$ and $R^{17}$ is independently hydrogen or $C_{1-4}$ alkyl. Preferably, each of $R^4$, $R^5$, $R^7$ and $R^8$ is independently hydrogen or $C_{1-4}$ alkyl. More preferably, $R^4$, $R^5$, $R^7$ and $R^8$ are hydrogen. Preferably, $R^{11}$ and $R^{17}$ are hydrogen.

In still other embodiments of a compound of Formula (I), n is 0, Y is O, A is $CR^4$, B is $CR^5$, D is $CR^6$, E is $CR^7$, G is $CR^8$, $R^6$ is —W[C(O)]$_k$Z(CR$^9$R$^{10}$)$_r$CO$_2$R$^{11}$, each of $R^4$, $R^5$, $R^7$ and $R^8$ is independently hydrogen, $C_{1-4}$ alkyl, $C_{1-4}$ alkoxy, $C_{1-4}$ alkoxycarbonyl, carboxyl, halo or hydroxyl, W is O, k is 1, Z is $NR^{17}$, r is 2, and each of $R^9$, $R^{10}$, $R^{11}$ and $R^{17}$ is independently hydrogen or $C_{1-4}$ alkyl. Preferably, each of $R^4$, $R^5$, $R^7$ and $R^8$ is independently hydrogen or $C_{1-4}$ alkyl. More preferably, $R^4$, $R^5$, $R^7$ and $R^8$ are hydrogen. Preferably, $R^{11}$ and $R^{17}$ are hydrogen.

In still other embodiments of a compound of Formula (I), n is 0, Y is O, A is $CR^4$, B is $CR^5$, D is $CR^6$, E is $CR^7$, G is $CR^8$, $R^6$ is —W[C(O)]$_k$Z(CR$^9$R$^{10}$)$_r$CO$_2$R$^{11}$, each of $R^4$, $R^5$, $R^7$ and $R^8$ is independently hydrogen, $C_{1-4}$ alkyl, $C_{1-4}$ alkoxy, $C_{1-4}$ alkoxycarbonyl, carboxyl, halo or hydroxyl, W is O, k is 1, Z is O, r is 1, and each of $R^9$, $R^{10}$ and $R^{11}$ is independently hydrogen or $C_{1-4}$ alkyl. Preferably, each of $R^4$, $R^5$, $R^7$ and $R^8$ is independently hydrogen or $C_{1-4}$ alkyl. More preferably, $R^4$, $R^5$, $R^7$ and $R^8$ are hydrogen. Preferably, $R^{11}$ is hydrogen.

In still other embodiments of a compound of Formula (I), n is 0, Y is O, A is $CR^4$, B is $CR^5$, D is $CR^6$, E is $CR^7$, G is $CR^8$, $R^6$ is —W[C(O)]$_k$Z(CR$^9$R$^{10}$)$_r$CO$_2$R$^{11}$, each of $R^4$, $R^5$, $R^7$ and $R^8$ is independently hydrogen or $C_{1-4}$ alkyl. Preferably, each of $R^4$, $R^5$, $R^7$ and $R^8$ is independently hydrogen or $C_{1-4}$ alkyl. More preferably, $R^4$, $R^5$, $R^7$ and $R^8$ are hydrogen. Preferably, $R^{11}$ is hydrogen.

In still other embodiments of a compound of Formula (I), n is 0, Y is O, A is $CR^4$, B is $CR^5$, D is $CR^6$, E is $CR^7$, G is $CR^8$, $R^6$ is —W[C(O)]$_k$Z(CR$^9$R$^{10}$)$_r$CO$_2$R$^{11}$, each of $R^4$, $R^5$, $R^7$ and $R^8$ is independently hydrogen, $C_{1-4}$ alkyl, $C_{1-4}$ alkoxy, $C_{1-4}$ alkoxycarbonyl, carboxyl, halo or hydroxyl, W is O, k is 1, Z is $CR^{15}R^{16}$, r is 1, and each of $R^9$, $R^{10}$, $R^{11}$, $R^{15}$ and $R^{16}$ is independently hydrogen or $C_{1-4}$ alkyl. Preferably, each of $R^4$, $R^5$, $R^7$ and $R^8$ is independently hydrogen or $C_{1-4}$ alkyl. More preferably, $R^4$, $R^5$, $R^7$ and $R^8$ are hydrogen. Preferably, $R^{11}$, $R^{15}$ and $R^{16}$ are hydrogen.

In still other embodiments of a compound of Formula (I), n is 0, Y is O, A is $CR^4$, B is $CR^5$, D is $CR^6$, E is $CR^7$, G is $CR^8$, $R^6$ is —W[C(O)]$_k$Z(CR$^9$R$^{10}$)$_r$CO$_2$R$^{11}$, each of $R^4$, $R^5$, $R^7$ and $R^8$ is independently hydrogen, $C_{1-4}$ alkyl, $C_{1-4}$ alkoxy, $C_{1-4}$ alkoxycarbonyl, carboxyl, halo or hydroxyl, W is O, k is 1, Z is $CR^{15}R^{16}$, r is 2, and each of $R^9$, $R^{10}$, $R^{11}$, $R^{15}$ and $R^{16}$ is independently hydrogen or $C_{1-4}$ alkyl. Preferably, each of $R^4$, $R^5$, $R^7$ and $R^8$ is independently hydrogen or $C_{1-4}$ alkyl. More preferably, $R^4$, $R^5$, $R^7$ and $R^8$ are hydrogen. Preferably, $R^{11}$, $R^{15}$ and $R^{16}$ are hydrogen.

In still other embodiments of a compound of Formula (I), n is 0, Y is O, A is $CR^4$, B is $CR^5$, D is $CR^6$, E is $CR^7$, G is $CR^8$, $R^6$ is —W[C(O)]$_k$Z(CR$^9$R$^{10}$)$_r$CO$_2$R$^{11}$, each of $R^4$, $R^5$, $R^7$ and $R^8$ is independently hydrogen, $C_{1-4}$ alkyl, $C_{1-4}$ alkoxy, $C_{1-4}$ alkoxycarbonyl, carboxyl, halo or hydroxyl, W is $NR^{14}$, k is 1, Z is $NR^{17}$, r is 1 and each of $R^9$, $R^{10}$, $R^{11}$, $R^{14}$ and $R^{17}$ is independently hydrogen or $C_{1-4}$ alkyl. Preferably, each of $R^4$, $R^5$, $R^7$ and $R^8$ is independently hydrogen or $C_{1-4}$ alkyl. More preferably, $R^4$, $R^5$, $R^7$ and $R^8$ are hydrogen. Preferably, $R^{11}$, $R^{14}$ and $R^{17}$ are hydrogen.

In still other embodiments of a compound of Formula (I), n is 0, Y is O, A is $CR^4$, B is $CR^5$, D is $CR^6$, E is $CR^7$, G is $CR^8$, $R^6$ is —W[C(O)]$_k$Z(CR$^9$R$^{10}$)$_r$CO$_2$R$^{11}$, each of $R^4$, $R^5$, $R^7$ and $R^8$ is independently hydrogen, $C_{1-4}$ alkyl, $C_{1-4}$ alkoxy, $C_{1-4}$ alkoxycarbonyl, carboxyl, halo or hydroxyl, W is $NR^{14}$, k is 1, Z is $NR^{17}$, r is 2 and each of $R^9$, $R^{10}$, $R^{11}$, $R^{14}$ and $R^{17}$ is independently hydrogen or $C_{1-4}$ alkyl. Preferably, each of $R^4$, $R^5$, $R^7$ and $R^8$ is independently hydrogen or $C_{1-4}$ alkyl. More preferably, $R^4$, $R^5$, $R^7$ and $R^8$ are hydrogen. Preferably, $R^{11}$, $R^{14}$ and $R^{17}$ are hydrogen.

In still other embodiments of a compound of Formula (I), n is 0, Y is O, A is $CR^4$, B is $CR^5$, D is $CR^6$, E is $CR^7$, G is $CR^8$, $R^6$ is —W[C(O)]$_k$Z(CR$^9$R$^{10}$)$_r$CO$_2$R$^{11}$, each of $R^4$, $R^5$, $R^7$ and $R^8$ is independently hydrogen, $C_{1-4}$ alkyl, $C_{1-4}$ alkoxy, $C_{1-4}$ alkoxycarbonyl, carboxyl, halo or hydroxyl, W is $NR^{14}$, k is 1, Z is O, r is 1, and each of $R^9$, $R^{10}$, $R^{11}$ and $R^{14}$ is independently hydrogen or $C_{1-4}$ alkyl. Preferably, each of $R^4$, $R^5$, $R^7$ and $R^8$ is independently hydrogen or $C_{1-4}$ alkyl. More preferably, $R^4$, $R^5$, $R^7$ and $R^8$ are hydrogen. Preferably, each of $R^{11}$ and $R^{14}$ are hydrogen.

In still other embodiments of a compound of Formula (I), n is 0, Y is O, A is $CR^4$, B is $CR^5$, D is $CR^6$, E is $CR^7$, G is $CR^8$, $R^6$ is —W[C(O)]$_k$Z(CR$^9$R$^{10}$)$_r$CO$_2$R$^{11}$, each of $R^4$, $R^5$, $R^7$ and $R^8$ is independently hydrogen, $C_{1-4}$ alkyl, $C_{1-4}$ alkoxy, $C_{1-4}$ alkoxycarbonyl, carboxyl, halo or hydroxyl, W is $NR^{14}$, k is 1, Z is O, r is 2, and each of $R^9$, $R^{10}$, $R^{11}$ and $R^{14}$ is independently hydrogen or $C_{1-4}$ alkyl. Preferably, each of $R^4$, $R^5$, $R^7$ and $R^8$ is independently hydrogen or $C_{1-4}$ alkyl. More preferably, $R^4$, $R^5$, $R^7$ and $R^8$ are hydrogen. Preferably, each of $R^{11}$ and $R^{14}$ are hydrogen.

In still other embodiments of a compound of Formula (I), n is 0, Y is O, A is $CR^4$, B is $CR^5$, D is $CR^6$, E is $CR^7$, G is $CR^8$, $R^6$ is —$W[C(O)]_kZ(CR^9R^{10})_rCO_2R^{11}$, each of $R^4$, $R^5$, $R^7$ and $R^8$ is independently hydrogen, $C_{1-4}$ alkyl, $C_{1-4}$ alkoxy, $C_{1-4}$ alkoxycarbonyl, carboxyl, halo or hydroxyl, W is $NR^{14}$, k is 1, Z is $CR^{15}R^{16}$, r is 1, and each of $R^9$, $R^{10}$, $R^{11}$, $R^{14}$, $R^{15}$ and $R^{16}$ is independently hydrogen or $C_{1-4}$ alkyl. Preferably, each of $R^4$, $R^5$, $R^7$ and $R^8$ is independently hydrogen or $C_{1-4}$ alkyl. More preferably, $R^4$, $R^5$, $R^7$ and $R^8$ are hydrogen. Preferably, $R^{11}$, $R^{14}$, $R^{15}$ and $R^{16}$ are hydrogen.

In still other embodiments of a compound of Formula (I), n is 0, Y is O, A is $CR^4$, B is $CR^5$, D is $CR^6$, E is $CR^7$, G is $CR^8$, $R^6$ is —$W[C(O)]_kZ(CR^9R^{10})_rCO_2R^{11}$, each of $R^5$, $R^5$, $R^7$ and $R^8$ is independently hydrogen, $C_{1-4}$ alkyl, $C_{1-4}$ alkoxy, $C_{1-4}$ alkoxycarbonyl, carboxyl, halo or hydroxyl, W is $NR^{14}$, k is 1, Z is $CR^{15}R^{16}$, r is 2, and each of $R^9$, $R^{10}$, $R^{11}$, $R^{14}$, $R^{15}$ and $R^{16}$ is independently hydrogen or $C_{1-4}$ alkyl. Preferably, each of $R^4$, $R^5$, $R^7$ and $R^8$ is independently hydrogen or $C_{1-4}$ alkyl. More preferably, $R^4$, $R^5$, $R^7$ and $R^8$ are hydrogen. Preferably, $R^{11}$, $R^{14}$, $R^{15}$ and $R^{16}$ are hydrogen.

In still other embodiments of a compound of Formula (I), n is 1, Y is a bond, $R^{18}$ is hydrogen or methyl, A is $CR^4$, B is $CR^5$, D is $CR^6$, E is $CR^7$, G is $CR^8$, $R^4$ is —$W[C(O)]_kZ(CR^9R^{10})_rCO_2R^{11}$, each of $R^5$, $R^6$, $R^7$ and $R^8$ is independently hydrogen, $C_{1-4}$ alkyl, $C_{1-4}$ alkoxy, $C_{1-4}$ alkoxycarbonyl, carboxyl, halo or hydroxyl and each of $R^9$, $R^{10}$, $R^{11}$, $R^{12}$, $R^{13}$, $R^{14}$, $R^{15}$, $R^{16}$ and $R^{17}$ is independently hydrogen or alkyl. Preferably, each of $R^5$, $R^6$, $R^7$ and $R^8$ is independently hydrogen or $C_{1-4}$ alkyl. More preferably, $R^5$, $R^6$, $R^7$ and $R^8$ are hydrogen. Preferably, each of $R^9$, $R^{10}$, $R^{11}$, $R^{12}$, $R^{13}$, $R^{14}$, $R^{15}$, $R^{16}$ and $R^{17}$ is independently hydrogen or $C_{1-4}$ alkyl.

In still other embodiments of a compound of Formula (I), n is 1, Y is a bond, $R^{18}$ is hydrogen or methyl, A is $CR^4$, B is $CR^5$, D is $CR^6$, E is $CR^7$, G is $CR^8$, $R^4$ is —$W[C(O)]_kZ(CR^9R^{10})_rCO_2R^{11}$, each of $R^5$, $R^6$, $R^7$ and $R^8$ is independently hydrogen, $C_{1-4}$ alkyl, $C_{1-4}$ alkoxy, $C_{1-4}$ alkoxycarbonyl, carboxyl, halo or hydroxyl, W is a bond, k is 1, Z is $NR^{17}$, r is 1, and each of $R^9$, $R^{10}$, $R^{11}$ and $R^{17}$ is independently hydrogen or $C_{1-4}$ alkyl. Preferably, each of $R^5$, $R^6$, $R^7$ and $R^8$ is independently hydrogen or $C_{1-4}$ alkyl. More preferably, $R^5$, $R^6$, $R^7$ and $R^8$ are hydrogen. Preferably, $R^{11}$ and $R^{17}$ are hydrogen.

In still other embodiments of a compound of Formula (I), n is 1, Y is a bond, $R^{18}$ is hydrogen or methyl, A is $CR^4$, B is $CR^5$, D is $CR^6$, E is $CR^7$, G is $CR^8$, $R^4$ is —$W[C(O)]_kZ(CR^9R^{10})_rCO_2R^{11}$, each of $R^5$, $R^6$, $R^7$ and $R^8$ is independently hydrogen, $C_{1-4}$ alkyl, $C_{1-4}$ alkoxy, $C_{1-4}$ alkoxycarbonyl, carboxyl, halo or hydroxyl, W is a bond, k is 1, Z is $NR^{17}$, r is 2, and each of $R^9$, $R^{10}$, $R^{11}$ and $R^{17}$ is independently hydrogen or $C_{1-4}$ alkyl. Preferably, each of $R^5$, $R^6$, $R^7$ and $R^8$ is independently hydrogen or $C_{1-4}$ alkyl. More preferably, $R^5$, $R^6$, $R^7$ and $R^8$ are hydrogen. Preferably, $R^{11}$ and $R^{17}$ are hydrogen.

In still other embodiments of a compound of Formula (I), n is 1, Y is a bond, $R^{18}$ is hydrogen or methyl, A is $CR^4$, B is $CR^5$, D is $CR^6$, E is $CR^7$, C is $CR^8$, $R^4$ is —$W[C(O)]_kZ(CR^9R^{10})_rCO_2R^{11}$, each of $R^5$, $R^6$, $R^7$ and $R^8$ is independently hydrogen, $C_{1-4}$ alkyl, $C_{1-4}$ alkoxy, $C_{1-4}$ alkoxycarbonyl, carboxyl, halo or hydroxyl, W is a bond, k is 1, Z is O, r is 1, and each of $R^9$, $R^{10}$ and $R^{11}$ is independently hydrogen or $C_{1-4}$ alkyl. Preferably, each of $R^5$, $R^6$, $R^7$ and $R^8$ is independently hydrogen or $C_{1-4}$ alkyl. More preferably, $R^5$, $R^6$, $R^7$ and $R^8$ are hydrogen. Preferably, $R^{11}$ is hydrogen.

In still other embodiments of a compound of Formula (I), n is 1, Y is a bond, $R^{18}$ is hydrogen or methyl, A is $CR^4$, B is $CR^5$, D is $CR^6$, E is $CR^7$, G is $CR^8$, $R^4$ is —$W[C(O)]_kZ$ $(CR^9R^{10})_rCO_2R^{11}$, each of $R^5$, $R^6$, $R^7$ and $R^8$ is independently hydrogen, $C_{1-4}$ alkyl, $C_{1-4}$ alkoxy, $C_{1-4}$ alkoxycarbonyl, carboxyl, halo or hydroxyl, W is a bond, k is 1, Z is O, r is 2, and each of $R^9$, $R^{10}$ and $R^{11}$ is independently hydrogen or $C_{1-4}$ alkyl. Preferably, each of $R^5$, $R^6$, $R^7$ and $R^8$ is independently hydrogen or $C_{1-4}$ alkyl. More preferably, $R^5$, $R^6$, $R^7$ and $R^8$ are hydrogen. Preferably, $R^{11}$ is hydrogen.

In still other embodiments of a compound of Formula (I), n is 1, Y is a bond, $R^{18}$ is hydrogen or methyl, A is $CR^4$, B is $CR^5$, D is $CR^6$, E is $CR^7$, G is $CR^8$, $R^4$ is —$W[C(O)]_kZ$ $(CR^9R^{10})_rCO_2R^{11}$, each of $R^5$, $R^6$, $R^7$ and $R^8$ is independently hydrogen, $C_{1-4}$ alkyl, $C_{1-4}$ alkoxy, $C_{1-4}$ alkoxycarbonyl, carboxyl, halo or hydroxyl, W is O, k is 1, Z is $NR^{17}$, r is 1, and each of $R^9$, $R^{10}$, $R^{11}$ and $R^{17}$ is independently hydrogen or $C_{1-4}$ alkyl. Preferably, each of $R^5$, $R^6$, $R^7$ and $R^8$ is independently hydrogen or $C_{1-4}$ alkyl. More preferably, $R^5$, $R^6$, $R^7$ and $R^8$ are hydrogen. Preferably, $R^{11}$ and $R^{17}$ are hydrogen.

In still other embodiments of a compound of Formula (I), n is 1, Y is a bond, $R^{18}$ is hydrogen or methyl, A is $CR^4$, B is $CR^5$, D is $CR^6$, E is $CR^7$, G is $CR^8$, $R^4$ is —$W[C(O)]_kZ$ $(CR^9R^{10})_rCO_2R^{11}$, each of $R^5$, $R^6$, $R^7$ and $R^8$ is independently hydrogen, $C_{1-4}$ alkyl, $C_{1-4}$ alkoxy, $C_{1-4}$ alkoxycarbonyl, carboxyl, halo or hydroxyl, W is O, k is 1, Z is $NR^{17}$, r is 2, and each of $R^9$, $R^{10}$, $R^{11}$ and $R^{17}$ is independently hydrogen or $C_{1-4}$ alkyl. Preferably, each of $R^5$, $R^6$, $R^7$ and $R^8$ is independently hydrogen or $C_{1-4}$ alkyl. More preferably, $R^5$, $R^6$, $R^7$ and $R^8$ are hydrogen. Preferably, $R^{11}$ and $R^{17}$ are hydrogen.

In still other embodiments of a compound of Formula (I), n is 1, Y is a bond, $R^{18}$ is hydrogen or methyl, A is $CR^4$, B is $CR^5$, D is $CR^6$, E is $CR^7$, G is $CR^8$, $R^4$ is —$W[C(O)]_kZ$ $(CR^9R^{10})_rCO_2R^{11}$, each of $R^5$, $R^6$, $R^7$ and $R^8$ is independently hydrogen, $C_{1-4}$ alkyl, $C_{1-4}$ alkoxy, $C_{1-4}$ alkoxycarbonyl, carboxyl, halo or hydroxyl, W is O, k is 1, Z is O, r is 1, and each of $R^9$, $R^{10}$ and $R^{11}$ is independently hydrogen or $C_{1-4}$ alkyl. Preferably, each of $R^5$, $R^6$, $R^7$ and $R^8$ is independently hydrogen or $C_{1-4}$ alkyl. More preferably, $R^5$, $R^6$, $R^7$ and $R^8$ are hydrogen. Preferably, $R^{11}$ is hydrogen.

In still other embodiments of a compound of Formula (I), n is 1, Y is a bond, $R^{18}$ is hydrogen or methyl, A is $CR^4$, B is $CR^5$, D is $CR^6$, E is $CR^7$, G is $CR^8$, $R^4$ is —$W[C(O)]_kZ$ $(CR^9R^{10})_rCO_2R^{11}$, each of $R^5$, $R^6$, $R^7$ and $R^8$ is independently hydrogen, $C_{1-4}$ alkyl, $C_{1-4}$ alkoxy, $C_{1-4}$ alkoxycarbonyl, carboxyl, halo or hydroxyl, W is O, k is 1, Z is O, r is 2, and each of $R^9$, $R^{10}$ and $R^{11}$ is independently hydrogen or $C_{1-4}$ alkyl. Preferably, each of $R^5$, $R^6$, $R^7$ and $R^8$ is independently hydrogen or $C_{1-4}$ alkyl. More preferably, $R^5$, $R^6$, $R^7$ and $R^8$ are hydrogen. Preferably, $R^{11}$ is hydrogen.

In still other embodiments of a compound of Formula (I), n is 1, Y is a bond, $R^{18}$ is hydrogen or methyl, A is $CR^4$, B is $CR^5$, D is $CR^6$, E is $CR^7$, G is $CR^8$, $R^4$ is —$W[C(O)]_kZ$ $(CR^9R^{10})_rCO_2R^{11}$, each of $R^5$, $R^6$, $R^7$ and $R^8$ is independently hydrogen, $C_{1-4}$ alkyl, $C_{1-4}$ alkoxy, $C_{1-4}$ alkoxycarbonyl, carboxyl, halo or hydroxyl, W is O, k is 1, Z is $CR^{15}R^{16}$, r is 1, and each of $R^9$, $R^{10}$, $R^{11}$, $R^{15}$ and $R^{16}$ is independently hydrogen or $C_{1-4}$ alkyl. Preferably, each of $R^5$, $R^6$, $R^7$ and $R^8$ is independently hydrogen or $C_{1-4}$ alkyl. More preferably, $R^5$, $R^6$, $R^7$ and $R^8$ are hydrogen. Preferably, $R^{11}$, $R^{15}$ and $R^{16}$ are hydrogen.

In still other embodiments of a compound of Formula (I), n is 1, Y is a bond, $R^{18}$ is hydrogen or methyl, A is $CR^4$, B is $CR^5$, D is $CR^6$, E is $CR^7$, G is $CR^8$, $R^4$ is —$W[C(O)]_kZ$ $(CR^9R^{10})_rCO_2R^{11}$, each of $R^5$, $R^6$, $R^7$ and $R^8$ is independently hydrogen, $C_{1-4}$ alkyl, $C_{1-4}$ alkoxy, $C_{1-4}$ alkoxycarbonyl, carboxyl, halo or hydroxyl, W is O, k is 1, Z is $CR^{15}R^{16}$, r is 2, and each of $R^9$, $R^{10}$, $R^{11}$, $R^{15}$ and $R^{16}$ is independently hydrogen or $C_{1-4}$ alkyl. Preferably, each of $R^5$, $R^6$, $R^7$ and $R^8$ is independently hydrogen or $C_{1-4}$ alkyl. More preferably, $R^5$, $R^6$, $R^7$ and $R^8$ are hydrogen. Preferably, $R^{11}$, $R^{15}$ and $R^{16}$ are hydrogen.

In still other embodiments of a compound of Formula (I), n is 1, Y is a bond, $R^{18}$ is hydrogen or methyl, A is $CR^4$, B is $CR^5$, D is $CR^6$, E is $CR^7$, G is $CR^8$, $R^4$ is —W[C(O)]$_k$Z(CR$^9$R$^{10}$)$_r$CO$_2$R$^{11}$, each of $R^5$, $R^6$, $R^7$ and $R^8$ is independently hydrogen, $C_{1-4}$ alkyl, $C_{1-4}$ alkoxy, $C_{1-4}$ alkoxycarbonyl, carboxyl, halo or hydroxyl, W is NR$^{14}$, k is 1, Z is NR$^{17}$, r is 1 and each of $R^9$, $R^{10}$, $R^{11}$, $R^{14}$ and $R^{17}$ is independently hydrogen or $C_{1-4}$ alkyl. Preferably, each of $R^5$, $R^6$, $R^7$ and $R^8$ is independently hydrogen or $C_{1-4}$ alkyl. More preferably, $R^5$, $R^6$, $R^7$ and $R^8$ are hydrogen. Preferably, $R^{11}$, $R^{14}$ and $R^{17}$ are hydrogen.

In still other embodiments of a compound of Formula (I), n is 1, Y is a bond, $R^{18}$ is hydrogen or methyl, A is $CR^4$, B is $CR^5$, D is $CR^6$, E is $CR^7$, G is $CR^8$, $R^4$ is —W[C(O)]$_k$Z(CR$^9$R$^{10}$)$_r$CO$_2$R$^{11}$, each of $R^5$, $R^6$, $R^7$ and $R^8$ is independently hydrogen, $C_{1-4}$ alkyl, $C_{1-4}$ alkoxy, $C_{1-4}$ alkoxycarbonyl, carboxyl, halo or hydroxyl, W is NR$^{14}$, k is 1, Z is NR$^{17}$, r is 2 and each of $R^9$, $R^{10}$, $R^{11}$, $R^{14}$ and $R^{17}$ is independently hydrogen or $C_{1-4}$ alkyl. Preferably, each of $R^5$, $R^6$, $R^7$ and $R^8$ is independently hydrogen or $C_{1-4}$ alkyl. More preferably, $R^5$, $R^6$, $R^7$ and $R^8$ are hydrogen. Preferably, $R^{11}$, $R^{14}$ and $R^{17}$ are hydrogen.

In still other embodiments of a compound of Formula (I), n is 1, Y is a bond, $R^{18}$ is hydrogen or methyl, A is $CR^4$, B is $CR^5$, D is $CR^6$, E is $CR^7$, G is $CR^8$, $R^4$ is —W[C(O)]$_k$Z(CR$^9$R$^{10}$)$_r$CO$_2$R$^{11}$, each of $R^5$, $R^6$, $R^7$ and $R^8$ is independently hydrogen, $C_{1-4}$ alkyl, $C_{1-4}$ alkoxy, $C_{1-4}$ alkoxycarbonyl, carboxyl, halo or hydroxyl, W is NR$^{14}$, k is 1, Z is O, r is 1, and each of $R^9$, $R^{10}$, $R^{11}$ and $R^{14}$ is independently hydrogen or $C_{1-4}$ alkyl. Preferably, each of $R^5$, $R^6$, $R^7$ and $R^8$ is independently hydrogen or $C_{1-4}$ alkyl. More preferably, $R^5$, $R^6$, $R^7$ and $R^8$ are hydrogen. Preferably, each of $R^{11}$ and $R^{14}$ are hydrogen.

In still other embodiments of a compound of Formula (I), n is 1, Y is a bond, $R^{18}$ is hydrogen or methyl, A is $CR^4$, B is $CR^5$, D is $CR^6$, E is $CR^7$, G is $CR^8$, $R^4$ is —W[C(O)]$_k$Z(CR$^9$R$^{10}$)$_r$CO$_2$R$^{11}$, each of $R^5$, $R^6$, $R^7$ and $R^8$ is independently hydrogen, $C_{1-4}$ alkyl, $C_{1-4}$ alkoxy, $C_{1-4}$ alkoxycarbonyl, carboxyl, halo or hydroxyl, W is NR$^{14}$, k is 1, Z is O, r is 2, and each of $R^9$, $R^{10}$, $R^{11}$ and $R^{14}$ is independently hydrogen or $C_{1-4}$ alkyl. Preferably, each of $R^5$, $R^6$, $R^7$ and $R^8$ is independently hydrogen or $C_{1-4}$ alkyl. More preferably, $R^5$, $R^6$, $R^7$ and $R^8$ are hydrogen. Preferably, each of $R^{11}$ and $R^{14}$ are hydrogen.

In still other embodiments of a compound of Formula (I), n is 1, Y is a bond, $R^{18}$ is hydrogen or methyl, A is $CR^4$, B is $CR^5$, D is $CR^6$, E is $CR^7$, G is $CR^8$, $R^4$ is —W[C(O)]$_k$Z(CR$^9$R$^{10}$)$_r$CO$_2$R$^{11}$, each of $R^5$, $R^6$, $R^7$ and $R^8$ is independently hydrogen, $C_{1-4}$ alkyl, $C_{1-4}$ alkoxy, $C_{1-4}$ alkoxycarbonyl, carboxyl, halo or hydroxyl, W is NR$^{14}$, k is 1, Z is CR$^{15}$R$^{16}$, r is 1, and each of $R^9$, $R^{10}$, $R^{11}$, $R^{14}$, $R^{15}$ and $R^{16}$ is independently hydrogen or $C_{1-4}$ alkyl. Preferably, each of $R^5$, $R^6$, $R^7$ and $R^8$ is independently hydrogen or $C_{1-4}$ alkyl. More preferably, $R^5$, $R^6$, $R^7$ and $R^8$ are hydrogen. Preferably, $R^{11}$, $R^{14}$, $R^{15}$ and $R^{16}$ are hydrogen.

In still other embodiments of a compound of Formula (I), n is 1, Y is a bond, $R^{18}$ is hydrogen or methyl, A is $CR^4$, B is $CR^5$, D is $CR^6$, E is $CR^7$, G is $CR^8$, $R^4$ is —W[C(O)]$_k$Z(CR$^9$R$^{10}$)$_r$CO$_2$R$^{11}$, each of $R^5$, $R^6$, $R^7$ and $R^8$ is independently hydrogen, $C_{1-4}$ alkyl, $C_{1-4}$ alkoxy, $C_{1-4}$ alkoxycarbonyl, carboxyl, halo or hydroxyl, W is NR$^{14}$, k is 1, Z is CR$^{15}$R$^{16}$, r is 2, and each of $R^9$, $R^{10}$, $R^{11}$, $R^{14}$, $R^{15}$ and $R^{16}$ is independently hydrogen or $C_{1-4}$ alkyl. Preferably, each of $R^5$, $R^6$, $R^7$ and $R^8$ is independently hydrogen or $C_{1-4}$ alkyl. More preferably, $R^5$, $R^6$, $R^7$ and $R^8$ are hydrogen. Preferably, $R^{11}$, $R^{14}$, $R^{15}$ and $R^{16}$ are hydrogen.

In still other embodiments of a compound of Formula (I), n is 1, Y is a bond, $R^{18}$ is selected from the group consisting of hydrogen, alkyl, substituted alkyl, aryl, substituted aryl, arylalkyl, cycloalkyl, and heteroaryl, A is $CR^4$, B is N, D is $CR^6$, E is $CR^7$, G is $CR^8$, $R^4$ is —W[C(O)]$_k$Z(CR$^9$R$^{10}$)$_r$CO$_2$R$^{11}$, each of $R^6$, $R^7$ and $R^8$ is independently hydrogen, $C_{1-4}$ alkyl, $C_{1-4}$ alkoxy, $C_{1-4}$ alkoxycarbonyl, carboxyl, halo or hydroxyl and each of $R^9$, $R^{10}$, $R^{11}$, $R^{12}$, $R^{13}$, $R^{14}$, $R^{15}$, $R^{16}$ and $R^{17}$ is independently hydrogen or alkyl. Preferably, $R^{18}$ is selected from the group consisting of hydrogen, $C_{1-4}$ alkyl, phenyl, substituted phenyl, benzyl and substituted benzyl. More preferably, $R^{18}$ is hydrogen or methyl. Preferably, each of $R^6$, $R^7$ and $R^8$ is independently hydrogen or $C_{1-4}$ alkyl. More preferably, $R^6$, $R^7$ and $R^8$ are hydrogen. Preferably, each of $R^9$, $R^{10}$, $R^{11}$, $R^{12}$, $R^{13}$, $R^{14}$, $R^{15}$, $R^{16}$ and $R^{17}$ is independently hydrogen or $C_{1-4}$ alkyl.

In still other embodiments of a compound of Formula (I), n is 1, Y is a bond, $R^{18}$ is selected from the group consisting of hydrogen, alkyl, substituted alkyl, aryl, substituted aryl, arylalkyl, cycloalkyl, and heteroaryl, A is $CR^4$, B is $CR^5$, D is N, E is $CR^7$, G is $CR^8$, $R^4$ is —W[C(O)]$_k$Z(CR$^9$R$^{10}$)$_r$CO$_2$R$^{11}$, each of $R^5$, $R^7$ and $R^8$ is independently hydrogen, $C_{1-4}$ alkyl, $C_{1-4}$ alkoxy, $C_{1-4}$ alkoxycarbonyl, carboxyl, halo or hydroxyl and each of $R^9$, $R^{10}$, $R^{11}$, $R^{12}$, $R^{13}$, $R^{14}$, $R^{15}$, $R^{16}$ and $R^{17}$ is independently hydrogen or alkyl. Preferably, $R^{18}$ is selected from the group consisting of hydrogen, $C_{1-4}$ alkyl, phenyl, substituted phenyl, benzyl and substituted benzyl. More preferably, $R^{18}$ is hydrogen or methyl. Preferably, each of $R^5$, $R^7$ and $R^8$ is independently hydrogen or $C_{1-4}$ alkyl. More preferably, $R^5$, $R^7$ and $R^8$ are hydrogen. Preferably, each of $R^9$, $R^{10}$, $R^{11}$, $R^{12}$, $R^{13}$, $R^{14}$, $R^{15}$, $R^{16}$ and $R^{17}$ is independently hydrogen or $C_{1-4}$ alkyl.

In still other embodiments of a compound of Formula (I), n is 1, Y is a bond, $R^{18}$ is selected from the group consisting of hydrogen, alkyl, substituted alkyl, aryl, substituted aryl, arylalkyl, cycloalkyl, and heteroaryl, A is $CR^4$, B is $CR^5$, D is $CR^6$, E is N, G is $CR^8$, $R^4$ is —W[C(O)]$_k$Z(CR$^9$R$^{10}$)$_r$CO$_2$R$^{11}$, each of $R^5$, $R^6$ and $R^8$ is independently hydrogen, $C_{1-4}$ alkyl, $C_{1-4}$ alkoxy, $C_{1-4}$ alkoxycarbonyl, carboxyl, halo or hydroxyl and each of $R^9$, $R^{10}$, $R^{11}$, $R^{12}$, $R^{13}$, $R^{14}$, $R^{15}$, $R^{16}$ and $R^{17}$ is independently hydrogen or alkyl. Preferably, $R^{18}$ is selected from the group consisting of hydrogen, $C_{1-4}$ alkyl, phenyl, substituted phenyl, benzyl and substituted benzyl. More preferably, $R^{18}$ is hydrogen or methyl. Preferably, each of $R^5$, $R^6$ and $R^8$ is independently hydrogen or $C_{1-4}$ alkyl. More preferably, $R^5$, $R^6$ and $R^8$ are hydrogen. Preferably, each of $R^9$, $R^{10}$, $R^{11}$, $R^{12}$, $R^{13}$, $R^{14}$, $R^{15}$, $R^{16}$ and $R^{17}$ is independently hydrogen or $C_{1-4}$ alkyl.

In still other embodiments of a compound of Formula (I), n is 1, Y is a bond, $R^{18}$ is selected from the group consisting of hydrogen, alkyl, substituted alkyl, aryl, substituted aryl, arylalkyl, cycloalkyl, and heteroaryl, A is $CR^4$, B is $CR^5$, D is $CR^6$, E is $CR^7$, G is N, $R^4$ is —W[C(O)]$_k$Z(CR$^9$R$^{10}$)$_r$CO$_2$R$^{11}$, each of $R^5$, $R^6$ and $R^7$ is independently hydrogen, $C_{1-4}$ alkyl, $C_{1-4}$ alkoxy, $C_{1-4}$ alkoxycarbonyl, carboxyl, halo or hydroxyl and each of $R^9$, $R^{10}$, $R^{11}$, $R^{12}$, $R^{13}$, $R^{14}$, $R^{15}$, $R^{16}$ and $R^{17}$ is independently hydrogen or alkyl. Preferably, $R^{18}$ is selected from the group consisting of hydrogen, $C_{1-4}$ alkyl, phenyl, substituted phenyl, benzyl and substituted benzyl. More preferably, $R^{18}$ is hydrogen or methyl. Preferably, each of $R^5$, $R^6$ and $R^7$ is independently hydrogen or $C_{1-4}$ alkyl. More preferably, $R^5$, $R^6$ and $R^7$ are hydrogen. Preferably, each of $R^9$, $R^{10}$, $R^{11}$, $R^{12}$, $R^{13}$, $R^{14}$, $R^{15}$, $R^{16}$ and $R^{17}$ is independently hydrogen or $C_{1-4}$ alkyl.

In still other embodiments of a compound of Formula (I), n is 1, Y is a bond, $R^{18}$ is selected from the group consisting of hydrogen, alkyl, substituted alkyl, aryl, substituted aryl, arylalkyl, cycloalkyl, and heteroaryl, A is $CR^4$, B is N, D is $CR^6$, E is $CR^7$, G is N, $R^4$ is $—W[C(O)]_kZ(CR^9R^{10})_rCO_2R^{11}$, each of $R^4$ and $R^6$ is independently hydrogen, $C_{1-4}$ alkyl, $C_{1-4}$ alkoxy, $C_{1-4}$ alkoxycarbonyl, carboxyl, halo or hydroxyl and each of $R^9$, $R^{10}$, $R^{11}$, $R^{12}$, $R^{13}$, $R^{14}$, $R^{15}$, $R^{16}$ and $R^{17}$ is independently hydrogen or alkyl. Preferably, $R^{18}$ is selected from the group consisting of hydrogen, $C_{1-4}$ alkyl, phenyl, substituted phenyl, benzyl and substituted benzyl. More preferably, $R^{18}$ is hydrogen or methyl. Preferably, each of $R^4$ and $R^6$ is independently hydrogen or $C_{1-4}$ alkyl. More preferably, $R^4$ and $R^6$ are hydrogen. Preferably, each of $R^9$, $R^{10}$, $R^{11}$, $R^{12}$, $R^{13}$, $R^{14}R^{15}$, $R^{16}$ and $R^{17}$ is independently hydrogen or $C_{1-4}$ alkyl.

In still other embodiments of a compound of Formula (I), n is 1, Y is a bond, $R^{18}$ is selected from the group consisting of hydrogen, alkyl, substituted alkyl, aryl, substituted aryl, arylalkyl, cycloalkyl and heteroaryl, A is $CR^4$, B is $CR^5$, D is $CR^6$, E is $CR^7$, G is $CR^8$, $R^5$ is $—W[C(O)]_kZ(CR^9R^{10})_rCO_2R^{11}$, each of $R^4$, $R^6$, $R^7$ and $R^8$ is independently hydrogen, $C_{1-4}$ alkyl, $C_{1-4}$ alkoxy, $C_{1-4}$ alkoxycarbonyl, carboxyl, halo or hydroxyl and each of $R^9$, $R^{10}$, $R^{11}$, $R^{12}$, $R^{13}$, $R^{14}$, $R^{15}$, $R^{16}$ and $R^{17}$ is independently hydrogen or alkyl. Preferably, each of $R^4$, $R^6$, $R^7$ and $R^8$ is independently hydrogen or $C_{1-4}$ alkyl. More preferably, $R^4$, $R^6$, $R^7$ and $R^8$ are hydrogen. Preferably, each of $R^9$, $R^{10}$, $R^{11}$, $R^{12}$, $R^{13}$, $R^{14}$, $R^{15}$, $R^{16}$ and $R^{17}$ is independently hydrogen or $C_{1-4}$ alkyl.

In still other embodiments of a compound of Formula (I), n is 1, Y is a bond, $R^{18}$ is hydrogen or methyl, A is $CR^4$, B is $CR^5$, D is $CR^6$, E is $CR^7$, G is $CR^8$, $R^5$ is $—W[C(O)]_kZ(CR^9R^{10})_rCO_2R^{11}$, each of $R^4$, $R^6$, $R^7$ and $R^8$ is independently hydrogen, $C_{1-4}$ alkyl, $C_{1-4}$ alkoxy, $C_{1-4}$ alkoxycarbonyl, carboxyl, halo or hydroxyl, W is a bond, k is 1, Z is $NR^{17}$, r is 1, and each of $R^9$, $R^{10}$, $R^{11}$ and $R^{17}$ is independently hydrogen or $C_{1-4}$ alkyl. Preferably, each of $R^4$, $R^6$, $R^7$ and $R^8$ is independently hydrogen or $C_{1-4}$ alkyl. More preferably, $R^4$, $R^6$, $R^7$ and $R^8$ are hydrogen. Preferably, $R^{11}$ and $R^{17}$ are hydrogen.

In still other embodiments of a compound of Formula (I), n is 1, Y is a bond, $R^{18}$ is hydrogen or methyl, A is $CR^4$, B is $CR^5$, D is $CR^6$, E is $CR^7$, G is $CR^8$, $R^5$ is $—W[C(O)]_kZ(CR^9R^{10})_rCO_2R^{11}$, each of $R^4$, $R^6$, $R^7$ and $R^8$ is independently hydrogen, $C_{1-4}$ alkyl, $C_{1-4}$ alkoxy, $C_{1-4}$ alkoxycarbonyl, carboxyl, halo or hydroxyl, W is a bond, k is 1, Z is $NR^{17}$, r is 2, and each of $R^9$, $R^{10}$, $R^{11}$ and $R^{17}$ is independently hydrogen or $C_{1-4}$ alkyl. Preferably, each of $R^4$, $R^6$, $R^7$ and $R^8$ is independently hydrogen or $C_{1-4}$ alkyl. More preferably, $R^4$, $R^6$, $R^7$ and $R^8$ are hydrogen. Preferably, $R^{11}$ and $R^{17}$ are hydrogen.

In still other embodiments of a compound of Formula (I), n is 1, Y is a bond, $R^{18}$ is hydrogen or methyl, A is $CR^4$, B is $CR^5$, D is $CR^6$, E is $CR^7$, G is $CR^8$, $R^5$ is $—W[C(O)]_kZ(CR^9R^{10})_rCO_2R^{11}$, each of $R^4$, $R^6$, $R^7$ and $R^8$ is independently hydrogen, $C_{1-4}$ alkyl, $C_{1-4}$ alkoxy, $C_{1-4}$ alkoxycarbonyl, carboxyl, halo or hydroxyl, W is a bond, k is 1, Z is O, r is 1, and each of $R^9$, $R^{10}$ and $R^{11}$ is independently hydrogen or $C_{1-4}$ alkyl. Preferably, each of $R^4$, $R^6$, $R^7$ and $R^8$ is independently hydrogen or $C_{1-4}$ alkyl. More preferably, each of $R^5$, $R^6$, $R^7$ and $R^8$ is hydrogen. Preferably, $R^{11}$ is hydrogen.

In still other embodiments of a compound of Formula (I), n is 1, Y is a bond, $R^{18}$ is hydrogen or methyl, A is $CR^4$, B is $CR^5$, D is $CR^6$, E is $CR^7$, G is $CR^8$, $R^5$ is $—W[C(O)]_kZ(CR^9R^{10})_rCO_2R^{11}$, each of $R^4$, $R^6$, $R^7$ and $R^8$ is independently hydrogen, $C_{1-4}$ alkyl, $C_{1-4}$ alkoxy, $C_{1-4}$ alkoxycarbonyl, carboxyl, halo or hydroxyl, W is a bond, k is 1, Z is O, r is 2, and each of $R^9$, $R^{10}$ and $R^{11}$ is independently hydrogen or $C_{1-4}$ alkyl. Preferably, each of $R^4$, $R^6$, $R^7$ and $R^8$ is independently hydrogen or $C_{1-4}$ alkyl. More preferably, $R^4$, $R^6$, $R^7$ and $R^8$ are hydrogen. Preferably, $R^{11}$ is hydrogen.

In still other embodiments of a compound of Formula (I), n is 1, Y is a bond, $R^{18}$ is hydrogen or methyl, A is $CR^4$, B is $CR^5$, D is $CR^6$, E is $CR^7$, G is $CR^8$, $R^5$ is $—W[C(O)]_kZ(CR^9R^{10})_rCO_2R^{11}$, each of $R^4$, $R^6$, $R^7$ and $R^8$ is independently hydrogen, $C_{1-4}$ alkyl, $C_{1-4}$ alkoxy, $C_{1-4}$ alkoxycarbonyl, carboxyl, halo or hydroxyl, W is O, k is 1, Z is $NR^{17}$, r is 1, and each of $R^9$, $R^{10}$, $R^{11}$ and $R^{17}$ is independently hydrogen or $C_{1-4}$ alkyl. Preferably, each of $R^4$, $R^6$, $R^7$ and $R^8$ is independently hydrogen or $C_{1-4}$ alkyl. More preferably, $R^5$, $R^6$, $R^7$ and $R^8$ are hydrogen. Preferably, $R^{11}$ and $R^{17}$ are hydrogen.

In still other embodiments of a compound of Formula (I), n is 1, Y is a bond, $R^{18}$ is hydrogen or methyl, A is $CR^4$, B is $CR^5$, D is $CR^6$, E is $CR^7$, G is $CR^8$, $R^5$ is $—W[C(O)]_kZ(CR^9R^{10})_rCO_2R^{11}$, each of $R^4$, $R^6$, $R^7$ and $R^8$ is independently hydrogen, $C_{1-4}$ alkyl, $C_{1-4}$ alkoxy, $C_{1-4}$ alkoxycarbonyl, carboxyl, halo or hydroxyl, W is O, k is 1, Z is $NR^{17}$, r is 2, and each of $R^9$, $R^{10}$, $R^1$ and $R^{17}$ is independently hydrogen or $C_{1-4}$ alkyl. Preferably, each of $R^4$, $R^6$, $R^7$ and $R^8$ is independently hydrogen or $C_{1-4}$ alkyl. More preferably, $R^4$, $R^6$, $R^7$ and $R^8$ are hydrogen. Preferably, $R^{11}$ and $R^{17}$ are hydrogen.

In still other embodiments of a compound of Formula (I), n is 1, Y is a bond, $R^{18}$ is hydrogen or methyl, A is $CR^4$, B is $CR^5$, D is $CR^6$, E is $CR^7$, G is $CR^8$, $R^5$ is $—W[C(O)]_kZ(CR^9R^{10})_rCO_2R^{11}$, each of $R^4$, $R^6$, $R^7$ and $R^8$ is independently hydrogen, $C_{1-4}$ alkyl, $C_{1-4}$ alkoxy, $C_{1-4}$ alkoxycarbonyl, carboxyl, halo or hydroxyl, W is O, k is 1, Z is O, r is 1, and each of $R^9$, $R^{10}$ and $R^{11}$ is independently hydrogen or $C_{1-4}$ alkyl. Preferably, each of $R^4$, $R^6$, $R^7$ and $R^8$ is independently hydrogen or $C_{1-4}$ alkyl. More preferably, each of $R^4$, $R^6$, $R^7$ and $R^8$ is hydrogen. Preferably, $R^{11}$ is hydrogen.

In still other embodiments of a compound of Formula (I), n is 1, Y is a bond, $R^{18}$ is hydrogen or methyl, A is $CR^4$, B is $CR^5$, D is $CR^6$, E is $CR^7$, G is $CR^8$, $R^5$ is $—W[C(O)]_kZ(CR^9R^{10})_rCO_2R^{11}$, each of $R^4$, $R^6$, $R^7$ and $R^8$ is independently hydrogen, $C_{1-4}$ alkyl, $C_{1-4}$ alkoxy, $C_{1-4}$ alkoxycarbonyl, carboxyl, halo or hydroxyl, W is O, k is I, Z is O, r is 2, and each of $R^9$, $R^{10}$ and $R^{11}$ is independently hydrogen or $C_{1-4}$ alkyl. Preferably, each of $R^4$, $R^6$, $R^7$ and $R^8$ is independently hydrogen or $C_{1-4}$ alkyl. More preferably, each of $R^4$, $R^6$, $R^7$ and $R^8$ is hydrogen. Preferably, $R^{11}$ is hydrogen.

In still other embodiments of a compound of Formula (I), n is 1, Y is a bond, $R^{18}$ is hydrogen or methyl, A is $CR^4$, B is $CR^5$, D is $CR^6$, E is $CR^7$, G is $CR^8$, $R^5$ is $—W[C(O)]_kZ(CR^9R^{10})_rCO_2R^{11}$, each of $R^4$, $R^6$, $R^7$ and $R^8$ is independently hydrogen, $C_{1-4}$ alkyl, $C_{1-4}$ alkoxy, $C_{1-4}$ alkoxycarbonyl, carboxyl, halo or hydroxyl, W is O, k is 1, Z is $CR^{15}R^{16}$, r is 1, and each of $R^9$, $R^{10}$, $R^{11}$, $R^{15}$ and $R^{16}$ is independently hydrogen or $C_{1-4}$ alkyl. Preferably, each of $R^4$, $R^6$, $R^7$ and $R^8$ is independently hydrogen or $C_{1-4}$ alkyl. More preferably, $R^4$, $R^6$, $R^7$ and $R^8$ are hydrogen. Preferably, $R^{11}$, $R^{15}$ and $R^{16}$ are hydrogen.

In still other embodiments of a compound of Formula (I), n is 1, Y is a bond, $R^{18}$ is hydrogen or methyl, A is $CR^4$, B is $CR^5$, D is $CR^6$, E is $CR^7$, G is $CR^8$, $R^5$ is $—W[C(O)]_kZ(CR^9R^{10})_rCO_2R^{11}$, each of $R^4$, $R^6$, $R^7$ and $R^8$ is independently hydrogen, $C_{1-4}$ alkyl, $C_{1-4}$ alkoxy, $C_{1-4}$ alkoxycarbonyl, carboxyl, halo or hydroxyl, W is O, k is 1, Z is $CR^{15}R^{16}$, r is 2, and each of $R^9$, $R^{10}$, $R^{11}$, $R^{15}$ and $R^{16}$ is independently hydrogen or $C_{1-4}$ alkyl. Preferably, each of $R^4$, $R^6$, $R^7$ and $R^8$ is independently hydrogen or $C_{1-4}$ alkyl. More preferably, $R^4$, $R^6$, $R^7$ and $R^8$ are hydrogen. Preferably, $R^{11}$, $R^{15}$ and $R^{16}$ are hydrogen.

In still other embodiments of a compound of Formula (I), n is 1, Y is a bond, $R^{18}$ is hydrogen or methyl, A is $CR^4$, B is $CR^5$, D is $CR^6$, E is $CR^7$, G is $CR^8$, $R^5$ is —$W[C(O)]_kZ(CR^9R^{10})_rCO_2R^{11}$, each of $R^4$, $R^6$, $R^7$ and $R^8$ is independently hydrogen, $C_{1-4}$ alkyl, $C_{1-4}$ alkoxy, $C_{1-4}$ alkoxycarbonyl, carboxyl, halo or hydroxyl, W is $NR^{14}$, k is 1, Z is $NR^{17}$, r is 1 and each of $R^9$, $R^{10}$, $R^{11}$, $R^{14}$ and $R^{17}$ is independently hydrogen or $C_{1-4}$ alkyl. Preferably, each of $R^4$, $R^6$, $R^7$ and $R^8$ is independently hydrogen or $C_{1-4}$ alkyl. More preferably, $R^4$, $R^6$, $R^7$ and $R^8$ are hydrogen. Preferably, $R^{11}$, $R^{14}$ and $R^{17}$ are hydrogen.

In still other embodiments of a compound of Formula (I), n is 1, Y is a bond, $R^{18}$ is hydrogen or methyl, A is $CR^4$, B is $CR^5$, D is $CR^6$, E is $CR^7$, G is $CR^8$, $R^5$ is —$W[C(O)]_kZ(CR^9R^{10})_rCO_2R^{11}$, each of $R^4$, $R^6$, $R^7$ and $R^8$ is independently hydrogen, $C_{1-4}$ alkyl, $C_{1-4}$ alkoxy, $C_{1-4}$ alkoxycarbonyl, carboxyl, halo or hydroxyl, W is $NR^{14}$, k is 1, Z is $NR^{17}$, r is 2 and each of $R^9$, $R^{10}$, $R^{11}$, $R^{14}$ and $R^{17}$ is independently hydrogen or $C_{1-4}$ alkyl. Preferably, each of $R^4$, $R^6$, $R^7$ and $R^8$ is independently hydrogen or $C_{1-4}$ alkyl. More preferably, $R^4$, $R^6$, $R^7$ and $R^8$ are hydrogen. Preferably, $R^{11}$, $R^{14}$ and $R^{17}$ are hydrogen.

In still other embodiments of a compound of Formula (I), n is 1, Y is a bond, $R^{18}$ is hydrogen or methyl, A is $CR^4$, B is $CR^5$, D is $CR^6$, E is $CR^7$, G is $CR^8$, $R^5$ is —$W[C(O)]_kZ(CR^9R^{10})_rCO_2R^{11}$, each of $R^4$, $R^6$, $R^7$ and $R^8$ is independently hydrogen, $C_{1-4}$ alkyl, $C_{1-4}$ alkoxy, $C_{1-4}$ alkoxycarbonyl, carboxyl, halo or hydroxyl, W is $NR^{14}$, k is 1, Z is O, r is 1, and each of $R^9$, $R^{10}$, $R^{11}$ and $R^{14}$ is independently hydrogen or $C_{1-4}$ alkyl. Preferably, each of $R^4$, $R^6$, $R^7$ and $R^8$ is independently hydrogen or $C_{1-4}$ alkyl. More preferably, $R^4$, $R^6$, $R^7$ and $R^8$ are hydrogen. Preferably, each of $R^{11}$ and $R^{14}$ are hydrogen.

In still other embodiments of a compound of Formula (I), n is 1, Y is a bond, $R^{18}$ is hydrogen or methyl, A is $CR^4$, B is $CR^5$, D is $CR^6$, E is $CR^7$, G is $CR^8$, $R^5$ is —$W[C(O)]_kZ(CR^9R^{10})_rCO_2R^{11}$, each of $R^4$, $R^6$, $R^7$ and $R^8$ is independently hydrogen, $C_{1-4}$ alkyl, $C_{1-4}$ alkoxy, $C_{1-4}$ alkoxycarbonyl, carboxyl, halo or hydroxyl, W is $NR^{14}$, k is 1, Z is O, r is 2, and each of $R^9$, $R^{10}$, $R^{11}$ and $R^{14}$ is independently hydrogen or $C_{1-4}$ alkyl. Preferably, each of $R^4$, $R^6$, $R^7$ and $R^8$ is independently hydrogen or $C_{1-4}$ alkyl. More preferably, $R^4$, $R^6$, $R^7$ and $R^8$ are hydrogen. Preferably, each of $R^{11}$ and $R^{14}$ are hydrogen.

In still other embodiments of a compound of Formula (I), n is 1, Y is a bond, $R^{18}$ is hydrogen or methyl, A is $CR^4$, B is $CR^5$, D is $CR^6$, E is $CR^7$, G is $CR^8$, $R^5$ is —$W[C(O)]_kZ(CR^9R^{10})_rCO_2R^{11}$, each of $R^4$, $R^6$, $R^7$ and $R^8$ is independently hydrogen, $C_{1-4}$ alkyl, $C_{1-4}$ alkoxy, $C_{1-4}$ alkoxycarbonyl, carboxyl, halo or hydroxyl, W is $NR^{14}$, k is 1, Z is $CR^{15}R^{16}$, r is 1, and each of $R^9$, $R^{10}$, $R^{11}$, $R^{14}$, $R^{15}$ and $R^{16}$ is independently hydrogen or $C_{1-4}$ alkyl. Preferably, each of $R^4$, $R^6$, $R^7$ and $R^8$ is independently hydrogen or $C_{1-4}$ alkyl. More preferably, $R^4$, $R^6$, $R^7$ and $R^8$ are hydrogen. Preferably, $R^{11}$, $R^{14}$, $R^{15}$ and $R^{16}$ are hydrogen.

In still other embodiments of a compound of Formula (I), n is 1, Y is a bond, $R^{18}$ is hydrogen or methyl, A is $CR^4$, B is $CR^5$, D is $CR^6$, E is $CR^7$, G is $CR^8$, $R^5$ is —$W[C(O)]_kZ(CR^9R^{10})_rCO_2R^{11}$, each of $R^4$, $R^6$, $R^7$ and $R^8$ is independently hydrogen, $C_{1-4}$ alkyl, $C_{1-4}$ alkoxy, $C_{1-4}$ alkoxycarbonyl, carboxyl, halo or hydroxyl, W is $NR^{14}$, k is 1, Z is $CR^{15}R^{16}$, r is 2, and each of $R^9$, $R^{10}$, $R^{11}$, $R^{14}$, $R^{15}$ and $R^{16}$ is independently hydrogen or $C_{1-4}$ alkyl. Preferably, each of $R^4$, $R^6$, $R^7$ and $R^8$ is independently hydrogen or $C_{1-4}$ alkyl. More preferably, $R^4$, $R^6$, $R^7$ and $R^8$ are hydrogen. Preferably, $R^{11}$, $R^{14}$, $R^{15}$ and $R^{16}$ are hydrogen.

In still other embodiments of a compound of Formula (I), n is 1, Y is a bond, $R^{18}$ is selected from the group consisting of hydrogen, alkyl, substituted alkyl, aryl, substituted aryl, arylalkyl, cycloalkyl, and heteroaryl, A is N, B is $CR^5$, D is $CR^6$, E is $CR^7$, G is $CR^8$, $R^5$ is —$W[C(O)]_kZ(CR^9R^{10})_rCO_2R^{11}$, each of $R^6$, $R^7$ and $R^8$ is independently hydrogen, $C_{1-4}$ alkyl, $C_{1-4}$ alkoxy, $C_{1-4}$ alkoxycarbonyl, carboxyl, halo or hydroxyl and each of $R^9$, $R^{10}$, $R^{11}$, $R^{12}$, $R^{13}$, $R^{14}$, $R^{15}$, $R^{16}$ and $R^{17}$ is independently hydrogen or alkyl. Preferably $R^{18}$ is selected from the group consisting of hydrogen, $C_{1-4}$ alkyl, phenyl, substituted phenyl, benzyl and substituted benzyl. More preferably $R^{18}$ is hydrogen or methyl. Preferably, each of $R^6$, $R^7$ and $R^8$ is independently hydrogen or $C_{1-4}$ alkyl. More preferably, $R^6$, $R^7$ and $R^8$ is hydrogen. Preferably, each of $R^9$, $R^{10}$, $R^{11}$, $R^{12}$, $R^{13}$, $R^{14}$, $R^{15}$, $R^{16}$ and $R^{17}$ is independently hydrogen or $C_{1-4}$ alkyl.

In still other embodiments of a compound of Formula (I), n is 1, Y is a bond, $R^{18}$ is selected from the group consisting of hydrogen, alkyl, substituted alkyl, aryl, substituted aryl, arylalkyl, cycloalkyl, and heteroaryl, A is $CR^4$, B is $CR^5$, D is N, E is $CR^7$, G is $CR^8$, $R^5$ is —$W[C(O)]_kZ(CR^9R^{10})_rCO_2R^{11}$, each of $R^4$, $R^7$ and $R^8$ is independently hydrogen, $C_{1-4}$ alkyl, $C_{1-4}$ alkoxy, $C_{1-4}$ alkoxycarbonyl, carboxyl, halo or hydroxyl and each of $R^9$, $R^{10}$, $R^{11}$, $R^{12}$, $R^{13}$, $R^{14}$, $R^{15}$, $R^{16}$ and $R^{17}$ is independently hydrogen or alkyl. Preferably $R^{18}$ is selected from the group consisting of hydrogen, $C_{1-4}$ alkyl, phenyl, substituted phenyl, benzyl and substituted benzyl. More preferably $R^{18}$ is hydrogen or methyl. Preferably, each of $R^4$, $R^7$ and $R^8$ is independently hydrogen or $C_{1-4}$ alkyl. More preferably, $R^4$, $R^7$ and $R^8$ are hydrogen. Preferably, each of $R^9$, $R^{10}$, $R^{11}$, $R^{12}$, $R^{13}$, $R^{14}$, $R^{15}$, $R^{16}$ and $R^{17}$ is independently hydrogen or $C_{1-4}$ alkyl.

In still other embodiments of a compound of Formula (I), n is 1, Y is a bond, $R^{18}$ is selected from the group consisting of hydrogen, alkyl, substituted alkyl, aryl, substituted aryl, arylalkyl, cycloalkyl, and heteroaryl, A is $CR^4$, B is $CR^5$, D is $CR^6$, E is N, G is $CR^8$, $R^5$ is —$W[C(O)]_kZ(CR^9R^{10})_rCO_2R^{11}$, each of $R^4$, $R^6$ and $R^8$ is independently hydrogen, $C_{1-4}$ alkyl, $C_{1-4}$ alkoxy, $C_{1-4}$ alkoxycarbonyl, carboxyl, halo or hydroxyl and each of $R^9$, $R^{10}$, $R^{11}$, $R^{12}$, $R^{13}$, $R^{14}$, $R^{15}$, $R^{16}$ and $R^{17}$ is independently hydrogen or alkyl. Preferably $R^{18}$ is selected from the group consisting of hydrogen, $C_{1-4}$ alkyl, phenyl, substituted phenyl, benzyl and substituted benzyl. More preferably $R^{18}$ is hydrogen or methyl. Preferably, each of $R^4$, $R^6$ and $R^8$ is independently hydrogen or $C_{1-4}$ alkyl. More preferably, $R^4$, $R^6$ and $R^8$ are hydrogen. Preferably, each of $R^9$, $R^{10}$, $R^{11}$, $R^{12}$, $R^{13}$, $R^{14}$, $R^{15}$, $R^{16}$ and $R^{17}$ is independently hydrogen or $C_{1-4}$ alkyl.

In still other embodiments of a compound of Formula (I), n is 1, Y is a bond, $R^{18}$ is selected from the group consisting of hydrogen, alkyl, substituted alkyl, aryl, substituted aryl, arylalkyl, cycloalkyl, and heteroaryl, A is $CR^4$, B is $CR^5$, D is $CR^6$, E is $CR^7$, G is N, $R^5$ is —$W[C(O)]_kZ(CR^9R^{10})_rCO_2R^{11}$, each of $R^4$, $R^5$ and $R^7$ is independently hydrogen, $C_{1-4}$ alkyl, $C_{1-4}$ alkoxy, $C_{1-4}$ alkoxycarbonyl, carboxyl, halo or hydroxyl and each of $R^9$, $R^{10}$, $R^{11}$, $R^{12}$, $R^{13}$, $R^{14}$, $R^{15}$, $R^{16}$ and $R^{17}$ is independently hydrogen or alkyl. Preferably $R^{18}$ is selected from the group consisting of hydrogen, $C_{1-4}$ alkyl, phenyl, substituted phenyl, benzyl and substituted benzyl. More preferably $R^{18}$ is hydrogen or methyl. Preferably, each of $R^4$, $R^5$ and $R^7$ is independently hydrogen or $C_{1-4}$ alkyl. More preferably, $R^4$, $R^5$ and $R^7$ are hydrogen. Preferably, each of $R^9$, $R^{10}$, $R^{11}$, $R^{12}$, $R^{13}$, $R^{14}$, $R^{15}$, $R^{16}$ and $R^{17}$ is independently hydrogen or $C_{1-4}$ alkyl.

In still other embodiments of a compound of Formula (I), n is 1, Y is a bond, $R^{18}$ is selected from the group consisting of hydrogen, alkyl, substituted alkyl, aryl, substituted aryl, arylalkyl, cycloalkyl, and heteroaryl, A is N, B is $CR^5$, D is $CR^6$, E is $CR^7$, G is N, $R^5$ is $-W[C(O)]_kZ(CR^9R^{10})_r$ $CO_2R^{11}$, each of $R^6$ and $R^7$ is independently hydrogen, $C_{1-4}$ alkyl, $C_{1-4}$ alkoxy, $C_{1-4}$ alkoxycarbonyl, carboxyl, halo or hydroxyl and each of $R^9$, $R^{10}$, $R^{11}$, $R^{12}$, $R^{13}$, $R^{14}$, $R^{15}$, $R^{16}$ and $R^{17}$ is independently hydrogen or alkyl. Preferably $R^{18}$ is selected from the group consisting of hydrogen, $C_{1-4}$ alkyl, phenyl, substituted phenyl, benzyl and substituted benzyl. More preferably $R^{18}$ is hydrogen or methyl. Preferably, each of $R^6$ and $R^7$ is independently hydrogen or $C_{1-4}$ alkyl. More preferably, $R^6$ and $R^7$ are hydrogen. Preferably, each of $R^9$, $R^{10}$, $R^{11}$, $R^{12}$, $R^{13}$, $R^{14}$, $R^{15}$, $R^{16}$ and $R^{17}$ is independently hydrogen or $C_{1-4}$ alkyl.

In still other embodiments of a compound of Formula (I), n is 1, Y is a bond, $R^{18}$ is selected from the group consisting of hydrogen, alkyl, substituted alkyl, aryl, substituted aryl, arylalkyl, cycloalkyl, and heteroaryl, A is N, B is $CR^5$, D is N, E is $CR^7$, G is $CR^8$, $R^5$ is $-W[C(O)]_kZ(CR^9R^{10})_r$ $CO_2R^{11}$, each of $R^7$ and $R^8$ is independently hydrogen, $C_{1-4}$ alkyl, $C_{1-4}$ alkoxy, $C_{1-4}$ alkoxycarbonyl, carboxyl, halo or hydroxyl and each of $R^9$, $R^{10}$, $R^{11}$, $R^{12}$, $R^{13}$, $R^{14}$, $R^{15}$, $R^{16}$ and $R^{17}$ is independently hydrogen or alkyl. Preferably $R^{18}$ is selected from the group consisting of hydrogen, $C_{1-4}$ alkyl, phenyl, substituted phenyl, benzyl and substituted benzyl. More preferably $R^{18}$ is hydrogen or methyl. Preferably, each of $R^7$ and $R^8$ is independently hydrogen or $C_{1-4}$ alkyl. More preferably, $R^7$ and $R^8$ are hydrogen. Preferably, each of $R^9$, $R^{10}$, $R^{11}$, $R^{12}$, $R^{13}$, $R^{14}$, $R^{15}$, $R^{16}$ and $R^{17}$ is independently hydrogen or $C_{1-4}$ alkyl.

In still other embodiments of a compound of Formula (I), n is 1, Y is a bond, $R^{18}$ is selected from the group consisting of hydrogen, alkyl, substituted alkyl, aryl, substituted aryl, arylalkyl, cycloalkyl, and heteroaryl, A is N, B is $CR^5$, D is $CR^6$, E is N, G is $CR^8$, $R^5$ is $-W[C(O)]_kZ(CR^9R^{10})_r$ $CO_2R^{11}$, each of $R^6$ and $R^8$ is independently hydrogen, $C_{1-4}$ alkyl, $C_{1-4}$ alkoxy, $C_{1-4}$ alkoxycarbonyl, carboxyl, halo or hydroxyl and each of $R^9$, $R^{10}$, $R^{11}$, $R^{12}$, $R^{13}$, $R^{14}$, $R^{15}$, $R^{16}$ and $R^{17}$ is independently hydrogen or alkyl. Preferably $R^{18}$ is selected from the group consisting of hydrogen, $C_{1-4}$ alkyl, phenyl, substituted phenyl, benzyl and substituted benzyl. More preferably $R^{18}$ is hydrogen or methyl. Preferably, each of $R^6$ and $R^8$ is independently hydrogen or $C_{1-4}$ alkyl. More preferably, $R^6$ and $R^8$ are hydrogen. Preferably, each of $R^9$, $R^{10}$, $R^{11}$, $R^{12}$, $R^{13}$, $R^{14}$, $R^{15}$, $R^{16}$ and $R^{17}$ is independently hydrogen or $C_{1-4}$ alkyl.

In still other embodiments of a compound of Formula (1), n is 1, Y is a bond, $R^{18}$ is selected from the group consisting of hydrogen, alkyl, substituted alkyl, aryl, substituted aryl, arylalkyl, cycloalkyl, and heteroaryl, A is $CR^4$, B is $CR^5$, D is N, E is $CR^7$, G is N, $R^5$ is $-W[C(O)]_kZ(CR^9R^{10})_r$ $CO_2R^{11}$, each of $R^4$ and $R^8$ is independently hydrogen, $C_{1-4}$ alkyl, $C_{1-4}$ alkoxy, $C_{1-4}$ alkoxycarbonyl, carboxyl, halo or hydroxyl and each of $R^9$, $R^{10}$, $R^{11}$, $R^{12}$, $R^{13}$, $R^{14}$, $R^{15}$, $R^{16}$ and $R^{17}$ is independently hydrogen or alkyl. Preferably $R^{18}$ is selected from the group consisting of hydrogen, $C_{1-4}$ alkyl, phenyl, substituted phenyl, benzyl and substituted benzyl. More preferably $R^{18}$ is hydrogen or methyl. Preferably, each of $R^4$ and $R^8$ is independently hydrogen or $C_{1-4}$ alkyl. More preferably, $R^4$ and $R^8$ are hydrogen. Preferably, each of $R^9$, $R^{10}$, $R^{11}$, $R^{12}$, $R^{13}$, $R^{14}$, $R^{15}$, $R^{16}$ and $R^{17}$ is independently hydrogen or $C_{1-4}$ alkyl.

In still other embodiments of a compound of Formula (I), n is 1, Y is a bond, $R^{18}$ is selected from the group consisting of hydrogen, alkyl, substituted alkyl, aryl, substituted aryl, arylalkyl, cycloalkyl, and heteroaryl, A is $CR^4$, B is $CR^5$, D is $CR^6$, E is $CR^7$, G is $CR^8$, $R^6$ is $-W[C(O)]_kZ(CR^9R^{10})_r$ $CO_2R^{11}$, each of $R^4$, $R^5$, $R^7$ and $R^8$ is independently hydrogen, $C_{1-4}$ alkyl, $C_{1-4}$ alkoxy, $C_{1-4}$ alkoxycarbonyl, carboxyl, halo or hydroxyl and each of $R^9$, $R^{10}$, $R^{11}$, $R^{12}$, $R^{13}$, $R^{14}$, $R^{15}$, $R^{16}$ and $R^{17}$ is independently hydrogen or alkyl. Preferably $R^{18}$ is selected from the group consisting of hydrogen, $C_{1-4}$ alkyl, phenyl, substituted phenyl, benzyl and substituted benzyl. More preferably, $R^{18}$ is hydrogen or methyl. Preferably, each of $R^4$, $R^5$, $R^7$ and $R^8$ is independently hydrogen or $C_{1-4}$ alkyl. More preferably, $R^4$, $R^5$, $R^7$ and $R^8$ are hydrogen. Preferably, each of $R^9$, $R^{10}$, $R^{11}$, $R^{12}$, $R^{13}$, $R^{14}$, $R^{15}$, $R^{16}$ and $R^{17}$ is independently hydrogen or $C_{1-4}$ alkyl.

In still other embodiments of a compound of Formula (I), n is 1, Y is a bond, $R^{18}$ is hydrogen or methyl, A is $CR^4$, B is $CR^5$, D is $CR^6$, E is $CR^7$, C is $CR^8$, $R^6$ is $-W[C(O)]_kZ$ $(CR^9R^{10})_rCO_2R^{11}$, each of $R^4$, $R^5$, $R^7$ and $R^8$ is independently hydrogen, $C_{1-4}$ alkyl, $C_{1-4}$ alkoxy, $C_{1-4}$ alkoxycarbonyl, carboxyl, halo or hydroxyl, W is a bond, k is 1, Z is $NR^{17}$, r is 1, and each of $R^9$, $R^{10}$, $R^{11}$ and $R^{17}$ is independently hydrogen or $C_{1-4}$ alkyl. Preferably, each of $R^4$, $R^5$, $R^7$ and $R^8$ is independently hydrogen or $C_{1-4}$ alkyl. More preferably, $R^4$, $R^5$, $R^7$ and $R^8$ are hydrogen. Preferably, $R^{11}$ and $R^{17}$ are hydrogen.

In still other embodiments of a compound of Formula (I), n is 1, Y is a bond, $R^{18}$ is hydrogen or methyl, A is $CR^4$, B is $CR^5$, D is $CR^6$, E is $CR^7$, G is $CR^8$, $R^6$ is $-W[C(O)]_kZ$ $(CR^9R^{10})_rCO_2R^{11}$, each of $R^4$, $R^5$, $R^7$ and $R^8$ is independently hydrogen, $C_{1-4}$ alkyl, $C_{1-4}$ alkoxy, $C_{1-4}$ alkoxycarbonyl, carboxyl, halo or hydroxyl, W is a bond, k is 1, Z is $NR^{17}$, r is 2, and each of $R^9$, $R^{10}$, $R^{11}$ and $R^{17}$ is independently hydrogen or $C_{1-4}$ alkyl. Preferably, each of $R^4$, $R^5$, $R^7$ and $R^8$ is independently hydrogen or $C_{1-4}$ alkyl. More preferably, $R^4$, $R^5$, $R^7$ and $R^8$ are hydrogen. Preferably, $R^{11}$ and $R^{17}$ are hydrogen.

In still other embodiments of a compound of Formula (I), n is 1, Y is a bond, $R^{18}$ is hydrogen or methyl, A is $CR^4$, B is $CR^5$, D is $CR^6$, E is $CR^7$, G is $CR^8$, $R^6$ is $-W[C(O)]_kZ$ $(CR^9R^{10})_rCO_2R^{11}$, each of $R^4$, $R^5$, $R^7$ and $R^8$ is independently hydrogen, $C_{1-4}$ alkyl, $C_{1-4}$ alkoxy, $C_{1-4}$ alkoxycarbonyl, carboxyl, halo or hydroxyl, W is a bond, k is 1, Z is O, r is 1, and each of $R^9$, $R^{10}$ and $R^{11}$ is independently hydrogen or $C_{1-4}$ alkyl. Preferably, each of $R^4$, $R^5$, $R^7$ and $R^8$ is independently hydrogen or $C_{1-4}$ alkyl. More preferably, $R^4$, $R^5$, $R^7$ and $R^8$ are hydrogen. Preferably, $R^{11}$ is hydrogen.

In still other embodiments of a compound of Formula (I), n is 1, Y is a bond, $R^{18}$ is hydrogen or methyl, A is $CR^4$, B is $CR^5$, D is $CR^6$, E is $CR^7$, G is $CR^8$, $R^6$ is $-W[C(O)]_kZ$ $(CR^9R^{10})_rCO_2R^{11}$, each of $R^4$, $R^5$, $R^7$ and $R^8$ is independently hydrogen, $C_{1-4}$ alkyl, $C_{1-4}$ alkoxy, $C_{1-4}$ alkoxycarbonyl, carboxyl, halo or hydroxyl, W is a bond, k is 1, Z is O, r is 2, and each of $R^9$, $R^{10}$ and $R^{11}$ is independently hydrogen or $C_{1-4}$ alkyl. Preferably, each of $R^4$, $R^5$, $R^7$ and $R^8$ is independently hydrogen or $C_{1-4}$ alkyl. More preferably, $R^4$, $R^5$, $R^7$ and $R^8$ are hydrogen. Preferably, $R^{11}$ is hydrogen.

In still other embodiments of a compound of Formula (I), n is 1, Y is a bond, $R^{18}$ is hydrogen or methyl, A is $CR^4$, B is $CR^5$, D is $CR^6$, E is $CR^7$, G is $CR^8$, $R^6$ is $-W[C(O)]_kZ$ $(CR^9R^{10})_rCO_2R^{11}$, each of $R^4$, $R^5$, $R^7$ and $R^8$ is independently hydrogen, $C_{1-4}$ alkyl, $C_{1-4}$ alkoxy, $C_{1-4}$ alkoxycarbonyl, carboxyl, halo or hydroxyl, W is O, k is 1, Z is $NR^{17}$, r is 1, and each of $R^9$, $R^{10}$, $R^{11}$ and $R^{17}$ is independently hydrogen or $C_{1-4}$ alkyl. Preferably, each of $R^4$, $R^5$, $R^7$ and $R^8$ is independently hydrogen or $C_{1-4}$ alkyl. More preferably, $R^4$, $R^5$, $R^7$ and $R^8$ are hydrogen. Preferably, $R^{11}$ and $R^{17}$ are hydrogen.

In still other embodiments of a compound of Formula (I), n is 1, Y is a bond, $R^{18}$ is hydrogen or methyl, A is $CR^4$, B is $CR^5$, D is $CR^6$, E is $CR^7$, G is $CR^8$, $R^6$ is —W[C(O)]$_k$Z(CR$^9$R$^{10}$)$_r$CO$_2$R$^{11}$, each of $R^4$, $R^5$, $R^7$ and $R^8$ is independently hydrogen, $C_{1-4}$ alkyl, $C_{1-4}$ alkoxy, $C_{1-4}$ alkoxycarbonyl, carboxyl, halo or hydroxyl, W is O, k is 1, Z is NR$^{17}$, r is 2, and each of $R^9$, $R^{10}$, $R^{11}$ and $R^{17}$ is independently hydrogen or $C_{1-4}$ alkyl. Preferably, each of $R^4$, $R^5$, $R^7$ and $R^8$ is independently hydrogen or $C_{1-4}$ alkyl. More preferably, $R^4$, $R^5$, $R^7$ and $R^8$ are hydrogen. Preferably, $R^{11}$ and $R^{17}$ are hydrogen.

In still other embodiments of a compound of Formula (I), n is 1, Y is a bond, $R^{18}$ is hydrogen or methyl, A is $CR^4$, B is $CR^5$, D is $CR^6$, E is $CR^7$, G is $CR^8$, $R^6$ is —W[C(O)]$_k$Z(CR$^9$R$^{10}$)$_r$CO$_2$R$^{11}$, each of $R^4$, $R^5$, $R^7$ and $R^8$ is independently hydrogen, $C_{1-4}$ alkyl, $C_{1-4}$ alkoxy, $C_{1-4}$ alkoxycarbonyl, carboxyl, halo or hydroxyl, W is O, k is 1, Z is O, r is 1, and each of $R^9$, $R^{10}$ and $R^{11}$ is independently hydrogen or $C_{1-4}$ alkyl. Preferably, each of $R^4$, $R^5$, $R^7$ and $R^8$ is independently hydrogen or $C_{1-4}$ alkyl. More preferably, $R^4$, $R^5$, $R^7$ and $R^8$ are hydrogen. Preferably, $R^{11}$ is hydrogen.

In still other embodiments of a compound of Formula (I), n is 1, Y is a bond, $R^{18}$ is hydrogen or methyl, A is $CR^4$, B is $CR^5$, D is $CR^6$, E is $CR^7$, G is $CR^8$, $R^6$ is —W[C(O)]$_k$Z(CR$^9$R$^{10}$)$_r$CO$_2$R$^{11}$, each of $R^4$, $R^5$, $R^7$ and $R^8$ is independently hydrogen, $C_{1-4}$ alkyl, $C_{1-4}$ alkoxy, $C_{1-4}$ alkoxycarbonyl, carboxyl, halo or hydroxyl, W is O, k is 1, Z is O, r is 2, and each of $R^9$, $R^{10}$ and $R^{11}$ is independently hydrogen or $C_{1-4}$ alkyl. Preferably, each of $R^4$, $R^5$, $R^7$ and $R^8$ is independently hydrogen or $C_{1-4}$ alkyl. More preferably, $R^4$, $R^5$, $R^7$ and $R^8$ are hydrogen. Preferably, $R^{11}$ is hydrogen.

In still other embodiments of a compound of Formula (I), n is 1, Y is a bond, $R^{18}$ is hydrogen or methyl, A is $CR^4$, B is $CR^5$, D is $CR^6$, E is $CR^7$, C is $CR^8$, $R^6$ is —W[C(O)]$_k$Z(CR$^9$R$^{10}$)$_r$CO$_2$R$^{11}$, each of $R^4$, $R^5$, $R^7$ and $R^8$ is independently hydrogen, $C_{1-4}$ alkyl, $C_{1-4}$ alkoxy, $C_{1-4}$ alkoxycarbonyl, carboxyl, halo or hydroxyl, W is O, k is 1, Z is CR$^{15}$R$^{16}$, r is 1, and each of $R^9$, $R^{10}$, $R^{11}$, $R^{15}$ and $R^{16}$ is independently hydrogen or $C_{1-4}$ alkyl. Preferably, each of $R^4$, $R^5$, $R^7$ and $R^8$ is independently hydrogen or $C_{1-4}$ alkyl. More preferably, $R^4$, $R^5$, $R^7$ and $R^8$ are hydrogen. Preferably, $R^{11}$, $R^{15}$ and $R^{16}$ are hydrogen.

In still other embodiments of a compound of Formula (I), n is 1, Y is a bond, $R^{18}$ is hydrogen or methyl, A is $CR^4$, B is $CR^5$, D is $CR^6$, E is $CR^7$, G is $CR^8$, $R^6$ is —W[C(O)]$_k$Z(CR$^9$R$^{10}$)$_r$CO$_2$R$^{11}$, each of $R^4$, $R^5$, $R^7$ and $R^8$ is independently hydrogen, $C_{1-4}$ alkyl, $C_{1-4}$ alkoxy, $C_{1-4}$ alkoxycarbonyl, carboxyl, halo or hydroxyl, W is O, k is 1, Z is CR$^{15}$R$^{16}$, r is 2, and each of $R^9$, $R^{10}$, $R^{11}$, $R^{15}$ and $R^{16}$ is independently hydrogen or $C_{1-4}$ alkyl. Preferably, each of $R^4$, $R^5$, $R^7$ and $R^8$ is independently hydrogen or $C_{1-4}$ alkyl. More preferably, $R^4$, $R^5$, $R^7$ and $R^8$ are hydrogen. Preferably, $R^{11}$, $R^{15}$ and $R^{16}$ are hydrogen.

In still other embodiments of a compound of Formula (I), n is 1, Y is a bond, $R^{18}$ is hydrogen or methyl, A is $CR^4$, B is $CR^5$, D is $CR^6$, E is $CR^7$, G is $CR^8$, $R^6$ is —W[C(O)]$_k$Z(CR$^9$R$^{10}$)$_r$CO$_2$R$^{11}$, each of $R^4$, $R^5$, $R^7$ and $R^8$ is independently hydrogen, $C_{1-4}$ alkyl, $C_{1-4}$ alkoxy, $C_{1-4}$ alkoxycarbonyl, carboxyl, halo or hydroxyl, W is NR$^{14}$, k is 1, Z is NR$^{17}$, r is 1 and each of $R^9$, $R^{10}$, $R^{11}$, $R^{14}$ and $R^{17}$ is independently hydrogen or $C_{1-4}$ alkyl. Preferably, each of $R^4$, $R^5$, $R^7$ and $R^8$ is independently hydrogen or $C_{1-4}$ alkyl. More preferably, $R^4$, $R^5$, $R^7$ and $R^8$ are hydrogen. Preferably, $R^{11}$, $R^{14}$ and $R^{17}$ are hydrogen.

In still other embodiments of a compound of Formula (I), n is 1, Y is a bond, $R^{18}$ is hydrogen or methyl, A is $CR^4$, B is $CR^5$, D is $CR^6$, E is $CR^7$, G is $CR^8$, $R^6$ is —W[C(O)]$_k$Z(CR$^9$R$^{10}$)$_r$CO$_2$R$^{11}$, each of $R^4$, $R^5$, $R^7$ and $R^8$ is independently hydrogen, $C_{1-4}$ alkyl, $C_{1-4}$ alkoxy, $C_{1-4}$ alkoxycarbonyl, carboxyl, halo or hydroxyl, W is NR$^{14}$, k is 1, Z is NR$^{17}$, r is 2 and each of $R^9$, $R^{10}$, $R^{11}$, $R^{14}$ and $R^{17}$ is independently hydrogen or $C_{1-4}$ alkyl. Preferably, each of $R^4$, $R^5$, $R^7$ and $R^8$ is independently hydrogen or $C_{1-4}$ alkyl. More preferably, $R^4$, $R^5$, $R^7$ and $R^8$ are hydrogen. Preferably, $R^{11}$, $R^{14}$ and $R^{17}$ are hydrogen.

In still other embodiments of a compound of Formula (I), n is 1, Y is a bond, $R^{18}$ is hydrogen or methyl, A is $CR^4$, B is $CR^5$, D is $CR^6$, E is $CR^7$, G is $CR^8$, $R^6$ is —W[C(O)]$_k$Z(CR$^9$R$^{10}$)$_r$CO$_2$R$^{11}$, each of $R^4$, $R^5$, $R^7$ and $R^8$ is independently hydrogen, $C_{1-4}$ alkyl, $C_{1-4}$ alkoxy, $C_{1-4}$ alkoxycarbonyl, carboxyl, halo or hydroxyl, W is NR$^{14}$, k is 1, Z is O, r is 1, and each of $R^9$, $R^{10}$, $R^{11}$ and $R^{14}$ is independently hydrogen or $C_{1-4}$ alkyl. Preferably, each of $R^4$, $R^5$, $R^7$ and $R^8$ is independently hydrogen or $C_{1-4}$ alkyl. More preferably, $R^4$, $R^5$, $R^7$ and $R^8$ are hydrogen. Preferably, each of $R^{11}$ and $R^{14}$ are hydrogen.

In still other embodiments of a compound of Formula (I), n is 1, Y is a bond, $R^{18}$ is hydrogen or methyl, A is $CR^4$, B is $CR^5$, D is $CR^6$, E is $CR^7$, G is $CR^8$, $R^6$ is —W[C(O)]$_k$Z(CR$^9$R$^{10}$)$_r$CO$_2$R$^{11}$, each of $R^4$, $R^5$, $R^7$ and $R^8$ is independently hydrogen, $C_{1-4}$ alkyl, $C_{1-4}$ alkoxy, $C_{1-4}$ alkoxycarbonyl, carboxyl, halo or hydroxyl, W is NR$^{14}$, k is 1, Z is O, r is 2, and each of $R^9$, $R^{10}$, $R^{11}$ and $R^{14}$ is independently hydrogen or $C_{1-4}$ alkyl. Preferably, each of $R^4$, $R^5$, $R^7$ and $R^8$ is independently hydrogen or $C_{1-4}$ alkyl. More preferably, $R^4$, $R^5$, $R^7$ and $R^8$ are hydrogen. Preferably, each of $R^{11}$ and $R^{14}$ are hydrogen.

In still other embodiments of a compound of Formula (I), n is 1, Y is a bond, $R^{18}$ is hydrogen or methyl, A is $CR^4$, B is $CR^5$, D is $CR^6$, E is $CR^7$, G is $CR^8$, $R^6$ is —W[C(O)]$_k$Z(CR$^9$R$^{10}$)$_r$CO$_2$R$^{11}$, each of $R^4$, $R^5$, $R^7$ and $R^8$ is independently hydrogen, $C_{1-4}$ alkyl, $C_{1-4}$ alkoxy, $C_{1-4}$ alkoxycarbonyl, carboxyl, halo or hydroxyl, W is NR$^{14}$, k is 1, Z is CR$^{15}$R$^{16}$, r is 1, and each of $R^9$, $R^{10}$, $R^{11}$, $R^{14}$, $R^{15}$ and $R^{16}$ is independently hydrogen or $C_{1-4}$ alkyl. Preferably, each of $R^4$, $R^5$, $R^7$ and $R^8$ is independently hydrogen or $C_{1-4}$ alkyl. More preferably, $R^4$, $R^5$, $R^7$ and $R^8$ are hydrogen. Preferably, $R^{11}$, $R^{14}$, $R^{15}$ and $R^{16}$ are hydrogen.

In still other embodiments of a compound of Formula (I), n is 1, Y is a bond, $R^{18}$ is hydrogen or methyl, A is $CR^4$, B is $CR^5$, D is $CR^6$, E is $CR^7$, G is $CR^8$, $R^6$ is —W[C(O)]$_k$Z(CR$^9$R$^{10}$)$_r$CO$_2$R$^{11}$, each of $R^5$, $R^5$, $R^7$ and $R^8$ is independently hydrogen, $C_{1-4}$ alkyl, $C_{1-4}$ alkoxy, $C_{1-4}$ alkoxycarbonyl, carboxyl, halo or hydroxyl, W is NR$^{14}$, k is 1, Z is CR$^{15}$R$^{16}$, r is 2, and each of $R^9$, $R^{10}$, $R^{11}$, $R^{14}$, $R^{15}$ and $R^{16}$ is independently hydrogen or $C_{1-4}$ alkyl. Preferably, each of $R^4$, $R^5$, $R^7$ and $R^8$ is independently hydrogen or $C_{1-4}$ alkyl. More preferably, $R^4$, $R^5$, $R^7$ and $R^8$ are hydrogen. Preferably, $R^{11}$, $R^{14}$, $R^{15}$ and $R^{16}$ are hydrogen.

In still other embodiments of a compound of Formula (I), n is 1, Y is a bond, $R^{18}$ is selected from the group consisting of hydrogen, alkyl, substituted alkyl, aryl, substituted aryl, arylalkyl, cycloalkyl, and heteroaryl, A is N, B is $CR^5$, D is $CR^6$, E is $CR^7$, G is $CR^8$, $R^6$ is —W[C(O)]$_k$Z(CR$^9$R$^{10}$)$_r$CO$_2$R$^{11}$, each of $R^5$, $R^7$ and $R^8$ is independently hydrogen, $C_{1-4}$ alkyl, $C_{1-4}$ alkoxy, $C_{1-4}$ alkoxycarbonyl, carboxyl, halo or hydroxyl and each of $R^9$, $R^{10}$, $R^{11}$, $R^{12}$, $R^{13}$, $R^{14}$, $R^{15}$, $R^{16}$ and $R^{17}$ is independently hydrogen or alkyl. Preferably $R^{18}$ is selected from the group consisting of hydrogen, $C_{1-4}$ alkyl, phenyl, substituted phenyl, benzyl and substituted benzyl. More preferably $R^{18}$ is hydrogen or methyl. Preferably, each of $R^5$, $R^7$ and $R^8$ is independently hydrogen or $C_{1-4}$ alkyl. More preferably, $R^5$, $R^7$ and $R^8$ are hydrogen.

Preferably, each of $R^9$, $R^{10}$, $R^{11}$, $R^{12}$, $R^{13}$, $R^{14}$, $R^{15}$, $R^{16}$ and $R^{17}$ is independently hydrogen or $C_{1-4}$ alkyl.

In still other embodiments of a compound of Formula (I), n is 1, Y is a bond, $R^{18}$ is selected from the group consisting of hydrogen, alkyl, substituted alkyl, aryl, substituted aryl, arylalkyl, cycloalkyl, and heteroaryl, A is $CR^4$, B is N, D is $CR^6$, E is $CR^7$, G is $CR^8$, $R^6$ is —$W[C(O)]_kZ(CR^9R^{10})_r$ $CO_2R^{11}$, each of $R^4$, $R^7$ and $R^8$ is independently hydrogen, $C_{1-4}$ alkyl, $C_{1-4}$ alkoxy, $C_{1-4}$ alkoxycarbonyl, carboxyl, halo or hydroxyl and each of $R^9$, $R^{10}$, $R^{11}$, $R^{12}$, $R^{13}$, $R^{14}$, $R^{15}$, $R^{16}$ and $R^{17}$ is independently hydrogen or alkyl. Preferably $R^{18}$ is selected from the group consisting of hydrogen, $C_{1-4}$ alkyl, phenyl, substituted phenyl, benzyl and substituted benzyl. More preferably $R^{18}$ is hydrogen or methyl. Preferably, each of $R^4$, $R^7$ and $R^8$ is independently hydrogen or $C_{1-4}$ alkyl. More preferably, $R^4$, $R^7$ and $R^8$ are hydrogen. Preferably, each of $R^9$, $R^{10}$, $R^{11}$, $R^{12}$, $R^{13}$, $R^{14}$, $R^{15}$, $R^{16}$ and $R^{17}$ is independently hydrogen or $C_{1-4}$ alkyl.

In still other embodiments of a compound of Formula (I), n is 1, Y is a bond, $R^{18}$ is selected from the group consisting of hydrogen, alkyl, substituted alkyl, aryl, substituted aryl, arylalkyl, cycloalkyl, and heteroaryl, A is N, B is $CR^5$, D is $CR^6$, E is $CR^7$, G is N, $R^6$ is —$W[C(O)]_kZ(CR^9R^{10})_r$ $CO_2R^{11}$, each of $R^5$ and $R^7$ is independently hydrogen, $C_{1-4}$ alkyl, $C_{1-4}$ alkoxy, $C_{1-4}$ alkoxycarbonyl, carboxyl, halo or hydroxyl and each of $R^9$, $R^{10}$, $R^{11}$, $R^{12}$, $R^{13}$, $R^{14}$, $R^{15}$, $R^{16}$ and $R^{17}$ is independently hydrogen or alkyl. Preferably $R^{18}$ is selected from the group consisting of hydrogen, $C_{1-4}$ alkyl, phenyl, substituted phenyl, benzyl and substituted benzyl. More preferably $R^{18}$ is hydrogen or methyl. Preferably, each of $R^5$ and $R^7$ is independently hydrogen or $C_{1-4}$ alkyl. More preferably, $R^5$ and $R^7$ are hydrogen. Preferably, each of $R^9$, $R^{10}$, $R^{11}$, $R^{12}$, $R^{13}$, $R^{14}$, $R^{15}$, $R^{16}$ and $R^{17}$ is independently hydrogen or $C_{1-4}$ alkyl.

In still other embodiments of a compound of Formula (I), n is 1, Y is a bond, $R^{18}$ is selected from the group consisting of hydrogen, alkyl, substituted alkyl, aryl, substituted aryl, arylalkyl, cycloalkyl, and heteroaryl, A is $CR^4$, B is $CR^5$, D is $CR^6$, E is N, G is $CR^8$, $R^6$ is —$W[C(O)]_kZ(CR^9R^{10})_r$ $CO_2R^{11}$, each of $R^5$ and $R^8$ is independently hydrogen, $C_{1-4}$ alkyl, $C_{1-4}$ alkoxy, $C_{1-4}$ alkoxycarbonyl, carboxyl, halo or hydroxyl and each of $R^9$, $R^{10}$, $R^{11}$, $R^{12}$, $R^{13}$, $R^{14}$, $R^{15}$, $R^{16}$ and $R^{17}$ is independently hydrogen or alkyl. Preferably $R^{18}$ is selected from the group consisting of hydrogen, $C_{1-4}$ alkyl, phenyl, substituted phenyl, benzyl and substituted benzyl. More preferably $R^{18}$ is hydrogen or methyl. Preferably, each of $R^5$ and $R^8$ is independently hydrogen or $C_{1-4}$ alkyl. More preferably, $R^5$ and $R^8$ are hydrogen. Preferably, each of $R^9$, $R^{10}$, $R^{11}$, $R^{12}$, $R^{13}$, $R^{14}$, $R^{15}$, $R^{16}$ and $R^{17}$ is independently hydrogen or $C_{1-4}$ alkyl.

In still other embodiments of a compound of Formula (I), n is 1, Y is a bond, $R^{18}$ is selected from the group consisting of hydrogen, alkyl, substituted alkyl, aryl, substituted aryl, arylalkyl, cycloalkyl, and heteroaryl, A is $CR^4$, B is N. D is $CR^6$, E is N, G is $CR^8$, $R^6$ is —$W[C(O)]_kZ(CR^9R^{10})_r$ $CO_2R^{11}$, each of $R^4$ and $R^8$ is independently hydrogen, $C_{1-4}$ alkyl, $C_{1-4}$ alkoxy, $C_{1-4}$ alkoxycarbonyl, carboxyl, halo or hydroxyl and each of $R^9$, $R^{10}$, $R^{11}$, $R^{12}$, $R^{13}$, $R^{14}$, $R^{15}$, $R^{16}$ and $R^{17}$ is independently hydrogen or alkyl. Preferably $R^{18}$ is selected from the group consisting of hydrogen, $C_{1-4}$ alkyl, phenyl, substituted phenyl, benzyl and substituted benzyl. More preferably $R^{18}$ is hydrogen or methyl. Preferably, each of $R^4$ and $R^8$ is independently hydrogen or $C_{1-4}$ alkyl. More preferably, $R^4$ and $R^8$ are hydrogen. Preferably, each of $R^9$, $R^{10}$, $R^{11}$, $R^{12}$, $R^{13}$, $R^{14}$, $R^{15}$, $R^{16}$ and $R^{17}$ is independently hydrogen or $C_{1-4}$ alkyl.

In still other embodiments of a compound of Formula (I), n is 1, Y is O, $R^{18}$ is selected from the group consisting of hydrogen, alkyl, substituted alkyl, aryl, substituted aryl, arylalkyl, cycloalkyl and heteroaryl, A is $CR^4$, B is $CR^5$, D is $CR^6$, E is $CR^7$, G is $CR^8$, $R^4$ is —$W[C(O)]_kZ(CR^9R^{10})_r$ $CO_2R^{11}$, each of $R^5$, $R^6$, $R^7$ and $R^8$ is independently hydrogen, $C_{1-4}$ alkyl, $C_{1-4}$ alkoxy, $C_{1-4}$ alkoxycarbonyl, carboxyl, halo or hydroxyl and each of $R^9$, $R^{10}$, $R^{11}$, $R^{12}$, $R^{13}$, $R^{14}$, $R^{15}$, $R^{16}$ and $R^{17}$ is independently hydrogen or alkyl. Preferably, each of $R^5$, $R^6$, $R^7$ and $R^8$ is independently hydrogen or $C_{1-4}$ alkyl. More preferably, $R^5$, $R^6$, $R^7$ and $R^8$ are hydrogen. Preferably, each of $R^9$, $R^{10}$, $R^{11}$, $R^{12}$, $R^{13}$, $R^{14}$, $R^{15}$, $R^{16}$ and $R^{17}$ is independently hydrogen or $C_{1-4}$ alkyl.

In still other embodiments of a compound of Formula (I), n is 1, Y is O, $R^{18}$ is hydrogen or methyl, A is $CR^4$, B is $CR^5$, D is $CR^6$, E is $CR^7$, G is $CR^8$, $R^4$ is —$W[C(O)]_kZ(CR^9R^{10})_r$ $CO_2R^{11}$, each of $R^5$, $R^6$, $R^7$ and $R^8$ is independently hydrogen, $C_{1-4}$ alkyl, $C_{1-4}$ alkoxy, $C_{1-4}$ alkoxycarbonyl, carboxyl, halo or hydroxyl, W is a bond, k is 1, Z is $NR^{17}$, r is 1, and each of $R^9$, $R^{10}$, $R^{11}$ and $R^{17}$ is independently hydrogen or $C_{1-4}$ alkyl. Preferably, each of $R^5$, $R^6$, $R^7$ and $R^8$ is independently hydrogen or $C_{1-4}$ alkyl. More preferably, $R^5$, $R^6$, $R^7$ and $R^8$ are hydrogen. Preferably, $R^{11}$ and $R^{17}$ are hydrogen.

In still other embodiments of a compound of Formula (I), n is 1, Y is O, $R^{18}$ is hydrogen or methyl, A is $CR^4$, B is $CR^5$, D is $CR^6$, E is $CR^7$, G is $CR^8$, $R^4$ is —$W[C(O)]_kZ(CR^9R^{10})_r$ $CO_2R^{11}$, each of $R^5$, $R^6$, $R^7$ and $R^8$ is independently hydrogen, $C_{1-4}$ alkyl, $C_{1-4}$ alkoxy, $C_{1-4}$ alkoxycarbonyl, carboxyl, halo or hydroxyl, W is a bond, k is 1, Z is $NR^{17}$, r is 2, and each of $R^9$, $R^{10}$, $R^{11}$ and $R^{17}$ is independently hydrogen or $C_{1-4}$ alkyl. Preferably, each of $R^5$, $R^6$, $R^7$ and $R^8$ is independently hydrogen or $C_{1-4}$ alkyl. More preferably, $R^5$, $R^6$, $R^7$ and $R^8$ are hydrogen. Preferably, $R^{11}$ and $R^{17}$ are hydrogen.

In still other embodiments of a compound of Formula (I), n is 1, Y is O, $R^{18}$ is hydrogen or methyl, A is $CR^4$, B is $CR^5$, D is $CR^6$ E is $CR^7$, G is $CR^8$, $R^4$ is —$W[C(O)]_kZ(CR^9R^{10})_r$ $CO_2R^{11}$, each of $R^5$, $R^6$, $R^7$ and $R^8$ is independently hydrogen, $C_{1-4}$ alkyl, $C_{1-4}$ alkoxy, $C_{1-4}$ alkoxycarbonyl, carboxyl, halo or hydroxyl, W is a bond, k is 1, Z is O, r is 1, and each of $R^9$, $R^{10}$ and $R^{11}$ is independently hydrogen or $C_{1-4}$ alkyl. Preferably, each of $R^5$, $R^6$, $R^7$ and $R^8$ is independently hydrogen or $C_{1-4}$ alkyl. More preferably, $R^5$, $R^6$, $R^7$ and $R^8$ are hydrogen. Preferably, $R^{11}$ is hydrogen.

In still other embodiments of a compound of Formula (I), n is 1, Y is O, $R^{18}$ is hydrogen or methyl, A is $CR^4$, B is $CR^5$, D is $CR^6$, E is $CR^7$, G is $CR^8$, $R^4$ is —$W[C(O)]_kZ(CR^9R^{10})_r$ $CO_2R^{11}$, each of $R^5$, $R^6$, $R^7$ and $R^8$ is independently hydrogen, $C_{1-4}$ alkyl, $C_{1-4}$ alkoxy, $C_{1-4}$ alkoxycarbonyl, carboxyl, halo or hydroxyl, W is a bond, k is 1, Z is O, r is 2, and each of $R^9$, $R^{10}$ and $R^{11}$ is independently hydrogen or $C_{1-4}$ alkyl. Preferably, each of $R^5$, $R^6$, $R^7$ and $R^8$ is independently hydrogen or $C_{1-4}$ alkyl. More preferably, $R^5$, $R^6$, $R^7$ and $R^8$ are hydrogen. Preferably, $R^{11}$ is hydrogen.

In still other embodiments of a compound of Formula (I), n is 1, Y is O, $R^{18}$ is hydrogen or methyl, A is $CR^4$, B is $CR^5$, D is $CR^6$, E is $CR^7$, G is $CR^8$, $R^4$ is —$W[C(O)]_kZ(CR^9R^{10})_r$ $CO_2R^{11}$, each of $R^5$, $R^6$, $R^7$ and $R^8$ is independently hydrogen, $C_{1-4}$ alkyl, $C_{1-4}$ alkoxy, $C_{1-4}$ alkoxycarbonyl, carboxyl, halo or hydroxyl, W is O, k is 1, Z is $NR^{17}$, r is 1, and each of $R^9$, $R^{10}$, $R^{11}$ and $R^{17}$ is independently hydrogen or $C_{1-4}$ alkyl. Preferably, each of $R^5$, $R^6$, $R^7$ and $R^8$ is independently hydrogen or $C_{1-4}$ alkyl. More preferably, $R^5$, $R^6$, $R^7$ and $R^8$ are hydrogen. Preferably, $R^{11}$ and $R^{17}$ are hydrogen.

In still other embodiments of a compound of Formula (I), n is 1, Y is O, $R^{18}$ is hydrogen or methyl, A is $CR^4$, B is $CR^5$, D is $CR^6$, E is $CR^7$, G is $CR^8$, $R^4$ is —W[C(O)]$_k$Z(CR$^9$R$^{10}$)$_r$-CO$_2$R$^{11}$, each of $R^5$, $R^6$, $R^7$ and $R^8$ is independently hydrogen, $C_{1-4}$ alkyl, $C_{1-4}$ alkoxy, $C_{1-4}$ alkoxycarbonyl, carboxyl, halo or hydroxyl, W is O, k is 1, Z is O, r is 1, and each of $R^9$, $R^{10}$ and $R^{11}$ is independently hydrogen or $C_{1-4}$ alkyl. Preferably, each of $R^5$, $R^6$, $R^7$ and $R^8$ is independently hydrogen or $C_{1-4}$ alkyl. More preferably, $R^5$, $R^6$, $R^7$ and $R^8$ are hydrogen. Preferably, $R^{11}$ and $R^{17}$ are hydrogen.

In still other embodiments of a compound of Formula (I), n is 1, Y is O, $R^{18}$ is hydrogen or methyl, A is $CR^4$, B is $CR^5$, D is $CR^6$, E is $CR^7$, G is $CR^8$, $R^4$ is —W[C(O)]$_k$Z(CR$^9$R$^{10}$)$_r$-CO$_2$R$^{11}$, each of $R^5$, $R^6$, $R^7$ and $R^8$ is independently hydrogen, $C_{1-4}$ alkyl, $C_{1-4}$ alkoxy, $C_{1-4}$ alkoxycarbonyl, carboxyl, halo or hydroxyl, W is O, k is 1, Z is O, r is 1, and each of $R^9$, $R^{10}$ and $R^{11}$ is independently hydrogen or $C_{1-4}$ alkyl. Preferably, each of $R^5$, $R^6$, $R^7$ and $R^8$ is independently hydrogen or $C_{1-4}$ alkyl. More preferably, $R^5$, $R^6$, $R^7$ and $R^8$ are hydrogen. Preferably, $R^{11}$ is hydrogen.

In still other embodiments of a compound of Formula (I), n is 1, Y is O, $R^{18}$ is hydrogen or methyl, A is $CR^4$, B is $CR^5$, D is $CR^6$, E is $CR^7$, G is $CR^8$, $R^4$ is —W[C(O)]$_k$Z(CR$^9$R$^{10}$)$_r$-CO$_2$R$^{11}$, each of $R^5$, $R^6$, $R^7$ and $R^8$ is independently hydrogen, $C_{1-4}$ alkyl, $C_{1-4}$ alkoxy, $C_{1-4}$ alkoxycarbonyl, carboxyl, halo or hydroxyl, W is O, k is 1, Z is O, r is 2, and each of $R^9$, $R^{10}$ and $R^{11}$ is independently hydrogen or $C_{1-4}$ alkyl. Preferably, each of $R^5$, $R^6$, $R^7$ and $R^8$ is independently hydrogen or $C_{1-4}$ alkyl. More preferably, $R^5$, $R^6$, $R^7$ and $R^8$ are hydrogen. Preferably, $R^{11}$ is hydrogen.

In still other embodiments of a compound of Formula (I), n is 1, Y is O, $R^{18}$ is hydrogen or methyl, A is $CR^4$, B is $CR^5$, D is $CR^6$, E is $CR^7$, G is $CR^8$, $R^4$ is —W[C(O)]$_k$Z(CR$^9$R$^{10}$)$_r$-CO$_2$R$^{11}$, each of $R^5$, $R^6$, $R^7$ and $R^8$ is independently hydrogen, $C_{1-4}$ alkyl, $C_{1-4}$ alkoxy, $C_{1-4}$ alkoxycarbonyl, carboxyl, halo or hydroxyl, W is O, k is 1, Z is $CR^{15}R^{16}$, r is 1, and each of $R^9$, $R^{10}$, $R^{11}$, $R^{15}$ and $R^{16}$ is independently hydrogen or $C_{1-4}$ alkyl. Preferably, each of $R^5$, $R^6$, $R^7$ and $R^8$ is independently hydrogen or $C_{1-4}$ alkyl. More preferably, $R^5$, $R^6$, $R^7$ and $R^8$ are hydrogen. Preferably, $R^{11}$, $R^{15}$ and $R^{16}$ are hydrogen.

In still other embodiments of a compound of Formula (I), n is 1, Y is O, $R^{18}$ is hydrogen or methyl, A is $CR^4$, B is $CR^5$, D is $CR^6$, E is $CR^7$, G is $CR^8$, $R^4$ is —W[C(O)]$_k$Z(CR$^9$R$^{10}$)$_r$-CO$_2$R$^{11}$, each of $R^5$, $R^6$, $R^7$ and $R^8$ is independently hydrogen, $C_{1-4}$ alkyl, $C_{1-4}$ alkoxy, $C_{1-4}$ alkoxycarbonyl, carboxyl, halo or hydroxyl, W is $CR^{15}R^{16}$, r is 2, and each of $R^9$, $R^{10}$, $R^{11}$, $R^{15}$ and $R^{16}$ is independently hydrogen or $C_{1-4}$ alkyl. Preferably, each of $R^5$, $R^6$, $R^7$ and $R^8$ is independently hydrogen or $C_{1-4}$ alkyl. More preferably, $R^5$, $R^6$, $R^7$ and $R^8$ are hydrogen. Preferably, $R^{11}$, $R^{15}$ and $R^{16}$ are hydrogen.

In still other embodiments of a compound of Formula (I), n is 1, Y is O, $R^{18}$ is hydrogen or methyl, A is $CR^4$, B is $CR^5$, D is $CR^6$, E is $CR^7$, G is $CR^8$, $R^4$ is —W[C(O)]$_k$Z(CR$^9$R$^{10}$)$_r$-CO$_2$R$^{11}$, each of $R^5$, $R^6$, $R^7$ and $R^8$ is independently hydrogen, $C_{1-4}$ alkyl, $C_{1-4}$ alkoxy, $C_{1-4}$ alkoxycarbonyl, carboxyl, halo or hydroxyl, W is $NR^{14}$, k is 1, Z is $NR^{17}$, r is 1 and each of $R^9$, $R^{10}$, $R^{11}$, $R^{14}$ and $R^{17}$ is independently hydrogen or $C_{1-4}$ alkyl. Preferably, each of $R^5$, $R^6$, $R^7$ and $R^8$ is independently hydrogen or $C_{1-4}$ alkyl. More preferably, $R^5$, $R^6$, $R^7$ and $R^8$ are hydrogen. Preferably, $R^{11}$, $R^{14}$ and $R^{17}$ are hydrogen.

In still other embodiments of a compound of Formula (I), n is 1, Y is O, $R^{18}$ is hydrogen or methyl, A is $CR^4$, B is $CR^5$, D is $CR^6$, E is $CR^7$, G is $CR^8$, $R^4$ is —W[C(O)]$_k$Z(CR$^9$R$^{10}$)$_r$-CO$_2$R$^{11}$, each of $R^5$, $R^6$, $R^7$ and $R^8$ is independently hydrogen, $C_{1-4}$ alkyl, $C_{1-4}$ alkoxy, $C_{1-4}$ alkoxycarbonyl, carboxyl, halo or hydroxyl, W is $NR^{14}$, k is 1, Z is $NR^{17}$, r is 2 and each of $R^9$, $R^{10}$, $R^{11}$, $R^{14}$ and $R^{17}$ is independently hydrogen or $C_{1-4}$ alkyl. Preferably, each of $R^5$, $R^6$, $R^7$ and $R^8$ is independently hydrogen or $C_{1-4}$ alkyl. More preferably, $R^5$, $R^6$, $R^7$ and $R^8$ are hydrogen. Preferably, $R^{11}$, $R^{14}$ and $R^{17}$ are hydrogen.

In still other embodiments of a compound of Formula (I), n is 1, Y is O, $R^{18}$ is hydrogen or methyl, A is $CR^4$, B is $CR^5$, D is $CR^6$, E is $CR^7$, G is $CR^8$, $R^4$ is —W[C(O)]$_k$Z(CR$^9$R$^{10}$)$_r$-CO$_2$R$^{11}$, each of $R^5$, $R^6$, $R^7$ and $R^8$ is independently hydrogen, $C_{1-4}$ alkyl, $C_{1-4}$ alkoxy, $C_{1-4}$ alkoxycarbonyl, carboxyl, halo or hydroxyl, W is $NR^{14}$, k is 1, Z is O, r is 1, and each of $R^9$, $R^{10}$, $R^{11}$ and $R^{14}$ is independently hydrogen or $C_{1-4}$ alkyl. Preferably, each of $R^5$, $R^6$, $R^7$ and $R^8$ is independently hydrogen or $C_{1-4}$ alkyl. More preferably, $R^5$, $R^6$, $R^7$ and $R^8$ are hydrogen. Preferably, each of $R^{11}$ and $R^{14}$ are hydrogen.

In still other embodiments of a compound of Formula (I), n is 1, Y is O, $R^{18}$ is hydrogen or methyl, A is $CR^4$, B is $CR^5$, D is $CR^6$, E is $CR^7$, G is $CR^8$, $R^4$ is —W[C(O)]$_k$Z(CR$^9$R$^{10}$)$_r$-CO$_2$R$^{11}$, each of $R^5$, $R^6$, $R^7$ and $R^8$ is independently hydrogen, $C_{1-4}$ alkyl, $C_{1-4}$ alkoxy, $C_{1-4}$ alkoxycarbonyl, carboxyl, halo or hydroxyl, W is $NR^{14}$, k is 1, Z is O, r is 2, and each of $R^9$, $R^{10}$, $R^{11}$ and $R^{14}$ is independently hydrogen or $C_{1-4}$ alkyl. Preferably, each of $R^5$, $R^6$, $R^7$ and $R^8$ is independently hydrogen or $C_{1-4}$ alkyl. More preferably, $R^5$, $R^6$, $R^7$ and $R^8$ are hydrogen. Preferably, each of $R^{11}$ and $R^{14}$ are hydrogen.

In still other embodiments of a compound of Formula (I), n is 1, Y is O, $R^{18}$ is hydrogen or methyl, A is $CR^4$, B is $CR^5$, D is $CR^6$, E is $CR^7$, G is $CR^8$, $R^4$ is —W[C(O)]$_k$Z(CR$^9$R$^{10}$)$_r$-CO$_2$R$^{11}$, each of $R^5$, $R^6$, $R^7$ and $R^8$ is independently hydrogen, $C_{1-4}$ alkyl, $C_{1-4}$ alkoxy, $C_{1-4}$ alkoxycarbonyl, carboxyl, halo or hydroxyl, W is $NR^{14}$, k is 1, Z is $CR^{15}R^{16}$, r is 1, and each of $R^9$, $R^{10}$, $R^{11}$, $R^{14}$, $R^{15}$ and $R^{16}$ is independently hydrogen or $C_{1-4}$ alkyl. Preferably, each of $R^5$, $R^6$, $R^7$ and $R^8$ is independently hydrogen or $C_{1-4}$ alkyl. More preferably, $R^5$, $R^6$, $R^7$ and $R^8$ are hydrogen. Preferably, $R^{11}$, $R^4$, $R^{15}$ and $R^{16}$ are hydrogen.

In still other embodiments of a compound of Formula (I), n is 1, Y is O, $R^{18}$ is hydrogen or methyl, A is $CR^4$, B is $CR^5$, D is $CR^6$, E is $CR^7$, G is $CR^8$, $R^4$ is —W[C(O)]$_k$Z(CR$^9$R$^{10}$)$_r$-CO$_2$R$^{11}$, each of $R^5$, $R^6$, $R^7$ and $R^8$ is independently hydrogen, $C_{1-4}$ alkyl, $C_{1-4}$ alkoxy, $C_{1-4}$ alkoxycarbonyl, carboxyl, halo or hydroxyl, W is $NR^{14}$, k is 1, Z is $CR^{15}R^{16}$, r is 2, and each of $R^9$, $R^{10}$, $R^{11}$, $R^{14}$, $R^{15}$ and $R^{16}$ is independently hydrogen or $C_{1-4}$ alkyl. Preferably, each of $R^5$, $R^6$, $R^7$ and $R^8$ is independently hydrogen or $C_{1-4}$ alkyl. More preferably, $R^5$, $R^6$, $R^7$ and $R^8$ are hydrogen. Preferably, $R^{11}$, $R^{14}$, $R^{15}$ and $R^{16}$ are hydrogen.

In still other embodiments of a compound of Formula (I), n is 1, Y is O, $R^{18}$ is selected from the group consisting of hydrogen, alkyl, substituted alkyl, aryl, substituted aryl, arylalkyl, cycloalkyl and heteroaryl, A is $CR^4$, B is $CR^5$, D is $CR^6$, E is $CR^7$, G is $CR^8$, $R^5$ is —W[C(O)]$_k$Z(CR$^9$R$^{10}$)$_r$-CO$_2$R$^{11}$, each of $R^4$, $R^6$, $R^7$ and $R^8$ is independently hydrogen, $C_{1-4}$ alkyl, $C_{1-4}$ alkoxy, $C_{1-4}$ alkoxycarbonyl, carboxyl, halo or hydroxyl and each of $R^9$, $R^{10}$, $R^{11}$, $R^{12}$, $R^{13}$, $R^{14}$, $R^{15}$, $R^{16}$ and $R^{17}$ is independently hydrogen or alkyl. Preferably, each of $R^4$, $R^6$, $R^7$ and $R^8$ is independently hydrogen or $C_{1-4}$ alkyl. More preferably, $R^4$, $R^6$, $R^7$ and $R^8$ are hydrogen. Preferably, each of $R^9$, $R^{10}$, $R^{11}$, $R^{12}$, $R^{13}$, $R^{14}$, $R^{15}$, $R^{16}$ and $R^{17}$ is independently hydrogen or $C_{1-4}$ alkyl.

In still other embodiments of a compound of Formula (I), n is 1, Y is O, $R^{18}$ is hydrogen or methyl, A is $CR^4$, B is $CR^5$, D is $CR^6$, E is $CR^7$, G is $CR^8$, $R^5$ is —$W[C(O)]_kZ(CR^9R^{10})_r$ $CO_2R^{11}$, each of $R^4$, $R^6$, $R^7$ and $R^8$ is independently hydrogen, $C_{1-4}$ alkyl, $C_{1-4}$ alkoxy, $C_{1-4}$ alkoxycarbonyl, carboxyl, halo or hydroxyl, W is a bond, k is 1, Z is $NR^{17}$, r is 1, and each of $R^9$, $R^{10}$, $R^{11}$ and $R^{17}$ is independently hydrogen or $C_{1-4}$ alkyl. Preferably, each of $R^4$, $R^6$, $R^7$ and $R^8$ is independently hydrogen or $C_{1-4}$ alkyl. More preferably, $R^4$, $R^6$, $R^7$ and $R^8$ are hydrogen. Preferably, $R^{11}$ and $R^{17}$ are hydrogen.

In still other embodiments of a compound of Formula (I), n is 1, Y is O, $R^{18}$ is hydrogen or methyl, A is $CR^4$, B is $CR^5$, D is $CR^6$, E is $CR^7$, G is $CR^8$, $R^5$ is —$W[C(O)]_kZ(CR^9R^{10})_r$ $CO_2R^{11}$, each of $R^4$, $R^6$, $R^7$ and $R^8$ is independently hydrogen, $C_{1-4}$ alkyl, $C_{1-4}$ alkoxy, $C_{1-4}$ alkoxycarbonyl, carboxyl, halo or hydroxyl, W is a bond, k is 1, Z is $NR^{17}$, r is 2, and each of $R^9$, $R^{10}$, $R^{11}$ and $R^{17}$ is independently hydrogen or $C_{1-4}$ alkyl. Preferably, each of $R^4$, $R^6$, $R^7$ and $R^8$ is independently hydrogen or $C_{1-4}$ alkyl. More preferably, $R^4$, $R^6$, $R^7$ and $R^8$ are hydrogen. Preferably, $R^{11}$ and $R^{17}$ are hydrogen.

In still other embodiments of a compound of Formula (I), n is 1, Y is O, $R^{18}$ is hydrogen or methyl, A is $CR^4$, B is $CR^5$, D is $CR^6$, E is $CR^7$, G is $CR^8$, $R^5$ is —$W[C(O)]_kZ(CR^9R^{10})_r$ $CO_2R^{11}$, each of $R^4$, $R^6$, $R^7$ and $R^8$ is independently hydrogen, $C_{1-4}$ alkyl, $C_{1-4}$ alkoxy, $C_{1-4}$ alkoxycarbonyl, carboxyl, halo or hydroxyl, W is a bond, k is 1, Z is O, r is 1, and each of $R^9$, $R^{10}$ and $R^{11}$ is independently hydrogen or $C_{1-4}$ alkyl. Preferably, each of $R^4$, $R^6$, $R^7$ and $R^8$ is independently hydrogen or $C_{1-4}$ alkyl. More preferably, each of $R^5$, $R^6$, $R^7$ and $R^8$ is hydrogen. Preferably, $R^{11}$ is hydrogen.

In still other embodiments of a compound of Formula (I), n is 1, Y is O, $R^{18}$ is hydrogen or methyl, A is $CR^4$, B is $CR^5$, D is $CR^6$, E is $CR^7$, G is $CR^8$, $R^5$ is —$W[C(O)]_kZ(CR^9R^{10})_r$ $CO_2R^{11}$, each of $R^4$, $R^6$, $R^7$ and $R^8$ is independently hydrogen, $C_{1-4}$ alkyl, $C_{1-4}$ alkoxy, $C_{1-4}$ alkoxycarbonyl, carboxyl, halo or hydroxyl, W is a bond, k is 1, Z is O, r is 2, and each of $R^9$, $R^{10}$ and $R^{11}$ is independently hydrogen or $C_{1-4}$ alkyl. Preferably, each of $R^4$, $R^6$, $R^7$ and $R^8$ is independently hydrogen or $C_{1-4}$ alkyl. More preferably, $R^4$, $R^6$, $R^7$ and $R^8$ are hydrogen. Preferably, $R^{11}$ is hydrogen.

In still other embodiments of a compound of Formula (I), n is 1, Y is O, $R^{18}$ is hydrogen or methyl, A is $CR^4$, B is $CR^5$, D is $CR^6$, E is $CR^7$, G is $CR^8$, $R^5$ is —$W[C(O)]_kZ(CR^9R^{10})_r$ $CO_2R^{11}$, each of $R^4$, $R^6$, $R^7$ and $R^8$ is independently hydrogen, $C_{1-4}$ alkyl, $C_{1-4}$ alkoxy, $C_{1-4}$ alkoxycarbonyl, carboxyl, halo or hydroxyl, W is O, k is 1, Z is $NR^{17}$, r is 1, and each of $R^9$, $R^{10}$, $R^{11}$ and $R^{17}$ is independently hydrogen or $C_{1-4}$ alkyl. Preferably, each of $R^4$, $R^6$, $R^7$ and $R^8$ is independently hydrogen or $C_{1-4}$ alkyl. More preferably, $R^5$, $R^6$, $R^7$ and $R^8$ are hydrogen. Preferably, $R^{11}$ and $R^{17}$ are hydrogen.

In still other embodiments of a compound of Formula (I), n is 1, Y is O, $R^{18}$ is hydrogen or methyl, A is $CR^4$, B is $CR^5$, D is $CR^6$, E is $CR^7$, G is $CR^8$, $R^5$ is —$W[C(O)]_kZ(CR^9R^{10})_r$ $CO_2R^{11}$, each of $R^4$, $R^6$, $R^7$ and $R^8$ is independently hydrogen, $C_{1-4}$ alkyl, $C_{1-4}$ alkoxy, $C_{1-4}$ alkoxycarbonyl, carboxyl, halo or hydroxyl, W is O, k is 1, Z is $NR^{17}$, r is 2, and each of $R^9$, $R^{10}$, $R^{11}$ and $R^{17}$ is independently hydrogen or $C_{1-4}$ alkyl. Preferably, each of $R^4$, $R^6$, $R^7$ and $R^8$ is independently hydrogen or $C_{1-4}$ alkyl. More preferably, $R^4$, $R^6$, $R^7$ and $R^8$ are hydrogen. Preferably, $R^{11}$ and $R^{17}$ are hydrogen.

In still other embodiments of a compound of Formula (I), n is 1, Y is O, $R^{18}$ is hydrogen or methyl, A is $CR^4$, B is $CR^5$, D is $CR^6$, E is $CR^7$, G is $CR^8$, $R^5$ is —$W[C(O)]_kZ(CR^9R^{10})_r$ $CO_2R^{11}$, each of $R^4$, $R^6$, $R^7$ and $R^8$ is independently hydrogen, $C_{1-4}$ alkyl, $C_{1-4}$ alkoxy, $C_{1-4}$ alkoxycarbonyl, carboxyl, halo or hydroxyl, W is O, k is 1, Z is O, r is 1, and each of $R^9$, $R^{10}$ and $R^{11}$ is independently hydrogen or $C_{1-4}$ alkyl. Preferably, each of $R^4$, $R^6$, $R^7$ and $R^8$ is independently hydrogen or $C_{1-4}$ alkyl. More preferably, each of $R^4$, $R^6$, $R^7$ and $R^8$ is hydrogen. Preferably, $R^{11}$ is hydrogen.

In still other embodiments of a compound of Formula (I), n is 1, Y is O, $R^{18}$ is hydrogen or methyl, A is $CR^4$, B is $CR^5$, D is $CR^6$, E is $CR^7$, G is $CR^8$, $R^5$ is —$W[C(O)]_kZ(CR^9R^{10})_r$ $CO_2R^{11}$, each of $R^4$, $R^6$, $R^7$ and $R^8$ is independently hydrogen, $C_{1-4}$ alkyl, $C_{1-4}$ alkoxy, $C_{1-4}$ alkoxycarbonyl, carboxyl, halo or hydroxyl, W is O, k is 1, Z is O, r is 2, and each of $R^9$, $R^{10}$ and $R^{11}$ is independently hydrogen or $C_{1-4}$ alkyl. Preferably, each of $R^4$, $R^6$, $R^7$ and $R^8$ is independently hydrogen or $C_{1-4}$ alkyl. More preferably, each of $R^4$, $R^6$, $R^7$ and $R^8$ is hydrogen. Preferably, $R^{11}$ is hydrogen.

In still other embodiments of a compound of Formula (I), n is 1, Y is O, $R^{18}$ is hydrogen or methyl, A is $CR^4$, B is $CR^5$, D is $CR^6$, E is $CR^7$, G is $CR^8$, $R^5$ is —$W[C(O)]_kZ(CR^9R^{10})_r$ $CO_2R^{11}$, each of $R^4$, $R^6$, $R^7$ and $R^8$ is independently hydrogen, $C_{1-4}$ alkyl, $C_{1-4}$ alkoxy, $C_{1-4}$ alkoxycarbonyl, carboxyl, halo or hydroxyl, W is O, k is 1, Z is $CR^{15}R^{16}$, r is 1, and each of $R^9$, $R^{10}$, $R^{11}$, $R^{15}$ and $R^{16}$ is independently hydrogen or $C_{1-4}$ alkyl. Preferably, each of $R^4$, $R^6$, $R^7$ and $R^8$ is independently hydrogen or $C_{1-4}$ alkyl. More preferably, $R^4$, $R^6$, $R^7$ and $R^8$ are hydrogen. Preferably, $R^{11}$, $R^{15}$ and $R^{16}$ are hydrogen.

In still other embodiments of a compound of Formula (I), n is 1, Y is O, $R^{18}$ is hydrogen or methyl, A is $CR^4$, B is $CR^5$, D is $CR^6$, E is $CR^7$, G is $CR^8$, $R^5$ is —$W[C(O)]_kZ(CR^9R^{10})_r$ $CO_2R^{11}$, each of $R^4$, $R^6$, $R^7$ and $R^8$ is independently hydrogen, $C_{1-4}$ alkyl, $C_{1-4}$ alkoxy, $C_{1-4}$ alkoxycarbonyl, carboxyl, halo or hydroxyl, W is O, k is 1, Z is $CR^{15}R^{16}$, r is 2, and each of $R^9$, $R^{10}$, $R^{11}$, $R^{15}$ and $R^{16}$ is independently hydrogen or $C_{1-4}$ alkyl. Preferably, each of $R^4$, $R^6$, $R^7$ and $R^8$ is independently hydrogen or $C_{1-4}$ alkyl. More preferably, $R^4$, $R^6$, $R^7$ and $R^8$ are hydrogen. Preferably, $R^{11}$, $R^{15}$ and $R^{16}$ are hydrogen.

In still other embodiments of a compound of Formula (I), n is 1, Y is O, $R^{18}$ is hydrogen or methyl, A is $CR^4$, B is $CR^5$, D is $CR^6$, E is $CR^7$, G is $CR^8$, $R^5$ is —$W[C(O)]_kZ(CR^9R^{10})_r$ $CO_2R^{11}$, each of $R^4$, $R^6$, $R^7$ and $R^8$ is independently hydrogen, $C_{1-4}$ alkyl, $C_{1-4}$ alkoxy, $C_{1-4}$ alkoxycarbonyl, carboxyl, halo or hydroxyl, W is $NR^{14}$, k is 1, Z is $NR^{17}$, r is 1 and each of $R^9$, $R^{10}$, $R^{11}$, $R^{14}$ and $R^{17}$ is independently hydrogen or $C_{1-4}$ alkyl. Preferably, each of $R^4$, $R^6$, $R^7$ and $R^8$ is independently hydrogen or $C_{1-4}$ alkyl. More preferably, $R^4$, $R^6$, $R^7$ and $R^8$ are hydrogen. Preferably, $R^{11}$, $R^{14}$ and $R^{17}$ are hydrogen.

In still other embodiments of a compound of Formula (I), n is 1, Y is O, $R^{18}$ is hydrogen or methyl, A is $CR^4$, B is $CR^5$, D is $CR^6$, E is $CR^7$, G is $CR^8$, $R^5$ is —$W[C(O)]_kZ(CR^9R^{10})_r$ $CO_2R^{11}$, each of $R^4$, $R^6$, $R^7$ and $R^8$ is independently hydrogen, $C_{1-4}$ alkyl, $C_{1-4}$ alkoxy, $C_{1-4}$ alkoxycarbonyl, carboxyl, halo or hydroxyl, W is $NR^{14}$, k is 1, Z is $NR^{17}$, r is 2 and each of $R^9$, $R^{10}$, $R^{11}$, $R^{14}$ and $R^{17}$ is independently hydrogen or $C_{1-4}$ alkyl. Preferably, each of $R^4$, $R^6$, $R^7$ and $R^8$ is independently hydrogen or $C_{1-4}$ alkyl. More preferably, $R^4$, $R^6$, $R^7$ and $R^8$ are hydrogen. Preferably, $R^{11}$, $R^{14}$ and $R^{17}$ are hydrogen.

In still other embodiments of a compound of Formula (I), n is 1, Y is O, $R^{18}$ is hydrogen or methyl, A is $CR^4$, B is $CR^5$, D is $CR^6$, E is $CR^7$, G is $CR^8$, $R^5$ is —$W[C(O)]_kZ(CR^9R^{10})_r$ $CO_2R^{11}$, each of $R^4$, $R^6$, $R^7$ and $R^8$ is independently hydrogen, $C_{1-4}$ alkyl, $C_{1-4}$ alkoxy, $C_{1-4}$ alkoxycarbonyl, carboxyl, halo or hydroxyl, W is $NR^{14}$, k is 1, Z is O, r is 1, and each of $R^9$, $R^{10}$, $R^{11}$ and $R^{14}$ is independently hydrogen or $C_{1-4}$ alkyl. Preferably, each of $R^4$, $R^6$, $R^7$ and $R^8$ is independently hydrogen or $C_{1-4}$ alkyl. More preferably, $R^4$, $R^6$, $R^7$ and $R^8$ are hydrogen. Preferably, each of $R^{11}$ and $R^{14}$ are hydrogen.

In still other embodiments of a compound of Formula (I), n is 1, Y is O, $R^{18}$ is hydrogen or methyl, A is $CR^4$, B is $CR^5$, D is $CR^6$, E is $CR^7$, G is $CR^8$, $R^5$ is $-W[C(O)]_kZ(CR^9R^{10})_r$ $CO_2R^{11}$, each of $R^4$, $R^6$, $R^7$ and $R^8$ is independently hydrogen, $C_{1-4}$ alkyl, $C_{1-4}$ alkoxy, $C_{1-4}$ alkoxycarbonyl, carboxyl, halo or hydroxyl, W is $NR^{14}$, k is 1, Z is O, r is 2, and each of $R^9$, $R^{10}$, $R^{11}$ and $R^{14}$ is independently hydrogen or $C_{1-4}$ alkyl. Preferably, each of $R^4$, $R^6$, $R^7$ and $R^8$ is independently hydrogen or $C_{1-4}$ alkyl. More preferably, $R^4$, $R^6$, $R^7$ and $R^8$ are hydrogen. Preferably, each of $R^{11}$ and $R^{14}$ are hydrogen.

In still other embodiments of a compound of Formula (I), n is 1, Y is O, $R^{18}$ is hydrogen or methyl, A is $CR^4$, B is $CR^5$, D is $CR^6$, E is $CR^7$, G is $CR^8$, $R^5$ is $-W[C(O)]_kZ(CR^9R^{10})_r$ $CO_2R^{11}$, each of $R^4$, $R^6$, $R^7$ and $R^8$ is independently hydrogen, $C_{1-4}$ alkyl, $C_{1-4}$ alkoxy, $C_{1-4}$ alkoxycarbonyl, carboxyl, halo or hydroxyl, W is $NR^{14}$, k is 1, Z is $CR^{15}R^{16}$, r is 1, and each of $R^9$, $R^{10}$, $R^{11}$, $R^{14}$, $R^{15}$ and $R^{16}$ is independently hydrogen or $C_{1-4}$ alkyl. Preferably, each of $R^4$, $R^6$, $R^7$ and $R^8$ is independently hydrogen or $C_{1-4}$ alkyl. More preferably, $R^4 R^6$, $R^7$ and $R^8$ are hydrogen. Preferably, $R^{11}$, $R^{14}$, $R^{15}$ and $R^{16}$ are hydrogen.

In still other embodiments of a compound of Formula (I), n is 1, Y is O, $R^{18}$ is hydrogen or methyl, A is $CR^4$, B is $CR^5$, D is $CR^6$, E is $CR^7$, G is $CR^8$, $R^5$ is $-W[C(O)]_kZ(CR^9R^{10})_r$ $CO_2R^{11}$, each of $R^4$, $R^6$, $R^7$, and $R^8$ is independently hydrogen, $C_{1-4}$ alkyl, $C_{1-4}$ alkoxy, $C_{1-4}$ alkoxycarbonyl, carboxyl, halo or hydroxyl, W is $NR^{14}$, k is 1, Z is $CR^{15}R^{16}$, r is 2, and each of $R^9$, $R^{10}$, $R^{11}$, $R^{14}$, $R^{15}$ and $R^{16}$ is independently hydrogen or $C_{1-4}$ alkyl. Preferably, each of $R^4$, $R^6$, $R^7$ and $R^8$ is independently hydrogen or $C_{1-4}$ alkyl. More preferably, $R^4$, $R^6$, $R^7$ and $R^8$ are hydrogen. Preferably, $R^{11}$, $R^{14}$, $R^{15}$ and $R^{16}$ are hydrogen.

In still other embodiments of a compound of Formula (I), n is 1, Y is O, $R^{18}$ is selected from the group consisting of hydrogen, alkyl, substituted alkyl, aryl, substituted aryl, arylalkyl, cycloalkyl, and heteroaryl, A is $CR^4$, B is $CR^5$, D is $CR^6$, E is $CR^7$, G is $CR^8$, $R^6$ is $-W[C(O)]_kZ(CR^9R^{10})_r$ $CO_2R^{11}$, each of $R^4$, $R^5$, $R^7$ and $R^8$ is independently hydrogen, $C_{1-4}$ alkyl, $C_{1-4}$ alkoxy, $C_{1-4}$ alkoxycarbonyl, carboxyl, halo or hydroxyl and each of $R^9$, $R^{10}$, $R^{11}$, $R^{12}$, $R^{13}$, $R^{14}$, $R^{15}$, $R^{16}$ and $R^{17}$ is independently hydrogen or alkyl. Preferably $R^{18}$ is selected from the group consisting of hydrogen, $C_{1-4}$ alkyl, phenyl, substituted phenyl, benzyl and substituted benzyl. More preferably, $R^{18}$ is hydrogen or methyl. Preferably, each of $R^4$, $R^5$, $R^7$ and $R^8$ is independently hydrogen or $C_{1-4}$ alkyl. More preferably, $R^4$, $R^5$, $R^7$ and $R^8$ are hydrogen. Preferably, each of $R^9$, $R^{10}$, $R^{11}$, $R^{12}$, $R^{13}$, $R^{14}$, $R^{15}$, $R^{16}$ and $R^{17}$ is independently hydrogen or $C_{1-4}$ alkyl.

In still other embodiments of a compound of Formula (I), n is 1, Y is O, $R^{18}$ is hydrogen or methyl, A is $CR^4$, B is $CR^5$, D is $CR^6$, E is $CR^7$, G is $CR^8$, $R^6$ is $-W[C(O)]_kZ(CR^9R^{10})_r$ $CO_2R^{11}$, each of $R^4$, $R^5$, $R^7$ and $R^8$ is independently hydrogen, $C_{1-4}$ alkyl, $C_{1-4}$ alkoxy, $C_{1-4}$ alkoxycarbonyl, carboxyl, halo or hydroxyl, W is a bond, k is 1, Z is $NR^{17}$, r is 1, and each of $R^9$, $R^{10}$, $R^{11}$ and $R^{17}$ is independently hydrogen or $C_{1-4}$ alkyl. Preferably, each of $R^4$, $R^5$, $R^7$ and $R^8$ is independently hydrogen or $C_{1-4}$ alkyl. More preferably, $R^4$, $R^5$, $R^7$ and $R^8$ are hydrogen. Preferably, $R^{11}$ and $R^{17}$ are hydrogen.

In still other embodiments of a compound of Formula (I), n is 1, Y is O, $R^{18}$ is hydrogen or methyl, A is $CR^4$, B is $CR^5$, D is $CR^6$, E is $CR^7$, G is $CR^8$, $R^6$ is $-W[C(O)]_kZ(CR^9R^{10})_r$ $CO_2R^{11}$, each of $R^4$, $R^5$, $R^7$ and $R^8$ is independently hydrogen, $C_{1-4}$ alkyl, $C_{1-4}$ alkoxy, $C_{1-4}$ alkoxycarbonyl, carboxyl, halo or hydroxyl, W is a bond, k is 1, Z is $NR^{17}$, r is 2, and each of $R^9$, $R^{10}$, $R^{11}$ and $R^{17}$ is independently hydrogen or $C_{1-4}$ alkyl. Preferably, each of $R^4$, $R^5$, $R^7$ and $R^8$ is independently hydrogen or $C_{1-4}$ alkyl. More preferably, $R^4$, $R^5$, $R^7$ and $R^8$ are hydrogen. Preferably, $R^{11}$ and $R^{17}$ are hydrogen.

In still other embodiments of a compound of Formula (I), n is 1, Y is O, $R^{18}$ is hydrogen or methyl, A is $CR^4$, B is $CR^5$, D is $CR^6$, E is $CR^7$, G is $CR^8$, $R^6$ is $-W[C(O)]_kZ(CR^9R^{10})_r$ $CO_2R^{11}$, each of $R^4$, $R^5$, $R^7$ and $R^8$ is independently hydrogen, $C_{1-4}$ alkyl, $C_{1-4}$ alkoxy, $C_{1-4}$ alkoxycarbonyl, carboxyl, halo or hydroxyl, W is a bond, k is 1, Z is O, r is 1, and each of $R^9$, $R^{10}$ and $R^{11}$ is independently hydrogen or $C_{1-4}$ alkyl. Preferably, each of $R^4$, $R^5$, $R^7$ and $R^8$ is independently hydrogen or $C_{1-4}$ alkyl. More preferably, $R^4$, $R^5$, $R^7$ and $R^8$ are hydrogen. Preferably, $R^{11}$ is hydrogen.

In still other embodiments of a compound of Formula (I), n is 1, Y is O, $R^{18}$ is hydrogen or methyl, A is $CR^4$, B is $CR^5$, D is $CR^6$, E is $CR^7$, G is $CR^8$, $R^6$ is $-W[C(O)]_kZ(CR^9R^{10})_r$ $CO_2R^{11}$, each of $R^4$, $R^5$, $R^7$ and $R^8$ is independently hydrogen, $C_{1-4}$ alkyl, $C_{1-4}$ alkoxy, $C_{1-4}$ alkoxycarbonyl, carboxyl, halo or hydroxyl, W is a bond, k is 1, Z is O, r is 2, and each of $R^9$, $R^{10}$ and $R^{11}$ is independently hydrogen or $C_{1-4}$ alkyl. Preferably, each of $R^4$, $R^5$, $R^7$ and $R^8$ is independently hydrogen or $C_{1-4}$ alkyl. More preferably, $R^4$, $R^5$, $R^7$ and $R^8$ are hydrogen. Preferably, $R^{11}$ is hydrogen.

In still other embodiments of a compound of Formula (I), n is 1, Y is O, $R^{18}$ is hydrogen or methyl, A is $CR^4$, B is $CR^5$, D is $CR^6$, E is $CR^7$, G is $CR^8$, $R^6$ is $-W[C(O)]_kZ(CR^9R^{10})_r$ $CO_2R^{11}$, each of $R^4$, $R^5$, $R^7$ and $R^8$ is independently hydrogen, $C_{1-4}$ alkyl, $C_{1-4}$ alkoxy, $C_{1-4}$ alkoxycarbonyl, carboxyl, halo or hydroxyl, W is O, k is 1, Z is $NR^{17}$, r is 1, and each of $R^9$, $R^{10}$, $R^{11}$ and $R^{17}$ is independently hydrogen or $C_{1-4}$ alkyl. Preferably, each of $R^4$, $R^5$, $R^7$ and $R^8$ is independently hydrogen or $C_{1-4}$ alkyl. More preferably, $R^4$, $R^5$, $R^7$ and $R^8$ are hydrogen. Preferably, $R^{11}$ and $R^{17}$ are hydrogen.

In still other embodiments of a compound of Formula (I), n is 1, Y is O, $R^{18}$ is hydrogen or methyl, A is $CR^4$, B is $CR^5$, D is $CR^6$, E is $CR^7$, G is $CR^8$, $R^6$ is $-W[C(O)]_kZ(CR^9R^{10})_r$ $CO_2R^{11}$, each of $R^4$, $R^5$, $R^7$ and $R^8$ is independently hydrogen, $C_{1-4}$ alkyl, $C_{1-4}$ alkoxy, $C_{1-4}$ alkoxycarbonyl, carboxyl, halo or hydroxyl, W is O, k is 1, Z is $NR^{17}$, r is 2, and each of $R^9$, $R^{10}$, $R^{11}$ and $R^{17}$ is independently hydrogen or $C_{1-4}$ alkyl. Preferably, each of $R^4$, $R^5$, $R^7$ and $R^8$ is independently hydrogen or $C_{1-4}$ alkyl. More preferably, $R^4$, $R^5$, $R^7$ and $R^8$ are hydrogen. Preferably, $R^{11}$ and $R^{17}$ are hydrogen.

In still other embodiments of a compound of Formula (I), n is 1, Y is O, $R^{18}$ is hydrogen or methyl, A is $CR^4$, B is $CR^5$, D is $CR^6$, E is $CR^7$, G is $CR^8$, $R^6$ is $-W[C(O)]_kZ(CR^9R^{10})_r$ $CO_2R^{11}$, each of $R^4$, $R^5$, $R^7$ and $R^8$ is independently hydrogen, $C_{1-4}$ alkyl, $C_{1-4}$ alkoxy, $C_{1-4}$ alkoxycarbonyl, carboxyl, halo or hydroxyl, W is O, k is 1, Z is O, r is 1, and each of $R^9$, $R^{10}$ and $R^{11}$ is independently hydrogen or $C_{1-4}$ alkyl. Preferably, each of $R^4$, $R^5$, $R^7$ and $R^8$ is independently hydrogen or $C_{1-4}$ alkyl. More preferably, $R^4$, $R^5$, $R^7$ and $R^8$ are hydrogen. Preferably, $R^{11}$ is hydrogen.

In still other embodiments of a compound of Formula (I), n is 1, Y is O, $R^{18}$ is hydrogen or methyl, A is $CR^4$, B is $CR^5$, D is $CR^6$, E is $CR^7$, G is $CR^8$, $R^6$ is $-W[C(O)]_kZ(CR^9R^{10})_r$ $CO_2R^{11}$, each of $R^4$, $R^5$, $R^7$ and $R^8$ is independently hydrogen, $C_{1-4}$ alkyl, $C_{1-4}$ alkoxy, $C_{1-4}$ alkoxycarbonyl, carboxyl, halo or hydroxyl, W is O, k is 1, Z is O, r is 2, and each of $R^9$, $R^{10}$ and $R^{11}$ is independently hydrogen or $C_{1-4}$ alkyl. Preferably, each of $R^4$, $R^5$, $R^7$ and $R^8$ is independently hydrogen or $C_{1-4}$ alkyl. More preferably, $R^4$, $R^5$, $R^7$ and $R^8$ are hydrogen. Preferably, $R^{11}$ is hydrogen.

In still other embodiments of a compound of Formula (I), n is 1, Y is O, $R^{18}$ is hydrogen or methyl, A is $CR^4$, B is $CR^5$, D is $CR^6$, E is $CR^7$, G is $CR^8$, $R^6$ is —$W[C(O)]_kZ(CR^9R^{10})_r$CO$_2R^{11}$, each of $R^4$, $R^5$, $R^7$ and $R^8$ is independently hydrogen, $C_{1-4}$ alkyl, $C_{1-4}$ alkoxy, $C_{1-4}$ alkoxycarbonyl, carboxyl, halo or hydroxyl, W is O, k is 1, Z is $CR^{15}R^{16}$, r is 1, and each of $R^9$, $R^{10}$, $R^{11}$, $R^{15}$ and $R^{16}$ is independently hydrogen or $C_{1-4}$ alkyl. Preferably, each of $R^4$, $R^5$, $R^7$ and $R^8$ is independently hydrogen or $C_{1-4}$ alkyl. More preferably, $R^4$, $R^5$, $R^7$ and $R^8$ are hydrogen. Preferably, $R^{11}$, $R^{15}$ and $R^{16}$ are hydrogen.

In still other embodiments of a compound of Formula (I), n is 1, Y is O, $R^{18}$ is hydrogen or methyl, A is $CR^4$, B is $CR^5$, D is $CR^6$, E is $CR^7$, G is $CR^8$, $R^6$ is —$W[C(O)]_kZ(CR^9R^{10})_r$CO$_2R^{11}$, each of $R^4$, $R^5$, $R^7$ and $R^8$ is independently hydrogen, $C_{1-4}$ alkyl, $C_{1-4}$ alkoxy, $C_{1-4}$ alkoxycarbonyl, carboxyl, halo or hydroxyl, W is O, k is 1, Z is $CR^{15}R^{16}$, r is 2, and each of $R^9$, $R^{10}$, $R^{11}$, $R^{15}$ and $R^{16}$ is independently hydrogen or $C_{1-4}$ alkyl. Preferably, each of $R^4$, $R^5$, $R^7$ and $R^8$ is independently hydrogen or $C_{1-4}$ alkyl. More preferably, $R^4$, $R^5$, $R^7$ and $R^8$ are hydrogen. Preferably, $R^{11}$, $R^{15}$ and $R^{16}$ are hydrogen.

In still other embodiments of a compound of Formula (I), n is 1, Y is O, $R^{18}$ is hydrogen or methyl, A is $CR^4$, B is $CR^5$, D is $CR^6$, E is $CR^7$, G is $CR^8$, $R^6$ is —$W[C(O)]_kZ(CR^9R^{10})_r$CO$_2R^{11}$, each of $R^4$, $R^5$, $R^7$ and $R^8$ is independently hydrogen, $C_{1-4}$ alkyl, $C_{1-4}$ alkoxy, $C_{1-4}$ alkoxycarbonyl, carboxyl, halo or hydroxyl, W is $NR^{14}$, k is 1, Z is $NR^{17}$, r is 1 and each of $R^9$, $R^{10}$, $R^{11}$, $R^{14}$ and $R^{17}$ is independently hydrogen or $C_{1-4}$ alkyl. Preferably, each of $R^4$, $R^5$, $R^7$ and $R^8$ is independently hydrogen or $C_{1-4}$ alkyl. More preferably, $R^4$, $R^5$, $R^7$ and $R^8$ are hydrogen. Preferably, $R^{11}$, $R^{14}$ and $R^{17}$ are hydrogen.

In still other embodiments of a compound of Formula (I), n is 1, Y is O, $R^{18}$ is hydrogen or methyl, A is $CR^4$, B is $CR^5$, D is $CR^6$, E is $CR^7$, G is $CR^8$, $R^6$ is —$W[C(O)]_kZ(CR^9R^{10})_r$CO$_2R^{11}$, each of $R^4$, $R^5$, $R^7$ and $R^8$ is independently hydrogen, $C_{1-4}$ alkyl, $C_{1-4}$ alkoxy, $C_{1-4}$ alkoxycarbonyl, carboxyl, halo or hydroxyl, W is $NR^{14}$, k is 1, Z is $NR^{17}$, r is 2 and each of $R^9$, $R^{10}$, $R^{11}$, $R^{14}$ and $R^{17}$ is independently hydrogen or $C_{1-4}$ alkyl. Preferably, each of $R^4$, $R^5$, $R^7$ and $R^8$ is independently hydrogen or $C_{1-4}$ alkyl. More preferably, $R^4$, $R^5$, $R^7$ and $R^8$ are hydrogen. Preferably, $R^{11}$, $R^{14}$ and $R^{17}$ are hydrogen.

In still other embodiments of a compound of Formula (I), n is 1, Y is O, $R^{18}$ is hydrogen or methyl, A is $CR^4$, B is $CR^5$, D is $CR^6$, E is $CR^7$, G is $CR^8$, $R^6$ is —$W[C(O)]_kZ(CR^9R^{10})_r$CO$_2R^{11}$, each of $R^4$, $R^5$, $R^7$ and $R^8$ is independently hydrogen, $C_{1-4}$ alkyl, $C_{1-4}$ alkoxy, $C_{1-4}$ alkoxycarbonyl, carboxyl, halo or hydroxyl, W is $NR^{14}$, k is 1, Z is O, r is 1, and each of $R^9$, $R^{10}$, $R^{11}$ and $R^{14}$ is independently hydrogen or $C_{1-4}$ alkyl. Preferably, each of $R^4$, $R^5$, $R^7$ and $R^8$ is independently hydrogen or $C_{1-4}$ alkyl. More preferably, $R^4$, $R^5$, $R^7$ and $R^8$ are hydrogen. Preferably, each of $R^{11}$ and $R^{14}$ are hydrogen.

In still other embodiments of a compound of Formula (I), n is 1, Y is O, $R^{18}$ is hydrogen or methyl, A is $CR^4$, B is $CR^5$, D is $CR^6$, E is $CR^7$, G is $CR^8$, $R^6$ is —$W[C(O)]_kZ(CR^9R^{10})_r$CO$_2R^{11}$, each of $R^4$, $R^5$, $R^7$ and $R^8$ is independently hydrogen, $C_{1-4}$ alkyl, $C_{1-4}$ alkoxy, $C_{1-4}$ alkoxycarbonyl, carboxyl, halo or hydroxyl, W is $NR^4$, k is 1, Z is O, r is 2, and each of $R^9$, $R^{10}$, $R^{11}$ and $R^{14}$ is independently hydrogen or $C_{1-4}$ alkyl. Preferably, each of $R^4$, $R^5$, $R^7$ and $R^8$ is independently hydrogen or $C_{1-4}$ alkyl. More preferably, $R^4$, $R^5$, $R^7$ and $R^8$ are hydrogen. Preferably, each of $R^{11}$ and $R^{14}$ are hydrogen.

In still other embodiments of a compound of Formula (I), n is 1, Y is O, $R^{18}$ is hydrogen or methyl, A is $CR^4$, B is $CR^5$, D is $CR^6$, E is $CR^7$, G is $CR^8$, $R^6$ is —$W[C(O)]_kZ(CR^9R^{10})_r$CO$_2R^{11}$, each of $R^4$, $R^5$, $R^7$ and $R^8$ is independently hydrogen, $C_{1-4}$ alkyl, $C_{1-4}$ alkoxy, $C_{1-4}$ alkoxycarbonyl, carboxyl, halo or hydroxyl, W is $NR^{14}$, k is 1, Z is $CR^{15}R^{16}$, r is 1, and each of $R^9$, $R^{10}$, $R^{11}$, $R^{14}$, $R^{15}$ and $R^{16}$ is independently hydrogen or $C_{1-4}$ alkyl. Preferably, each of $R^4$, $R^5$, $R^7$ and $R^8$ is independently hydrogen or $C_{1-4}$ alkyl. More preferably, $R^4$, $R^5$, $R^7$ and $R^8$ are hydrogen. Preferably, $R^{11}$, $R^{14}$, $R^{15}$ and $R^{16}$ are hydrogen.

In still other embodiments of a compound of Formula (I), n is 1, Y is O, $R^{18}$ is hydrogen or methyl, A is $CR^4$, B is $CR^5$, D is $CR^6$, E is $CR^7$, G is $CR^8$, $R^6$ is —$W[C(O)]_kZ(CR^9R^{10})_r$CO$_2R^{11}$, each of $R^5$, $R^5$, $R^7$ and $R^8$ is independently hydrogen, $C_{1-4}$ alkyl, $C_{1-4}$ alkoxy, $C_{1-4}$ alkoxycarbonyl, carboxyl, halo or hydroxyl, W is $NR^{14}$, k is 1, Z is $CR^{15}R^{16}$, r is 2, and each of $R^9$, $R^{10}$, $R^{11}$, $R^{14}$, $R^{15}$ and $R^{16}$ is independently hydrogen or $C_{1-4}$ alkyl. Preferably, each of $R^4$, $R^5$, $R^7$ and $R^8$ is independently hydrogen or $C_{1-4}$ alkyl. More preferably, $R^4$, $R^5$, $R^7$ and $R^8$ are hydrogen. Preferably, $R^{11}$, $R^{14}$, $R^{15}$ and $R^{16}$ are hydrogen.

Compounds of structural Formula (I) may be substrates for intestinal anion transporters such as the sodium-dependent multivitamin transporter ("SMVT") and members of the proton-dependent monocarboxylate transporter ("MCT") family. The SMVT transporter typically mediates the intestinal absorption of the water-soluble vitamins pantothenate and biotin whereas natural substrates for intestinally expressed monocarboxylate transporters include lactate and pyruvate (Wang et al., *J. Biol. Chem.* 1999, 274, 14875–14883; Halestrap et al., *Biochem. J.* 1999, 343, 281–299). The intestinal permeability of certain monocarboxylate drugs (e.g., carindacillin, atorvastatin, etc.) may be mediated via interaction with MCTs. Monocarboxylate transporter 1 ("MCT1") expression extends from the upper regions of the mammalian gastrointestinal tract through the large intestine, where it plays a role in absorption of short-chain fatty acids (e.g., butyrate) produced by colonic bacteria. Molecules transported by such colonically expressed proteins are candidates for formulation in sustained oral delivery systems, where controlled release of the drug during its prolonged residence in the colon leads to sustained systemic drug levels relative to conventional immediate release formulations. Similarly, compounds that passively diffuse across the colonic mucosa may be administered via oral sustained release formulations.

Methods for determining whether compounds may serve as substrates for the SMVT transporter are disclosed in Example 3 herein (see Section 5).

4.3 Synthesis

Compounds disclosed herein may be obtained via the synthetic methods illustrated in Schemes 1–7. Compounds of Formula (I) where n is 0, Y is a bond or $CR^1R^2$, W is a bond, k is 1, Z is O or $NR^{17}$ and $R^{11}$ is hydrogen, i.e., compound (7), are prepared according to methods illustrated in Scheme 1. The aromatic or heteroaromatic carboxylic acid compound (2) is first converted into a reactive acylating agent (3), by treatment with a phosgene equivalent, thionyl halide or related activating agent. Reaction with propofol in the presence of base, and optionally a catalyst such as DMAP, affords bis-ester (4). Removal of the carboxylate protecting group, conversion to a reactive acylating agent by treatment with an appropriate coupling reagent, followed by addition of protected amino acid or hydroxyl acid (5) generates compound (6). Finally, removal of the carboxylate protecting group affords the desired compound (7).

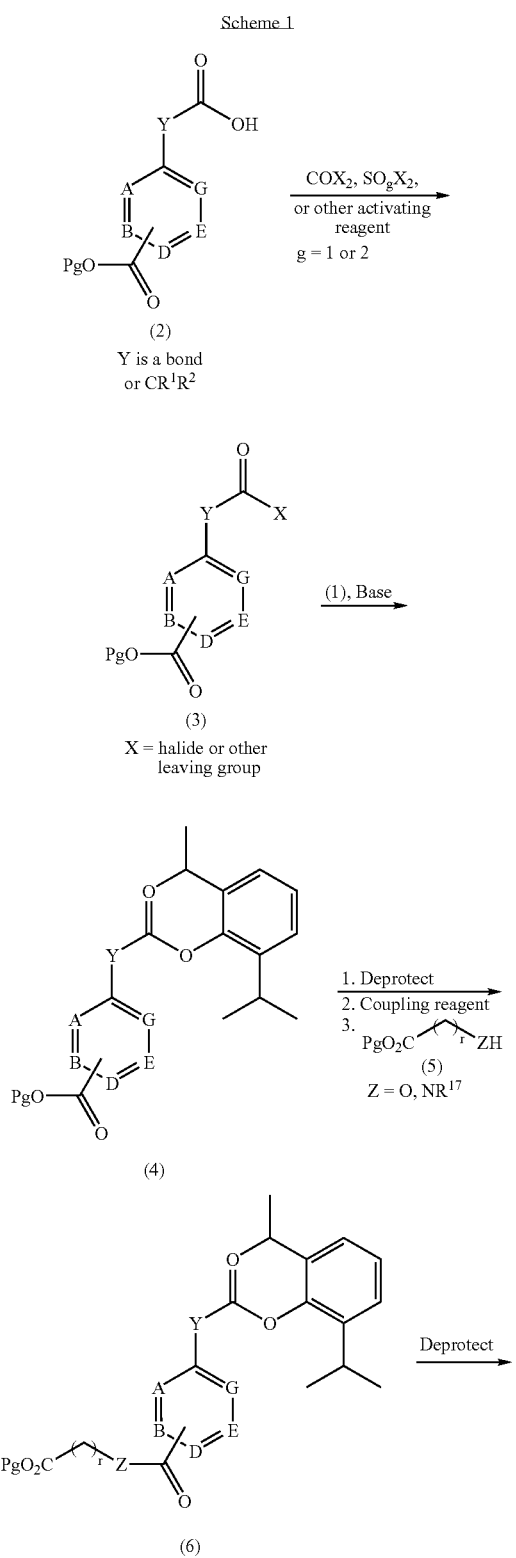

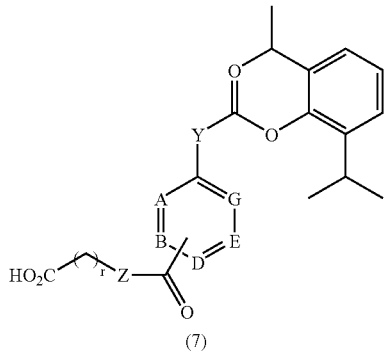

Alternatively, ortho-disubstituted aromatic or heteroaromatic derivatives related to compound (7), i.e., compound (10), can be expediently prepared starting with anhydride compound (8), as illustrated in Scheme 2.

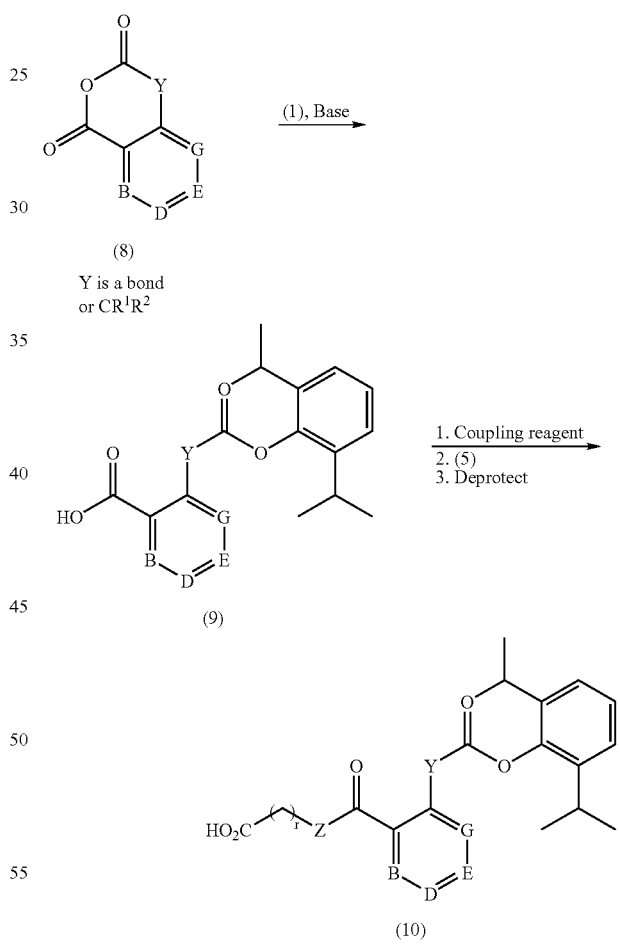

Compounds of Formula (I) where n is 0, Y is a bond or $CR^1R^2$, W is O or $NR^{14}$, k is 1, Z is $CR^{15}R^{16}$, O or $NR^{17}$ and $R^{11}$ is hydrogen, i.e., compound (16), are prepared according to methods illustrated in Scheme 3. The aromatic or heteroaromatic carboxylic acid compound (11) is first converted into a reactive acylating agent (12), by treatment with a phosgene equivalent, thionyl halide or related activating agent. Reaction with propofol in the presence of base, and optionally a catalyst such as DMAP, affords ester (13).

Removal of the protecting group from either the oxygen or nitrogen atom in (13), followed by treatment with acylating agent (14) or (15) affords, after deprotection of the carboxylate moiety, compound (16).

Compounds of Formula (I) where n is 0, Y is O or $NR^3$, W is a bond, k is 1, Z is O or $NR^{17}$ and $R^{11}$ is hydrogen, i.e., compound (20), are prepared according to methods illustrated in Scheme 4. The phenolic or anilino compound (17) is reacted with a phosgene equivalent to give respectively the chloroformate or amidoyl chloride species (18). Displacement of the chloro group by treatment with propofol in the presence of base, and optionally a catalyst like DMAP, affords carbonate or carbamate (19). Alternatively, compound (19) can be elaborated directly from compound (17) by reaction with the propofol chloroformate derivative (31). Coupling of the carboxyalkyl moiety (5) proceeds as previously described to afford compound (20).

Scheme 3

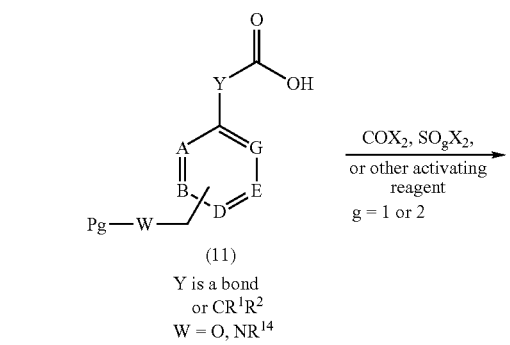
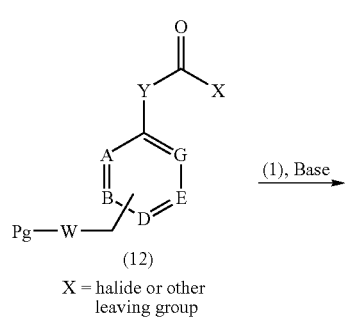
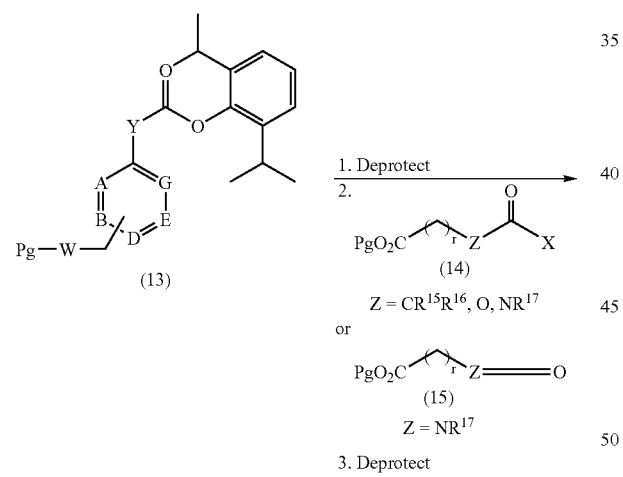

Scheme 4

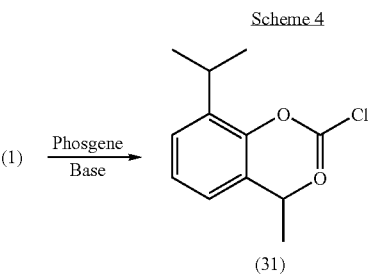
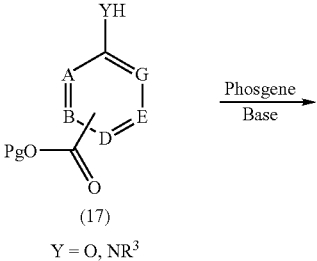
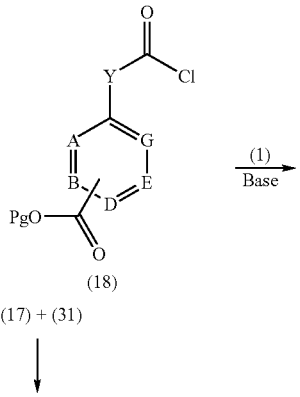
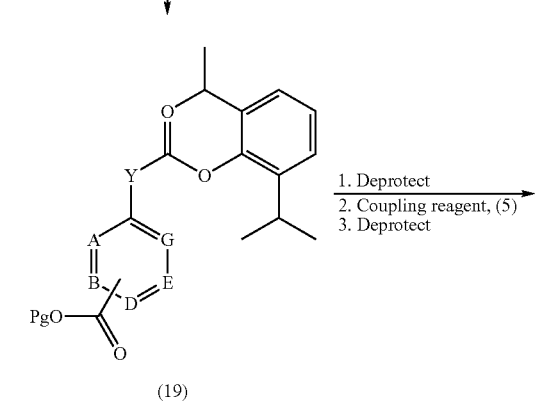

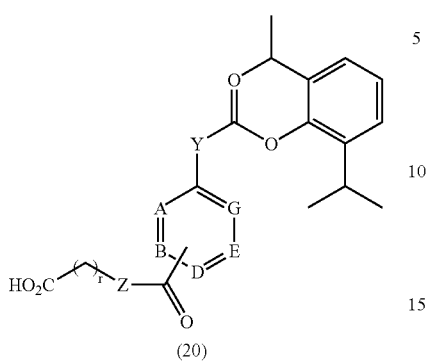

(20)

Compounds of Formula (I) where n is 0, Y is O or $NR^3$, W is O or $NR^{14}$, k is 1, Z is $CR^{15}R^{16}$, O or $NR^{17}$ and $R^{11}$ is hydrogen, i.e., compound (24), are prepared in an analogous fashion from compound (21), as illustrated in Scheme 5.

Scheme 5

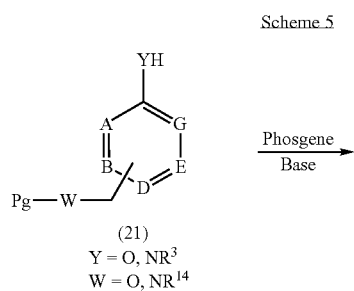

(21)
Y = O, $NR^3$
W = O, $NR^{14}$

(21) + (31)

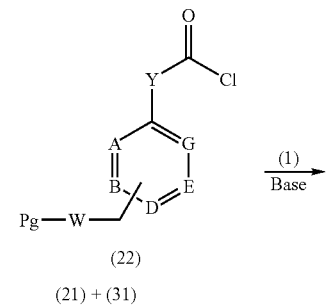

(22)

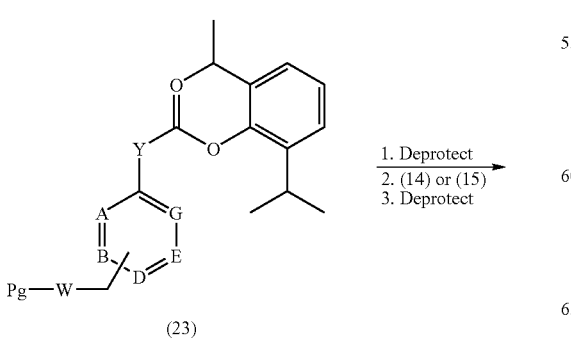

(23)

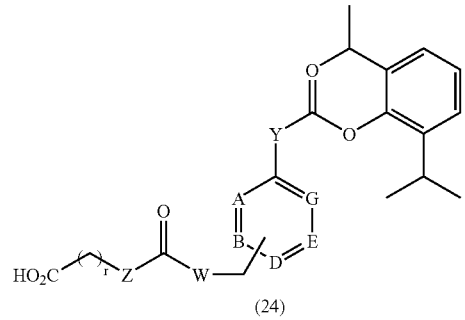

(24)

Compounds of Formula (I) where n is 1, Y is a bond or $CR^1R^2$, W is a bond, k is 1, Z is O or $NR^{17}$ and $R^{11}$ is hydrogen, i.e., compound (27), are prepared according to methods illustrated in Scheme 6. The acyloxyalkyl ether (26) is prepared from aromatic or heteroaromatic carboxylic acid compound (2), either by sequential halide displacements of compound (32) in the presence of a base or metal promoter agent (typically a soluble $Ag^+$ or $Hg^{2+}$ salt), or by reaction with the haloalkyl (or thioalkyl) propofol ether (33). If $X_2$ in (25) is —SR (e.g., thiomethyl), activation by treatment with sulfuryl chloride or similar halogenating agents precedes displacement by propofol to generate compound (26). Coupling of the carboxyalkyl moiety (5) proceeds as previously described to afford compound (27).

Scheme 6

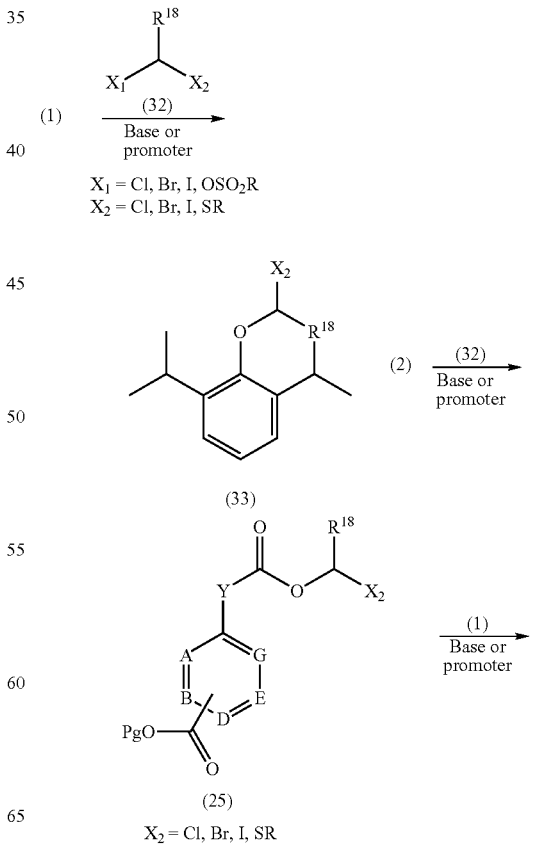

-continued (2) + (33)

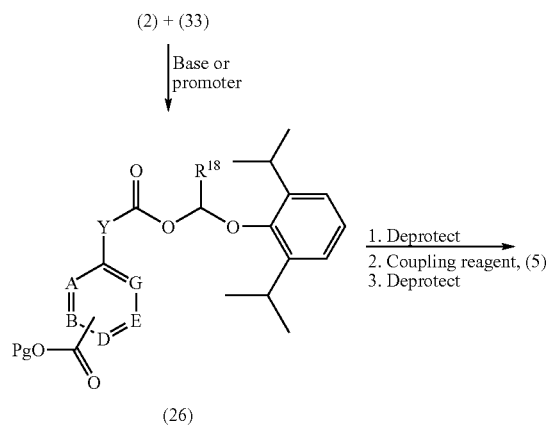

(26)

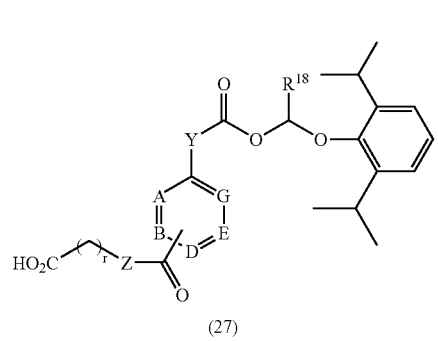

(27)

Compounds of Formula (I) where n is 1, Y is a bond or $CR^1R^2$, W is O or $NR^{14}$, k is 1, Z is $CR^{15}R^{16}$, O or $NR^{17}$ and $R^{11}$ is hydrogen, i.e., compound (30), are prepared according to methods illustrated in Scheme 7. The acyloxyalkyl ether (29) is prepared from (11), either by sequential halide displacements of compound (32) under conditions previously described (i.e., in the presence of base or with a metal salt promoter), or by reaction with the haloalkyl (or thioalkyl) propofol ether (33). Removal of the protecting group from either the oxygen or nitrogen atom in (29), followed by treatment with acylating agent (14) or (15) affords, after deprotection of the carboxylate moiety, compound (30).

Scheme 7

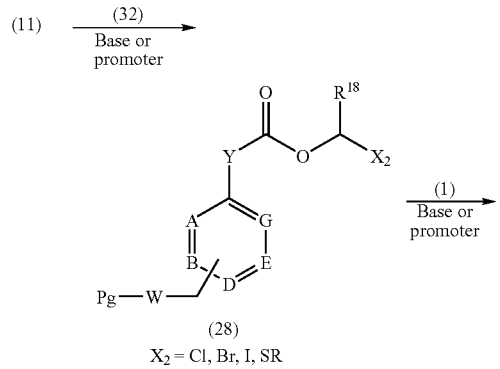

$X_2$ = Cl, Br, I, SR

-continued

(11) + (33)

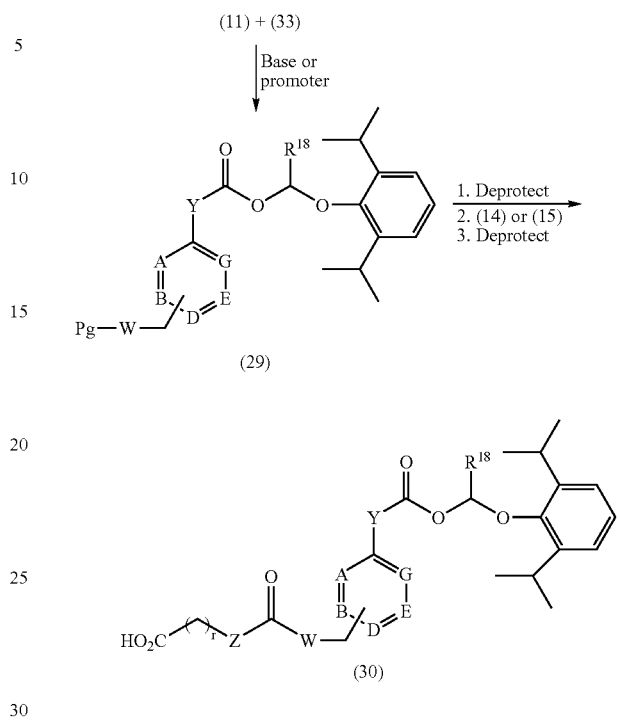

5.4 Therapeutic/Prophylactic Uses of the Compounds and Modes of Administration The compounds described herein, may be used to treat and/or prevent migraine in patients. The methods comprise administering to a patient a therapeutically effective amount of a compound to treat or prevent migraine. In the therapeutic methods disclosed herein, a therapeutically effective amount of the compound is administered to a patient suffering from a migraine headache. In the prophylactic methods disclosed herein a therapeutically effective amount of the compound is administered to a patient at risk of developing a migraine.

In some embodiments, compounds disclosed herein are administered orally to treat or prevent migraine. However, in other embodiments, compounds disclosed herein are administered parenterally (e.g., via inhalation or injection). In some embodiments, compounds are administered in amounts of between about 10 mg to about 2 g to treat or prevent migraine.

Compounds disclosed herein may also be used as antiemetics and can be administered to patients at risk of vomiting or who are nauseous. For example, compounds disclosed herein may be administered to patients that are being concurrently treated with various chemotherapy agents and/or surgical procedures, which induce nausea. Accordingly, methods for treating and preventing nausea and vomiting are provided. Typically, a therapeutically effective amount of a compound disclosed herein is administered to a patient to treat or prevent nausea and vomiting.

In some embodiments, compounds are administered orally to treat or prevent nausea or vomiting. However, in other embodiments, compounds are administered parenterally (e.g., via inhalation or injection to treat or prevent nausea or vomiting. In some embodiments, compounds are administered in amounts of between about 10 mg to about 2 g to treat or prevent nausea or vomiting.

Compounds may also be used as hypnotic agents to induce and/or maintain general anesthesia and/or as a sedative. Typically, a therapeutically effective amount of compound is administered to a patient to induce hypnosis.

In some embodiments, compounds are administered intravenously when used as a general anesthetic. In other embodiments, compounds are administered by inhalation. Compounds may be formulated by the same methods used to formulate propofol, which are well known in the art. In some embodiments, compounds are formulated as an aqueous solution, which contains significantly less emulsifiers or solubilizers than used in aqueous formulations of propofol.

In some embodiments, compounds are administered orally in amounts of about 10 mg to 2 g daily when used as a sedative (e.g., for the treatment of anxiety conditions). However, in other embodiments, compound may also be administered by inhalation, intravenously or intramuscularly when used as a sedative.

Compounds disclosed herein may be administered in similar amounts and in the same schedule as described in the art for propofol. In some embodiments, dosage levels of compounds for producing general anesthesia, maintaining anesthesia and producing a sedative effect are as described in the art for propofol.

Compounds may also be used to inhibit oxidation in biological materials. The methods involve contacting the biological material with an effective amount of the compound. In therapeutic methods disclosed herein, a therapeutically effective amount of the compound is administered to a patient suffering from a pathological condition treated by inhibition of oxidation. In prophylactic methods disclosed herein a therapeutically effective amount of the compound is administered to a patient at risk of developing a disease as a result of exposure to oxidative stress. Compounds disclosed herein may find particular use in preventing or treating oxidation in disorders of the central nervous system that involve an inflammatory component.

Compounds disclosed herein may be used to treat or prevent neurodegenerative conditions of the nervous system, which include, but are not limited to, Friedrich's disease, Parkinson's disease, Alzheimer's disease, Huntington's disease, amyotrophic lateral sclerosis (ALS), multiple sclerosis (MS) and Pick disease. In some embodiments, a therapeutically effective amount of a compound (e.g., between about 10 mg to about 2 g daily) is orally administered to treat or prevent chronic neurodegenerative diseases.

Compounds disclosed herein may also be used to treat trauma to the central nervous system such as, for example, skull fracture and its resulting edema, concussion, contusion, brain hemorrhages, shearing lesions, subdural and epidural hematoma, and spinal cord injury (e.g., mechanical injury due to compression or flexion of the spinal cord). In some embodiments, a compound is parenterally administered by intravenous injection or injection directly into the central nervous system (i.e., intrathecally ("IT") or into the brain) to treat or prevent traumatic conditions of the central nervous system. In other embodiments, a therapeutically effective amount of a compound (e.g., between about 25 mg to about 500 mg IV or IM and between about 5 mg to about 100 mg IT) are administered to treat or prevent traumatic conditions of the central nervous system.

Compounds may also be used as anti-convulsives to treat or prevent seizures (e.g., epileptic seizures). Methods for treating or preventing convulsions, which comprise administering a therapeutically effective amount of a compound disclosed herein to a patient in need of such treatment are provided. In some embodiments, compounds are administered orally to treat or prevent convulsions. In other embodiments, compounds are parenterally administered to treat or prevent convulsions. In other embodiments, compounds are administered in amounts of between about 10 mg to about 2 g daily to treat or prevent convulsions.

When used to treat or prevent the above disease or disorders compounds and/or pharmaceutical compositions thereof may be administered or applied singly, in combination with other agents. Compounds and/or pharmaceutical compositions thereof may also be administered or applied singly, in combination with other pharmaceutically active agents, including other compounds disclosed herein.

Methods of treatment and prophylaxis by administration to a patient of a therapeutically effective amount of a compound or pharmaceutical composition thereof are provided herein. The patient may be an animal, is more preferably a mammal, and most preferably, a human.

The present compounds and/or pharmaceutical compositions thereof, are preferably administered orally. Compounds and/or pharmaceutical compositions thereof may also be administered by any other convenient route, for example, by infusion or bolus injection, by absorption through epithelial or mucocutaneous linings (e.g., oral mucosa, rectal and intestinal mucosa, etc.). Administration can be systemic or local. Various delivery systems are known, (e.g., encapsulation in liposomes, microparticles, microcapsules, capsules, etc.) that can be used to administer compounds and/or pharmaceutical composition thereof. Methods of administration include, but are not limited to, intradermal, intramuscular, intraperitoneal, intravenous, subcutaneous, intranasal, epidural, oral, sublingual, intranasal, intracerebral, intravaginal, transdermal, rectally, by inhalation, or topically, particularly to the ears, nose, eyes, or skin.

In specific embodiments, it may be desirable to administer one or more compounds and/or pharmaceutical composition thereof locally to the area in need of treatment. This may be achieved, for example, and not by way of limitation, by local infusion during surgery, topical application, e.g., in conjunction with a wound dressing after surgery, by injection, by means of a catheter, by means of a suppository, or by means of an implant, said implant being of a porous, non-porous, or gelatinous material, including membranes, such as sialastic membranes, or fibers.

In certain embodiments, it may be desirable to introduce one or more compounds and/or pharmaceutical compositions thereof into the central nervous system by any suitable route, including intraventricular, intrathecal and epidural injection. Intraventricular injection may be facilitated by an intraventricular catheter, for example, attached to a reservoir, such as an Ommaya reservoir.

In some embodiments, compounds and/or pharmaceutical compositions thereof can be delivered via sustained release systems, preferably, oral sustained release systems. In some embodiments, a pump may be used (see Langer, supra; Sefton, 1987, *CRC Crit Ref Biomed Eng.* 14:201; Saudek et al., 1989, *N. Engl. J. Med.* 321:574).

In other embodiments, polymeric materials can be used (see "Medical Applications of Controlled Release," Langer and Wise (eds.), CRC Pres., Boca Raton, Fla. (1974); "Controlled Drug Bioavailability," Drug Product Design and Performance, Smolen and Ball (eds.), Wiley, New York (1984); Langer et al., 1983, *J Macromol. Sci. Rev. Macromol Chem.* 23:61; see also Levy et al., 1985, *Science* 228: 190; During et al., 1989, *Ann. Neurol.* 25:351; Howard et al., 1989, *J. Neurosurg.* 71:105). In still other embodiments, polymeric materials are used for oral sustained release delivery. Such polymers include, for example, sodium carboxymethylcellulose, hydroxypropylcellulose, hydroxypropylmethylcellulose and hydroxyethylcellulose. Other cellulose ethers have been described (Alderman, *Int. J. Pharm. Tech. & Prod. Mfr.* 1984, 5(3) 1–9). Factors affecting drug release are well known to the skilled artisan and have been described in the art (Bamba et al., *Int. J. Pharm.* 1979, 2, 307).

In other embodiments, enteric-coated preparations are used for oral sustained release administration. Coating materials include, for example, polymers with pH-dependent solubility (i.e., pH-controlled release), polymers with slow or pH-dependent rate of swelling, dissolution or erosion (i.e., time-controlled release), polymers that are degraded by enzymes (i.e., enzyme-controlled release) and polymers that form firm layers that are destroyed by an increase in pressure (i.e., pressure-controlled release).

In still other embodiments, osmotic delivery systems are used for oral sustained release administration (Verma et al., *Drug Dev. Ind. Pharm.* 2000, 26:695–708). In some embodiments, OROS™ osmotic devices are used for oral sustained release delivery devices (Theeuwes et al., U.S. Pat. No. 3,845,770; Theeuwes et al., U.S. Pat. No. 3,916,899).

For administration by inhalation, compounds may be conveniently delivered to the lung by a number of different devices. For example, a Metered Dose Inhaler ("MDI") which utilizes canisters that contain a suitable low boiling propellant, e.g., dichlorodifluoromethane, trichlorofluoromethane, dichlorotetrafluoroethane, carbon dioxide or other suitable gas may be used to deliver compounds disclosed herein directly to the lung.

Alternatively, a Dry Powder Inhaler ("DPI") device may be used to administer compounds to the lung (See, e.g., Raleigh et al., *Proc. Amer. Assoc. Cancer Research Annual Meeting*, 1999, 40, 397). DPI devices typically use a mechanism such as a burst of gas to create a cloud of dry powder inside a container, which may then be inhaled by the patient. A popular variation is the multiple dose DPI ("MDDPI") system, which allows for the delivery of more than one therapeutic dose. For example, capsules and cartridges of gelatin for use in an inhaler or insufflator may be formulated containing a powder mix of a compound and a suitable powder base such as lactose or starch for these systems.

Another type of device that may be used to deliver compounds to the lung is a liquid spray device supplied, for example, by Aradigm Corporation, Hayward, Calif. Liquid spray systems use extremely small nozzle holes to aerosolize liquid drug formulations that may then be directly inhaled into the lung.

In some embodiments, a nebulizer device is used to deliver a compound disclosed herein to the lung. Nebulizers create aerosols from liquid drug formulations by using, for example, ultrasonic energy to form fine particles that may be readily inhaled (see e.g., Verschoyle et al., *British J. Cancer*, 1999, 80, Suppl. 2, 96). Examples of nebulizers include devices supplied by Batelle Pulmonary Therapeutics (Columbus, Ohio) (See, Armer et al., U.S. Pat. No. 5,954,047; van der Linden et al., U.S. Pat. No. 5,950,619; van der Linden et al., U.S. Pat. No. 5,970,974).

In still other embodiments, an electrohydrodynamic ("EHD") aerosol device is used to deliver a compound to the lung. EHD aerosol devices use electrical energy to aerosolize liquid drug solutions or suspensions (see e.g., Noakes et al., U.S. Pat. No. 4,765,539; Coffee, U.S. Pat. No. 4,962,885; Coffee, International Publication No. WO 94/12285; Coffee, International Publication No., WO 94/14543; Coffee, International Publication No. WO 95/26234, Coffee, International Publication No. WO 95/26235, Coffee, International Publication No. WO 95/32807). Electrochemical properties of a compound may be important parameters to optimize when delivering this compound to the lung with an EHD aerosol device; such optimization is routinely performed by one of skill in the art. EHD aerosol devices may more efficiently deliver compounds to the lung than existing pulmonary delivery technologies. Other methods of intra-pulmonary delivery of compounds are known to the skilled artisan and are within the scope of the present disclosure.

The compounds and/or pharmaceutical compositions thereof preferably, provide therapeutic or prophylactic levels of propofol upon in vivo administration to a patient. While not wishing to bound by theory, the promoiety or promoieties of the compounds may be cleaved either chemically and/or enzymatically. One or more enzymes present in the stomach, intestinal lumen, intestinal tissue, blood, liver, brain or any other suitable tissue of a mammal may enzymatically cleave the promoiety or promoieties of the compounds disclosed herein. The mechanism of cleavage is not important.

While not wishing to bound by theory, the promoiety or promoieties of the compounds disclosed herein may be cleaved prior to absorption by the gastrointestinal tract (e.g., within the stomach or intestinal lumen) and/or after absorption by the gastrointestinal tract (e.g., in intestinal tissue, blood, liver or other suitable tissue of a mammal). Propofol may remain conjugated to a promoiety during transit across the intestinal mucosal barrier to provide protection from presystemic metabolism. In some embodiments, compounds are essentially not metabolized to propofol within enterocytes, but are metabolized to the parent drug within the systemic circulation. Cleavage of the promoiety or promoieties of the compounds after absorption by the gastrointestinal tract, may allow these prodrugs to be absorbed into the systemic circulation either by active transport, passive diffusion or by a mixture of both active and passive processes. In some embodiments, compounds are actively absorbed through interaction with anion transporters like SMVT or MCT's.

Cleavage of the promoiety or promoieties of compounds after absorption by the gastrointestinal tract, may allow these prodrugs to be absorbed into the systemic circulation from the large intestine. In some embodiments, the compounds and/or pharmaceutical compositions thereof are administered as sustained release systems. In other embodiments, the compounds and/or pharmaceutical compositions thereof are delivered by oral sustained release administration. Preferably, in this embodiment, the compounds and/or pharmaceutical compositions are administered twice per day (more preferably, once per day).

5.5 Pharmaceutical Compositions

The present pharmaceutical compositions contain a therapeutically effective amount of one or more compounds, preferably in purified form, together with a suitable amount of a pharmaceutically acceptable vehicle, to provide the form for proper administration to a patient. When administered to a patient, the compounds and pharmaceutically acceptable vehicles are preferably sterile. Water is a preferred vehicle when a compound is administered intravenously. Saline solutions and aqueous dextrose and glycerol solutions can also be employed as liquid vehicles, particularly for injectable solutions. Suitable pharmaceutical vehicles also include excipients such as starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. The present pharmaceutical compositions, if desired, can also contain minor amounts of wetting or emulsifying agents, or pH buffering agents. In addition, auxiliary, stabilizing, thickening, lubricating and coloring agents may be used.

Pharmaceutical compositions comprising a compound disclosed herein may be manufactured by means of conventional mixing, dissolving, granulating, dragee-making, levigating, emulsifying, encapsulating, entrapping or lyophilizing processes. Pharmaceutical compositions may be formulated in conventional manner using one or more physiologically acceptable carriers, diluents, excipients or auxiliaries, which facilitate processing of compounds into preparations which can be used pharmaceutically. Proper formulation is dependent upon the route of administration chosen.

The present compositions can take the form of solutions, suspensions, emulsion, tablets, pills, pellets, capsules, capsules containing liquids, powders, sustained-release formulations, suppositories, emulsions, aerosols, sprays, suspensions, or any other form suitable for use. In some embodiments, the pharmaceutically acceptable vehicle is a capsule (see e.g., Grosswald et al., U.S. Pat. No. 5,698,155). Other examples of suitable pharmaceutical vehicles have been described in the art (see Remington's Pharmaceutical Sciences, Philadelphia College of Pharmacy and Science, 19th Edition, 1995). In other embodiment, pharmaceutical compositions are formulated for oral delivery.

Pharmaceutical compositions for oral delivery may be in the form of tablets, lozenges, aqueous or oily suspensions, granules, powders, emulsions, capsules, syrups, or elixirs, for example. Orally administered pharmaceutical compositions may contain one or more optional agents, for example, sweetening agents such as fructose, aspartame or saccharin, flavoring agents such as peppermint, oil of wintergreen, or cherry coloring agents and preserving agents, to provide a pharmaceutically palatable preparation. Moreover, where in tablet or pill form, the pharmaceutical compositions may be coated to delay disintegration and absorption in the gastrointestinal tract, thereby providing a sustained action over an extended period of time. Selectively permeable membranes surrounding an osmotically active driving compound are also suitable for orally administered compounds and pharmaceutical compositions. In these later platforms, fluid from the environment surrounding the capsule is imbibed by the driving compound, which swells to displace the agent or agent composition through an aperture. These delivery platforms can provide an essentially zero order delivery profile as opposed to the spiked profiles of immediate release formulations. A time delay material such as glycerol monostearate or glycerol stearate may also be used. Oral compositions can include standard vehicles such as mannitol, lactose, starch, magnesium stearate, sodium saccharine, cellulose, magnesium carbonate, etc. Such vehicles are preferably of pharmaceutical grade.

For oral liquid preparations such as, for example, suspensions, elixirs and solutions, suitable carriers, excipients or diluents include water, saline, alkyleneglycols (e.g., propylene glycol), polyalkylene glycols (e.g., polyethylene glycol) oils, alcohols, slightly acidic buffers between pH 4 and pH 6 (e.g., acetate, citrate, ascorbate at between about 5 mM to about 50 mM), etc. Additionally, flavoring agents, preservatives, coloring agents, bile salts, acylcarnitines and the like may be added.

Compounds may also be formulated in rectal or vaginal pharmaceutical compositions such as suppositories or retention enemas, e.g., containing conventional suppository bases such as cocoa butter or other glycerides.

In addition to the formulations described previously, compounds may also be formulated as a depot preparation. Such long acting formulations may be administered by implantation (for example, subcutaneously or intramuscularly) or by intramuscular injection. Thus, for example, compounds may be formulated with suitable polymeric or hydrophobic materials (for example, as an emulsion in an acceptable oil) or ion exchange resins, or as sparingly soluble derivatives, for example, as a sparingly soluble salt.

When a compound is acidic, it may be included in any of the above-described formulations as the free acid, a pharmaceutically acceptable salt, a solvate or hydrate. Pharmaceutically acceptable salts substantially retain the activity of the free acid, may be prepared by reaction with bases and tend to be more soluble in aqueous and other protic solvents than the corresponding free acid form.

Liquid drug formulations suitable for use with nebulizers and liquid spray devices and EHD aerosol devices will typically include a compound with a pharmaceutically acceptable carrier. The pharmaceutically acceptable carrier may be a liquid such as alcohol, water, polyethylene glycol or perfluorocarbon. Optionally, another material may be added to alter the aerosol properties of the solution or suspension of compounds disclosed herein. Preferably, this material is liquid such as an alcohol, glycol, polyglycol or fatty acid. Other methods of formulating liquid drug solutions or suspension suitable for use in aerosol devices are known to those of skill in the art (see, e.g., Biesalski, U.S. Pat. No. 5,112,598; Biesalski, U.S. Pat. No. 5,556,611).

5.6 Combination Therapy

In certain embodiments, the compounds disclosed herein can be used in combination therapy with at least one other therapeutic agent. The compound and the therapeutic agent can act additively or, more preferably, synergistically. In some embodiments, a pharmaceutical composition comprising a compound disclosed herein is administered concurrently with the administration of another therapeutic agent, which can be part of the same pharmaceutical composition a or a different pharmaceutical composition. In other embodiments, a pharmaceutical composition comprising a compound disclosed herein is administered prior or subsequent to administration of another therapeutic agent.

6. EXAMPLES

The following examples, further define the disclosure and describe in detail preparation of compounds, pharmaceutical compositions thereof and assays for using compounds and pharmaceutical compositions. It will be apparent to those skilled in the art that many modifications, both to materials and methods, may be practiced without departing from the scope of the invention.

In the examples below, the following abbreviations have the following meanings. If an abbreviation is not defined, it has its generally accepted meaning.

Atm=atmosphere
Boc=tert-butyloxycarbonyl
Bzl=benzyl

Cbz=carbobenzyloxy
DCC=dicyclohexylcarbodiimide
DMAP=4-N,N-dimethylaminopyridine
DMEM=Dulbecco's minimun eagle medium
DMF=N,N-dimethylformamide
DMSO=dimethylsulfoxide
Fmoc=9-fluorenylmethyloxycarbonyl
g=gram
h=hour
HBSS=Hank's buffered saline solution
L=liter
LC/MS=liquid chromatography/mass spectroscopy
M=molar
min=minute
mL=milliliter
mmol=millimoles
NHS=N-hydroxysuccinimide
PBS=phosphate buffered saline
THF=tetrahydrofuran
TFA=trifluoroacetic acid
TMS=trimethylsilyl
μL=microliter
μM=micromolar
v/v=volume to volume Example 1

3-{[2-[2,6-Bis(isopropyl)phenoxycarbonyl]-benzoyl]amino}-propanoic acid (101)

STEP A: 2-[2,6-Bis(isopropyl)phenoxycarbonyl]-benzoic acid (102)

To a mixture of phthalic anhydride (0.84 g, 5.6 mmol) and propofol (1 g, 5.6 mmol) was added triethylamine (0.65 g, 6.4 mmol) and a catalytic amount of DMAP. The reaction mixture was brought to 90° C., stirred for 14 h, cooled to room temperature and diluted with ethyl ether (100 mL). The organic layer was washed with 10% aqueous citric acid solution (2×50 mL). The phases were separated and the organic phase was dried over MgSO$_4$ and concentrated in vacuo. The crude product was sufficiently pure to be carried to the subsequent step.

STEP B: 3-{[2-[2,6-Bis(isopropyl)phenoxycarbonyl]-benzoyl]amino}-propanoic acid (101)

To a solution containing (102) (2.1 g, 6.4 mmol) and beta-alanine tert-butyl ester hydrochloride (1.16 g, 6.4 mmol) in DMF (20 mL) was added diisopropylethylamine (2.4 mL, 13.7 mmol) followed by O-(benzotriazol-1-yl)-N,N,N',N'-tetramethyluronium hexafluorophosphate (2.5 g, 6.5 mmol). The resulting reaction mixture was stirred at room temperature for 14 h, diluted with ethyl acetate (100 mL), washed with 10% aqueous citric acid solution (50 mL), followed by saturated aqueous NaHCO$_3$ solution (50 mL) and brine (2×50 mL). The organic phase was dried over MgSO$_4$ and concentrated in vacuo. The crude residue was dissolved in anhydrous dichloromethane (30 mL) and cooled to 0° C. before a solution of hydrochloric acid (10 mL, 4 N in dioxane) was added. The reaction was stirred for 1 h at 0° C. and 1 h at room temperature. The solvent was removed in vacuo and the crude residue was purified by preparative LC/MS to afford 0.85 g (38% yield over three steps) of the title compound (101). $^1$H NMR (400 MHz, CD$_3$OD): δ 8.20 (dd, J=7.6, 0.8 Hz, 1H), 7.70–7.68 (m, 1H), 7.63–7.59 (m, 1H), 7.49 (dd, J=7.6, 0.8 Hz, 1H), 7.22–7.17 (m, 3H), 3.54 (t, J=7.2 Hz, 2H), 3.06–3.00 (m, 2H), 2.57 (t, J=6.8 Hz, 2H), 1.19 (d, J=6.8 Hz, 12H). MS (ESI) m/z 398.3 (M+H$^+$).

Example 2

3-{[2-[2,6-Bis(isopropyl)phenoxycarbonyloxy]-benzoyl]amino}-propanoic acid (103)

STEP A: 2,6-Bis(isopropyl)phenoxycarbonyl chloride (104)

Phosgene (13 mL, 20% in toluene) was added to propofol (3.6 g, 20 mmol) under a nitrogen atmosphere. The mixture was cooled to 0° C. and N,N-dimethylaniline (3.3 mL, 26 mmol) was added dropwise. The reaction mixture was allowed to warm to room temperature slowly and stirred for 14 h. The solvent was removed in vacuo. The crude product was carried to next step without further purification.

STEP B: Benzyl 2-[2,6-Bis(isopropyl)phenoxycarbonyloxy]-benzoate (105)

To a cooled (0° C.) solution of benzyl salicylate (0.77 g, 3.3 mmol) in dichloromethane (6 mL) was added triethylamine (0.52 mL, 3.7 mmol) and a catalytic amount of DMAP. To this mixture a suspension of compound (104) (0.9 g, 3.7 mmol, crude product from last step) in dichloromethane (4 mL) was further added. The reaction was allowed to warm to room temperature slowly and stirred for 14 h. The reaction mixture was then diluted with 10% aqueous citric acid solution (10 mL) and extracted with ethyl ether (2×40 mL). The organic phase was dried over MgSO$_4$ and concentrated in vacuo. The residue was purified by radial chromatography on silica gel (eluting with ethyl acetate/hexane) to afford 0.8 g (57% yield over two steps) of the title compound (105).

STEP C: 2-[2,6-Bis(isopropyl)phenoxycarbonyloxy]-benzoic acid (106)

To a suspension of 10% Pd—C (100 mg) in ethyl acetate (15 mL) under nitrogen was added a solution of compound (105) (0.7 g, 1.6 mmol) in ethyl acetate (5 mL). The resulting suspension was degassed three times and then hydrogen gas was introduced. The reaction mixture was stirred under 1 atm hydrogen atmosphere for 14 h, then filtered through a small plug of celite. The filtrate was concentrated in vacuo. The crude product (106) was carried to next step without further purification.

STEP D: 3-{[2-[2,6-Bis(isopropyl)phenoxycarbonyloxy]-benzoyl]amino}-propanoic acid (103)

To a solution of crude compound (106) (0.4 g, 1.1 mmol) from above and beta-alanine tert-butyl ester hydrochloride (0.2 g, 1.1 mmol) in DMF (5 mL) was added diisopropylethylamine (0.41 mL, 2.3 mmol) followed by O-(benotriazol-1-yl)-N,N,N',N'-tetramethyluronium hexafluorophosphate (0.44 g, 1.1 mmol). The resulting reaction mixture was stirred at room temperature for 14 h, diluted with ethyl acetate (50 mL), washed with 10% aqueous citric acid solution (30 mL), followed by saturated aqueous NaHCO$_3$ solution (30 mL) and brine (2×20 mL). The organic phase was dried over MgSO$_4$ and concentrated in vacuo. The crude residue was then dissolved in anhydrous dichloromethane (5 mL) and cooled to 0° C. before a solution of hydrochloric acid (1 mL, 4 N in dioxane) was added. The reaction was stirred for 2 h at 0° C. and the solvent was removed in vacuo. The crude residue was purified by preparative LC/MS to afford 50 mg (8% yield over three steps) of the title compound (103). $^1$H NMR (400 MHz, CDCl$_3$): δ 7.85 (dd, J=7.6, 1.6 Hz, 1H), 7.51–7.48 (m, 1H), 7.34–7.13 (m, 5H), 3.72 (q, J=6.0 Hz, 2H), 3.13–3.10 (m, 2H), 2.67 (t, J=6.4 Hz, 2H), 1.25 (d, J=6.8 Hz, 12H). MS (ESI) m/z 414.3 (M+H$^+$).

Example 3

Analysis of Electrogenic Transport in SMVT-Expressing *Xenopus* Oocytes

Transporter Cloning: The complete open reading frame of human SMVT (SLC5A6) was amplified from human cDNA prepared from intestinal mRNA. Gene-specific oligonucleotide primers were designed against Genbank sequences (NM-021095). Amplified PCR products were cloned into a modified version of the mammalian expression vector pcDNA3 (termed pMO) that was engineered to contain the 5' and 3' untranslated regions from the *Xenopus* beta-globin gene. All clones were completely sequenced and tested for function by transient transfection in HEK293 cells. Radiolabeled $^3$H biotin was used to assess SMVT function (see method below).

*Xenopus* Oocyte Expression and Electrophysiology: cRNA for oocyte expression was prepared by linearization of plasmid cDNA and in vitro transcription using T7 polymerase (Epicentre Ampliscribe kit). *Xenopus* oocytes were prepared and maintained as previously described (Collins et al., *Proc. Natl. Acad. Sci.* 1997, 13:5456–5460) and injected with 10–30 ng RNA. Transport currents were measured 2–6 days later using two-electrode voltage-clamp (Axon Instruments). All experiments were performed using a modified oocyte ringers solution (90 mM NaCl, 2 mM KCl, 1.8 mM CaCl$_2$, 1 mM MgCl$_2$, and 10 mM NaHEPES, pH 7.4; in Na$^+$-free solutions 90 mM choline chloride was substituted for NaCl). The membrane potential of oocytes was held at −60 mV and current traces acquired using PowerLab software (ADInstruments). Full 7-concentration dose-responses were performed for each compound. Current responses at the highest concentration were normalized to the maximal biotin elicited currents (i.e., at 0.5 mM). Half-maximal concentrations were calculated using non-linear regression curve fitting software (Prism) with the Hill co-efficient fixed to 1. To ensure that currents were specific for the overexpressed transporter, all compounds were tested against uninjected oocytes. Since SMVT requires Na$^+$ for transport, transport specificity was confirmed by application of the compounds in a Na$^+$-free solution.

Compound (101) elicited SMVT-specific currents significantly above background (at least 10% of I$_{max}$ for biotin) when tested at 0.5 mM on oocytes expressing SMVT, confirming that this compound serves as a substrate for the transporter.

Finally, it should be noted that there are alternative ways of implementing the present invention. Accordingly, the disclosed embodiments are to be considered as illustrative and not restrictive, and the invention is not to be limited to the details given herein, but may be modified within the scope and equivalents of the appended claims. All publications and patents cited herein are incorporated by reference.

The invention claimed is:

1. A compound of Formula (I):

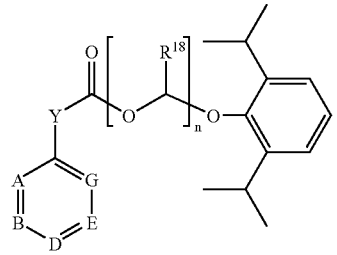

or pharmaceutically acceptable salts, hydrates, solvates or N-oxides thereof, wherein:

n is 0 or 1;

Y is selected from the group consisting of a bond, CR$^1$R$^2$, NR$^3$, O and S;

A is CR$^4$ or N;

B is CR$^5$ or N;

D is CR$^6$ or N;

E is CR$^7$ or N;

G is CR$^8$ or N;

R$^{18}$ is selected from the group consisting of hydrogen, alkyl, substituted alkyl, alkoxycarbonyl, aryl, substituted aryl, arylalkyl, carbamoyl, substituted carbamoyl, cycloalkyl, substituted cycloalkyl, cycloheteroalkyl, heteroaryl, substituted heteroaryl and heteroarylalkyl;

R$^1$ and R$^2$ are independently selected from the group consisting of hydrogen, alkyl, substituted alkyl, aryl, substituted aryl, arylalkyl, cycloalkyl, substituted cycloalkyl, cycloheteroalkyl, heteroaryl, substituted heteroaryl and heteroarylalkyl;

R$^3$ is selected from the group consisting of hydrogen, alkyl, substituted alkyl, aryl, arylalkyl, cycloalkyl and heteroaryl;

R$^4$ is selected from the group consisting of hydrogen, alkyl, substituted alkyl, alkoxy, substituted alkoxy, alkoxycarbonyl, aryl, substituted aryl, arylalkyl, carboxy, cycloalkyl, substituted cycloalkyl, cycloheteroalkyl, halo, heteroaryl, substituted heteroaryl, heteroarylalkyl, hydroxy and —W[C(O)]$_k$Z(CR$^9$R$^{10}$)$_r$CO$_2$R$^{11}$;

R$^5$ is selected from the group consisting of hydrogen, alkyl, substituted alkyl, alkoxy, substituted alkoxy, alkoxycarbonyl, aryl, substituted aryl, arylalkyl, carboxy, cycloalkyl, substituted cycloalkyl, cycloheteroalkyl, halo, heteroaryl, substituted heteroaryl, heteroarylalkyl, hydroxy and —W[C(O)]$_k$Z(CR$^9$R$^{10}$)$_r$CO$_2$R$^{11}$;

R$^6$ is selected from the group consisting of hydrogen, alkyl, substituted alkyl, alkoxy, substituted alkoxy, alkoxycarbonyl, aryl, substituted aryl, arylalkyl, carboxy, cycloalkyl, substituted cycloalkyl, cycloheteroalkyl, halo, heteroaryl, substituted heteroaryl, heteroarylalkyl, hydroxy and —W[C(O)]$_k$Z(CR$^9$R$^{10}$)$_r$CO$_2$R$^{11}$;

R$^7$ is selected from the group consisting of hydrogen, alkyl, substituted alkyl, alkoxy, substituted alkoxy, alkoxycarbonyl, aryl, substituted aryl, arylalkyl, carboxy, cycloalkyl, substituted cycloalkyl, cycloheteroalkyl, halo, heteroaryl, substituted heteroaryl, heteroarylalkyl, hydroxy and —W[C(O)]$_k$Z(CR$^9$R$^{10}$)$_r$CO$_2$R$^{11}$;

$R^8$ is selected from the group consisting of hydrogen, alkyl, substituted alkyl, alkoxy, substituted alkoxy, alkoxycarbonyl, aryl, substituted aryl, arylalkyl, carboxy, cycloalkyl, substituted cycloalkyl, cycloheteroalkyl, halo, heteroaryl, substituted heteroaryl, heteroarylalkyl, hydroxy and —W[C(O)]$_k$Z(CR$^9$R$^{10}$)$_r$CO$_2$R$^{11}$;

W is selected from the group consisting of a bond, CR$^{12}$R$^{13}$, NR$^4$, O and S;

Z is selected from the group consisting of CR$^{15}$R$^{16}$, NR$^{17}$, O and S;

k is 0 or 1;

r is 1, 2 or 3;

each of $R^9$, $R^{10}$, $R^{11}$, $R^{12}$, $R^{13}$, $R^{15}$ and $R^{16}$ is independently selected from the group consisting of hydrogen, alkyl, substituted alkyl, aryl, substituted aryl, arylalkyl, cycloalkyl, substituted cycloalkyl, cycloheteroalkyl, heteroaryl, substituted heteroaryl and heteroarylalkyl;

$R^{14}$ and $R^{17}$ are independently selected from the group consisting of hydrogen, alkyl, substituted alkyl, aryl, arylalkyl, cycloalkyl and heteroaryl;

with the provisos that:

at least one of A, B, D, E and G is not N;

one and only one of $R^4$, $R^5$, $R^6$, $R^7$ or $R^8$ is —W[C(O)]$_k$Z(CR$^9$R$^{10}$)$_r$CO$_2$R$^{11}$;

and if k is 0 then W is a bond.

2. The compound of claim 1, wherein n is 0.

3. The compound of claim 1, wherein n is 1, and $R^{18}$ is selected from hydrogen, benzyl, and substituted benzyl.

4. The compound of claim 1, wherein Y is a bond.

5. The compound of claim 1, wherein Y is CR$^1$R$^2$ and $R^1$ and $R^2$ are independently selected from hydrogen and methyl.

6. The compound of claim 1, wherein Y is O.

7. The compound of claim 1, wherein Y is S.

8. The compound of claim 1, wherein Y is NR$^3$, and $R^3$ is selected from hydrogen and methyl.

9. The compound of claim 1, wherein

A is CR$^4$;

B is CR$^5$;

D is CR$^6$;

E is CR$^7$;

G is CR$^8$;

$R^4$, $R^5$, $R^6$, $R^7$, and $R^8$ are independently selected from hydrogen and —W[C(O)]$_k$Z(CR$^9$R$^{10}$)$_r$CO$_2$R$^{11}$; and $R^9$, $R^{10}$, $R^{11}$, $R^{12}$, $R^{13}$, $R^{14}$, $R^{15}$, $R^{16}$, and $R^{17}$ are independently selected from hydrogen and C$_{1-4}$ alkyl.

10. A pharmaceutical composition comprising a pharmaceutically acceptable vehicle and a therapeutically effective amount of the compound of claim 1.

11. The pharmaceutical composition of claim 10 formulated for oral administration.

12. The pharmaceutical composition of claim 10 formulated for sustained release oral administration.

* * * * *